(12) United States Patent
Hallenbach et al.

(10) Patent No.: US 10,208,015 B2
(45) Date of Patent: Feb. 19, 2019

(54) ARYL-TRIAZOLYL PYRIDINES AS PEST CONTROL AGENTS

(71) Applicant: BAYER ANIMAL HEALTH GMBH, Leverkusen (DE)

(72) Inventors: Werner Hallenbach, Monheim (DE); Hans-Georg Schwarz, Dorsten (DE); Ulrich Goergens, Ratingen (DE); Kerstin Ilg, Cologne (DE); Andreas Turberg, Haan (DE); Sebastian Horstmann, Leverkusen (DE); Adeline Koehler, Langenfeld (DE)

(73) Assignee: BAYER ANIMAL HEALTH GMBH, Leverkusen (DE)

(*) Notice: Subject to any disclaimer, the term of this patent is extended or adjusted under 35 U.S.C. 154(b) by 0 days.

(21) Appl. No.: 15/325,665

(22) PCT Filed: Jul. 13, 2015

(86) PCT No.: PCT/EP2015/065933
§ 371 (c)(1),
(2) Date: Jan. 11, 2017

(87) PCT Pub. No.: WO2016/008830
PCT Pub. Date: Jan. 21, 2016

(65) Prior Publication Data
US 2017/0144988 A1 May 25, 2017

(30) Foreign Application Priority Data

Jul. 15, 2014 (EP) .................. 14177112

(51) Int. Cl.
*C07D 401/04* (2006.01)
*A01N 43/647* (2006.01)

(52) U.S. Cl.
CPC ......... *C07D 401/04* (2013.01); *A01N 43/647* (2013.01)

(58) Field of Classification Search
CPC .................................................. C07D 401/04
USPC ...................................... 546/268.4; 514/340
See application file for complete search history.

(56) References Cited

FOREIGN PATENT DOCUMENTS

WO 2012175474 A1 12/2012

OTHER PUBLICATIONS

International Search Report of PCT/EP2015/065933 dated Sep. 25, 2015.

*Primary Examiner* — Patricia L Morris
(74) *Attorney, Agent, or Firm* — McBee Moore Woodward & Vanik IP, LLC

(57) ABSTRACT

The invention relates to novel aryltriazolylpyridines of the general formula (I). Also described are processes for preparing the compounds of the formula (I). The compounds according to the invention are especially suitable for controlling insects and arachnids in agriculture, and ectoparasites in veterinary medicine.

18 Claims, No Drawings

ARYL-TRIAZOLYL PYRIDINES AS PEST CONTROL AGENTS

CROSS-REFERENCE TO RELATED APPLICATIONS

This application is a National Stage entry of International Application No. PCT/EP2015/065933 filed 13 Jul. 2015 which claims priority to European Patent Applications No. 14177112.1, filed 15 Jul. 2014.

BACKGROUND OF THE INVENTION

Field of the Invention

The present application relates to novel pyrazolyltriazolylpyridines, to processes for preparation thereof and to the use thereof for controlling animal pests, especially arthropods and in particular insects and arachnids.

Description of Related Art

WO2012175474-A1 describes certain phenyltriazolylpyridines as insecticidal compounds. Here, the general formula (A) comprises in its definitions of $A^1$ to $A^4$ CX (X represents hydrogen, halogen, cyano, $C_1$-$C_4$-alkyloxy, $C_1$-$C_4$-alkyl or $C_1$-$C_4$-haloalkyl) or nitrogen, where $Q^2$ denotes certain phenyl substituents. However, in the preferred ranges and in the examples, $A^1$, $A^2$ or $A^3$=nitrogen is not specified any further.

(A)

Modern crop protection compositions and veterinary ectoparasiticides have to meet many demands, for example in relation to dosage, persistence and spectrum of their action, and possible use. Questions of toxicity and of combinability with other active compounds or formulation auxiliaries play a role, as does the question of the expense that the synthesis of an active compound requires. In addition, resistances can occur. For all these reasons, the search for novel crop protection compositions or veterinary parasiticides can never be considered to be complete, and there is a constant need for novel compounds having improved properties compared to the known compounds at least in relation to individual aspects.

SUMMARY

It was an object of the present invention to provide compounds which widen the spectrum of the pesticides under various aspects and/or improve their activity.

It has now been found that, surprisingly, phenyltriazolylpyridines and their N-oxides and salts have biological properties superior to the prior art and are especially suitable for controlling animal pests, and therefore have particularly good usability in the agrochemical sector and in the animal health sector.

One aspect of the present invention relates to compounds of the formula (I)

(I)

in which
$R^1$ represents hydrogen or an optionally substituted group selected from the group consisting of $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl-$C_1$-$C_6$-alkyl, heteroaryl-$C_1$-$C_6$-alkyl; the chemical moieties
$A_1$ represents $CR^2$ or nitrogen (N),
$A_2$ represents N,
$A_3$ represents $CR^3$ or N,
$A_4$ represents $CR^4$ or N,
$B_1$ represents $CR^5$ or N,
$B_2$ represents $CR^6$ or N,
$B_3$ represents $CR^7$ or N,
$B_4$ represents $CR^8$ or N, and
$B_5$ represents $CR^9$ or N, but not more than two of the chemical moieties $A_1$ to $A_4$ simultaneously represent nitrogen and not more than two of the moieties $B_1$ to $B_5$ simultaneously represent nitrogen;
$R^2$, $R^3$, $R^4$, $R^5$, $R^6$, $R^8$ and $R^9$ independently of one another represent hydrogen, halogen, cyano, nitro, optionally substituted $C_1$-$C_6$-alkyl, $C_3$-$C_7$-cycloalkyl, $C_1$-$C_6$-alkoxy, N—($C_1$-$C_6$-alkoxy)imino-$C_1$-$C_3$-alkyl, $C_1$-$C_6$-alkylsulphanyl, $C_1$-$C_6$-alkylsulphinyl, $C_1$-$C_6$-alkylsulphonyl, N—($C_1$-$C_6$-alkyl)amino or N,N-di($C_1$-$C_6$-alkyl)amino, $C_1$-$C_6$-alkylsulphonylamino, N—($C_1$-$C_6$-alkyl)-$C_1$-$C_6$-alkylsulphonylamino; or
$R^2$, $R^3$, $R^4$, $R^5$, $R^6$, $R^8$ and $R^9$ independently of one another represent hydrogen, halogen, cyano, nitro, in each case optionally substituted $C_1$-$C_6$-alkyl, $C_3$-$C_7$-cycloalkyl, $C_1$-$C_6$-alkoxy, N—($C_1$-$C_6$-alkoxy)imino-$C_1$-$C_3$-alkyl, $C_1$-$C_6$-alkylsulphanyl, $C_1$-$C_6$-alkylsulphinyl, $C_1$-$C_6$-alkylsulphonyl, N—($C_1$-$C_6$-alkyl)amino or N,N-di($C_1$-$C_6$-alkyl)amino, $C_1$-$C_6$-alkylsulphonylamino, N—($C_1$-$C_6$-alkyl)-$C_1$-$C_6$-alkylsulphonylamino, phenyl;
$R^7$ represents halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino, preferably halogen, cyano, nitro or $C_1$-$C_6$-haloalkyl; or
$R^7$ represents halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino, preferably halogen, cyano, nitro or $C_1$-$C_6$-haloalkyl, phenyl;
$R^{10}$ independently of one another represents hydrogen, halogen, cyano, nitro, amino or optionally halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl;

W represents oxygen or sulphur;
Q represents hydrogen, formyl, hydroxy, amino or one of the optionally substituted moieties $C_1$-$C_6$-alkyl, $C_1$-$C_6$-alkyloxy, $C_3$-$C_6$-alkenyl, $C_3$-$C_6$-alkynyl, $C_3$-$C_7$-cycloalkyl, hetero-$C_1$-$C_6$-cycloalkyl, $C_3$-$C_6$-cycloalkyl-$C_1$-$C_6$-alkyl, aryl-$C_1$-$C_6$-alkyl, heteroaryl-$C_1$-$C_6$-alkyl or represents a moiety N—($C_1$-$C_6$-alkyl)amino, N—($C_1$-$C_6$-alkylcarbonyl)amino, N,N-di($C_1$-$C_6$-alkyl)amino; or
Q represents an unsaturated 6-membered carbocycle which is optionally polysubstituted by V or represents an unsaturated 5- or 6-membered heterocyclic ring which is optionally polysubstituted by V, where
V represents halogen, cyano, nitro, or one of the optionally substituted moieties $C_1$-$C_6$-alkyl, $C_2$-$C_6$-alkenyl, $C_2$-$C_6$-alkynyl, $C_3$-$C_7$-cycloalkyl, $C_1$-$C_6$-alkoxy, N—($C_1$-$C_6$-alkoxy)imino-$C_1$-$C_6$-alkyl, $C_1$-$C_6$-alkylsulphanyl, $C_1$-$C_6$-alkylsulphinyl, $C_1$-$C_6$-alkylsulphonyl, N,N-di($C_1$-$C_6$-alkyl)amino; and salts, N-oxides and tautomeric forms of the compounds of the formula (I).

DETAILED DESCRIPTION OF A PREFERRED EMBODIMENT

A preferred embodiment relates to a compound of the formula (I) according to the invention in which
$R^1$ represents hydrogen, methyl, ethyl, n-propyl, isopropyl, n-butyl, isobutyl, s-butyl, t-butyl, methoxymethyl, ethoxymethyl, propoxymethyl, 2-propyn-1-yl, 2-propen-1-yl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl; the chemical moieties
$A_1$ represents $CR^2$ or N,
$A_2$ represents N,
$A_3$ represents $CR^3$ or N,
$A_4$ represents $CR^4$ or N,
$B_1$ represents $CR^5$ or N,
$B_2$ represents $CR^6$ or N,
$B_3$ represents $CR^7$ or N,
$B_4$ represents $CR^8$ or N, and
$B_5$ represents $CR^9$ or N, but not more than two of the chemical moieties $A_1$ to $A_4$ simultaneously represent nitrogen and not more than two of the moieties $B_1$ to $B_5$ simultaneously represent nitrogen;
$R^2$ and $R^4$ independently of one another represent hydrogen, methyl, fluorine or chlorine; and
$R^3$ represents hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, N-methylamino, N,N-dimethylamino, N-ethylamino, N,N-diethylamino, methylsulphonylamino, N-methylmethylsulphonylamino;
$R^5$, $R^6$, $R^8$ and $R^9$ independently of one another represent hydrogen, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, but where $R^6$ and $R^{10}$ do not simultaneously represent hydrogen,
$R^7$ represents perfluorinated $C_1$-$C_6$-alkyl, perfluorinated $C_3$-$C_6$-cycloalkyl, $C_1$-$C_6$-alkoxy, N-alkoxyiminoalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, and also represents fluorine, chlorine, bromine, iodine, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino; or
$R^7$ represents perhalogenated, preferably perfluorinated $C_1$-$C_6$-alkyl, perhalogenated, preferably perfluorinated $C_3$-$C_6$-cycloalkyl, $C_1$-$C_6$-alkoxy, N-alkoxyiminoalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, and also represents fluorine, chlorine, bromine, iodine, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino, phenyl;
$R^{10}$ independently of one another represents hydrogen, halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl;
W represents oxygen or sulphur;
Q represents hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, 2-thienylmethyl, 3-thienylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, 2-oxo-2-(2,2,2-trifluoroethylamino)ethyl; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0-4 substituents V, where V independently of one another represents fluorine, chlorine, bromine, iodine, cyano, nitro, methyl, ethyl, isopropyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

A further preferred embodiment relates to a compound of the formula (I) according to the invention in which $R^1$ represents hydrogen, methyl, ethyl, n-propyl, isopropyl, n-butyl, isobutyl, s-butyl, t-butyl, methoxymethyl, ethoxymethyl, propoxymethyl, 2-propyn-1-yl, 2-propen-1-yl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl; the chemical moieties $A_1$ represents CH,
$A_2$ represents N,
$A_3$ represents $CR^3$, and
$A_4$ represents CH;
$B_1$ represents $CR^5$ or N,
$B_2$ represents CH,
$B_3$ represents $CR^7$,
$B_4$ represents $CR^8$, and
$B_5$ represents $CR^9$ or N, $R^3$ represents hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, N-methylamino, N,N-dimethylamino, N-ethylamino, N,N-diethylamino, methylsulphonylamino, N-methylmethylsulphonylamino;

$R^5$, $R^6$, $R^8$ and $R^9$ independently of one another represent hydrogen, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, but where $R^6$ and $R^{10}$ do not simultaneously represent hydrogen;

$R^7$ represents difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulphonyl, trifluoromethylsulphinyl, trifluoromethylsulphanyl; or $R^7$ represents difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulphonyl, trifluoromethylsulphinyl, trifluoromethylsulphanyl, phenyl;

$R^{10}$ independently of one another represents hydrogen, halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl;

W represents oxygen; and

Q represents hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, 2-thienylmethyl, 3-thienylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, 2-oxo-2-(2,2,2-trifluoroethylamino)ethyl; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0-4 substituents V, where V independently of one another represents fluorine, chlorine, bromine, iodine, cyano, nitro, methyl, ethyl, isopropyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

$R^5$ represents hydrogen, methyl, ethyl, 2-methylethyl, tert-butyl, fluorine, chlorine, bromine, iodine, nitro, trifluoromethyl, difluoromethoxy, trifluoromethoxy, amino.

A further preferred embodiment relates to a compound of the formula (I) according to the invention in which W represents oxygen;

$R^{10}$ represents hydrogen and $R^1$ represents hydrogen or methyl;

$B_3$ represents $CR^7$ and $R^7$ represents perhalogenated $C_1$-$C_4$-alkyl; or $B_3$ represents $CR^7$ and $R^7$ represents perhalogenated $C_1$-$C_4$-alkyl or phenyl;

Q represents cyclopropyl optionally substituted independently by F, Cl, Br, I or CN;

and all other parameters are as defined.

A further preferred embodiment relates to a compound of the formula (I) according to the invention in which W represents oxygen;

$R^{10}$ represents hydrogen and $R^1$ represents hydrogen or methyl;

$B_3$ represents $CR^7$ and $R^7$ represents —$C_3F_7$; or $B_3$ represents $CR^7$ and $R^7$ represents —$C_3F_7$ or phenyl; and Q represents cyclopropyl or 1-cyanocyclopropyl;

and all other parameters are as defined.

A further preferred embodiment relates to a compound of the formula (I) according to the invention in which $B_1$ represents $CR^5$, and $R^5$ represents halogen, $C_1$-$C_6$-alkoxy, $C_1$-$C_6$-alkyl, halogen- (preferably F—) substituted $C_1$-$C_6$-alkoxy or halogen- (preferably F—) substituted $C_1$-$C_6$-alkyl;

$B_2$ represents $CR^6$, where $R^6$ represents hydrogen or $C_1$-$C_6$-alkyl;

$B_4$ represents $CR^8$ or N, where $R^8$ represents hydrogen or $C_1$-$C_6$-alkyl;

$B_5$ represents $CR^9$ or N, where $R^9$ represents halogen, $C_1$-$C_6$-alkoxy or $C_1$-$C_6$-alkyl;

and all other parameters are as defined.

A further preferred embodiment relates to a compound of the formula (I) according to the invention in which $B_1$ represents $CR^5$, and $R^5$ represents Cl, Br, I, $C_1$-$C_4$-alkyl, F-substituted $C_1$-$C_4$-alkyl or F-substituted $C_1$-$C_4$-alkoxy, $B_2$ represents $CR^6$, where $R^6$ represents hydrogen, $B_4$ represents $CR^8$ or N, where $R^8$ represents hydrogen, $B_5$ represents $CR^9$ or N, where $R^9$ represents halogen or $C_1$-$C_4$-alkyl, and all other parameters are as defined.

A further preferred embodiment relates to a compound of the formula (I) according to the invention in which $A_1$ represents $CR^2$, where $R^2$ represents hydrogen or $C_1$-$C_4$-alkyl;

$A_2$ represents nitrogen;

$A_3$ represents $CR^3$, where $R^3$ represents halogen, $C_1$-$C_4$-alkyl, $C_1$-$C_4$-haloalkyl or $C_1$-$C_4$-alkoxy; and $A_4$ represents $CR^4$, where $R^4$ represents hydrogen or $C_1$-$C_4$-alkyl;

and all other parameters are as defined.

A further preferred embodiment relates to a compound of the formula (I) according to the invention in which $A_1$ represents $CR^2$, where $R^2$ represents hydrogen;

$A_2$ represents nitrogen;

$A_3$ represents $CR^3$, where $R^3$ represents halogen, $C_1$-$C_4$-alkyl, $C_1$-$C_4$-haloalkyl or $C_1$-$C_4$-alkoxy; and $A_4$ represents $CR^4$, where $R^4$ represents hydrogen;

and all other parameters are as defined.

A further preferred embodiment relates to a compound of the formula (I) according to the invention in which W represents oxygen, $R^{10}$ represents hydrogen and $R^1$ represents hydrogen or methyl, $A_1$ represents $CR^2$, where $R^2$ represents hydrogen or $C_1$-$C_4$-alkyl, $A_2$ represents nitrogen, $A_3$ represents $CR^3$, where $R^3$ represents halogen, $C_1$-$C_4$-alkyl, $C_1$-$C_4$-haloalkyl or $C_1$-$C_4$-alkoxy, $A_4$ represents $CR^4$, where $R^4$ represents hydrogen or $C_1$-$C_4$-alkyl, $B_1$ represents $CR^5$, and $R^1$ represents Cl, Br, I (preferably Cl), $C_1$-$C_4$-alkyl, F-substituted (preferably perfluorinated) $C_1$-$C_4$-alkyl, or F-substituted (preferably substituted by one, two or three F, more preferably substituted by two or three F) $C_1$-$C_4$-alkyl, $B_2$ represents $CR^6$, where $R^6$ represents hydrogen or $C_1$-$C_6$-alkyl, $B_3$ represents $CR^7$, where $R^7$ represents perhalogenated $C_1$-$C_4$-alkyl or phenyl, $B_4$ represents $CR^8$, where $R^8$ represents hydrogen or $C_1$-$C_6$-alkyl, $B_5$ represents $CR^9$, where $R^9$ represents halogen, $C_1$-$C_6$-alkoxy or $C_1$-$C_6$-alkyl, Q represents cyclopropyl or 1-cyanocyclopropyl.

A further preferred embodiment relates to a compound of the formula (I) according to the invention in which W represents oxygen, $R^{10}$ represents hydrogen and $R^1$ represents hydrogen or methyl, $A_1$ represents $CR^2$, where $R^2$ represents hydrogen;

$A_2$ represents nitrogen, $A_3$ represents $CR^3$, where $R^3$ represents $C_1$-$C_4$-alkyl (—$CH_3$, —$C_2H_5$, —$C_3H_7$, —$C_4H_9$), Cl, F, I or $C_1$-$C_4$-alkoxy (—O—$CH_3$, —O—$C_2H_5$, —O—$C_3H_7$, —O—$C_4H_9$), preferably $C_1$-$C_4$-alkyl (—$CH_3$, —$C_2H_5$, —$C_3H_7$, —$C_4H_9$), Cl or $C_1$-$C_4$-alkoxy (—O—$CH_3$, —O—$C_2H_5$, —O—$C_3H_7$, —O—$C_4H_9$), more preferably methyl, methoxy or Cl, $A_4$ represents $CR^4$, where $R^4$ represents hydrogen, $B_1$ represents $CR^5$, where $R^5$ represents F, Cl, Br, $C_1$-$C_4$-alkyl (—$CH_3$, —$C_2H_5$, —$C_3H_7$, —$C_4H_9$), F-substituted (preferably perfluorinated) $C_1$-$C_4$-alkyl (—$CF_3$, —$C_2F_5$, —$C_3F_7$, —$C_4F_9$), or F-substituted $C_1$-$C_4$-alkoxy (preferably $OCFH_2$, $OCF_2H$ or $OCF_3$, more preferably $OCF_2H$ or $OCF_3$), where $R^5$ preferably represents Cl, $CF_3$, $OCF_3$, $OCF_2H$, methyl or ethyl, $B_2$ represents $CR^6$, where $R^6$ represents hydrogen, $B_3$ represents $CR^7$, where $R^7$ represents perfluorinated $C_1$-$C_4$-alkyl or phenyl, preferably —$C_3F_7$ or phenyl, $B_4$ represents $CR^8$, where $R^8$ represents hydrogen, $B_5$ represents $CR^9$, where $R^9$ represents F, Cl, Br, I, $C_1$-$C_4$-alkyl, preferably Cl, Br, I or $C_1$-$C_4$-alkyl, particularly preferably Cl, I, Br or methyl, Q represents cyclopropyl, 1-cyanocyclopropyl, $C_1$-$C_4$-alkyl (—$CH_3$, —$C_2H_5$, —$C_3H_7$, —$C_4H_9$), or fluorinated $C_1$-$C_4$-alkyl (e.g. —$CHF_2$, $CH_2F$, —$CF_3$, —$C_2H_4F$, —$C_2H_3F_2$, —$C_2H_2F_3$, —$C_2HF_4$, —$C_2F_5$, —$C_3F_7$, —$C_4F_9$), preferably methyl, ethyl, propyl, $C_2H_2F_3$ (such as —$CH_2CF_3$), cyclopropyl or 1-cyanocyclopropyl.

A further aspect of the present invention relates to a pharmaceutical composition comprising at least one compound of the formula (I) according to the invention.

A further aspect of the present invention relates to a compound of the formula (I) according to the invention for use as medicaments.

A further aspect of the present invention relates to the use of a compound of the formula (I) according to the invention for preparing pharmaceutical compositions for controlling parasites on animals.

A further aspect of the present invention relates to the use of a compound of the formula (I) according to the invention for protecting the propagation material of plants, preferably for protecting seed.

A further aspect of the present invention relates to an intermediate of the formula (II)

A further aspect of the present invention relates to an intermediate of the formula (III)

A further aspect relates to the use of an intermediate of the formula (II) for synthesizing a compound of the formula (I) according to the invention.

A further aspect relates to the use of an intermediate of the formula (III) for synthesizing a compound of the formula (I) according to the invention.

Definitions

The person skilled in the art is aware that the expressions "a" or "an" as used in the present application may, depending on the situation, mean "one (1)", "one (1) or more" or "at least one (1)".

The expression "optionally substituted" means, if no specific substituents are stated, that the group in question may be mono- or polysubstituted by a substituent $M^1$, where in the case of polysubstitutions the substituents $M^1$ can be identical or different.

It is obvious to the person skilled in the art that examples given in the present application are not to be considered as limiting, but rather merely describe some embodiments in more detail.

The expressions "($C_n$-$C_m$)" and "$C_n$-$C_m$-" are exchangeable and relate to the minimum and maximum number of carbon atoms in an organic group. "($C_1$-$C_6$)" and "$C_1$-$C_6$-" alkyl, for example, relate to an alkyl group having 1, 2, 3, 4, 5 or 6 carbon atoms. The expressions "($C_n$)" and "$C_n$—" are likewise exchangeable and relate to the number of carbon atoms in an organic group. The expressions "$C_3$-cycloalkyl" and "($C_3$)-alkyl", for example, relate to cyclopropyl.

The definitions of the symbols given in the above formulae comprise collective terms which generally represent the following substituents:

According to the invention, "alkyl"—on its own or as a part of a chemical group—represents straight-chain or branched hydrocarbons having preferably 1 to 6 carbon atoms, particularly preferably 1, 2, 3 or 4 carbon atoms, for example methyl, ethyl, n-propyl, isopropyl, n-butyl, isobutyl, s-butyl, t-butyl. The alkyl radicals according to the invention may optionally be substituted by one or more identical or different radicals $M^1$.

According to the invention, "alkenyl"—on its own or as a part of a chemical group—represents straight-chain or branched hydrocarbons having preferably 2 to 6 carbon atoms, particularly preferably 2, 3 or 4 carbon atoms, and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, etc. The alkenyl radicals according to the invention may optionally be substituted by one or more identical or different radicals $M^1$.

According to the invention, "alkynyl"—on its own or as a part of a chemical group—represents straight-chain or branched hydrocarbons having preferably 2 to 6 carbon atoms, particularly preferably 2, 3 or 4 carbon atoms, and at least one triple bond, for example ethynyl, 2-propynyl, 2-butynyl, 3-butynyl, 1-methyl-2-propynyl, 2-pentynyl, 3-pentynyl, 4-pentynyl, 1-methyl-3-butynyl, etc. The alkynyl radicals according to the invention may optionally be substituted by one or more identical or different radicals $M^1$.

According to the invention, "cycloalkyl"—on its own or as part of a chemical group—represents mono-, bi- or tricyclic hydrocarbons preferably having 3 to 10 carbons, for example cyclopropyl, cyclobutyl, cyclopentyl, cyclohexyl, bicyclo[2.2.1]heptyl, bicyclo[2.2.2]octyl or adamantyl, particularly preferably cycloalkyl radicals having 3, 4, 5, 6 or 7 carbon atoms, for example cyclopropyl or cyclobutyl. The cycloalkyl radicals according to the invention may optionally be substituted by one or more identical or different radicals $M^1$.

According to the invention, "alkylcycloalkyl" represents mono-, bi- or tricyclic alkylcycloalkyl preferably having 4 to 10 or 4 to 7 carbon atoms, particularly preferably alkylcycloalkyl radicals having 4, 5 or 7 carbon atoms, for example ethylcyclopropyl or 4-methylcyclohexyl, where the alkylcycloalkyl is attached via the cycloalkyl moiety to the parent structure. The alkylcycloalkyl radicals according to the invention may optionally be substituted by one or more identical or different radicals $M^1$.

According to the invention, "cycloalkylalkyl" represents mono-, bi- or tricyclic cycloalkylalkyl preferably having 4 to 10 or 4 to 7 carbon atoms, particularly preferably cycloalkylalkyl radicals having 4, 5 or 7 carbon atoms, inter alia cyclopropylmethyl or cyclobutylmethyl, where the alkylcycloalkyl is attached via the alkyl moiety to the parent structure. The cycloalkylalkyl radicals according to the invention may optionally be substituted by one or more identical or different radicals $M^1$.

According to the invention, "alkoxy" represents straight-chain or branched O-alkyl preferably having 1 to 6 carbon atoms, more preferably alkoxy groups having 1 to 4 carbon atoms, for example methoxy, ethoxy, n-propoxy, iso-propoxy, n-butoxy, isobutoxy, s-butoxy or t-butoxy. The alkoxy groups according to the invention may optionally be substituted by one or more identical or different radicals $M^1$.

According to the invention, "alkylsulphanyl" represents straight-chain or branched S-alkyl preferably having 1 to 6 carbon atoms, more preferably alkylsulphanyl groups having 1 to 4 carbon atoms, for example methylthio, ethylthio, n-propylthio, isopropylthio, n-butylthio, isobutylthio, s-butylthio and t-butylthio. The alkylsulphanyl groups according to the invention may optionally be substituted by one or more identical or different radicals $M^1$.

According to the invention, "alkylsulphinyl" represents straight-chain or branched alkylsulphinyl preferably having 1 to 6 carbon atoms, more preferably alkylsulphinyl groups having 1 to 4 carbon atoms, for example methylsulphinyl, ethylsulphinyl, n-propylsulphinyl, isopropylsulphinyl, n-butylsulphinyl, isobutylsulphinyl, s-butylsulphinyl and t-butylsulphinyl. The alkylsulphinyl groups according to the invention may optionally be substituted by one or more identical or different radicals $M^1$.

According to the invention, "alkylsulphonyl" represents straight-chain or branched alkylsulphonyl preferably having 1 to 6 carbon atoms, more preferably alkylsulphonyl groups having 1 to 4 carbon atoms, for example methylsulphonyl, ethylsulphonyl, n-propylsulphonyl, isopropylsulphonyl, n-butylsulphonyl, isobutylsulphonyl, s-butylsulphonyl and t-butylsulphonyl. The alkylsulphonyl groups according to the invention may optionally be substituted by one or more identical or different radicals $M^1$.

According to the invention, "acyl" represents radicals containing an $X^1$—C(=O)—$X^2$ group, where $X^1$ and $X^2$ independently of one another represent an organic radical as defined in the present application or represent hydrogen or represent a bond to the parent structure of a compound of the formula (I). In particular, "acyl" is understood to mean organic acids, esters, aldehydes, alkylcarbonyl (alkyl-C(=O)—) and amides. Preferably, $X^1$ and $X^2$ each independently of one another represent a group, optionally substituted by one or more identical or different radicals $M^1$, selected from alkyl, alkylene (—$C_nH_{2n}$—), alkoxy, alkoxylene (—O—$C_nH_{2n}$—), amino, mono- or dialkylamino, or hydrogen, or a radical $X^1$ or $X^2$ represents a bond to the parent structure of a compound of the formula (I).

According to the invention "alkylcarbonyl" represents straight-chain or branched alkyl-C(=O)— preferably having 2 to 7 carbon atoms (including the carbon atom of the C(=O) group), more preferably alkylcarbonyl radicals having 2 to 5 carbon atoms (($C_1$-$C_4$)-alkyl-C(=O)—), such as methylcarbonyl, ethylcarbonyl, n-propylcarbonyl, isopropylcarbonyl, s-butylcarbonyl and t-butylcarbonyl. The alkylcarbonyl groups according to the invention may optionally be substituted by one or more identical or different radicals $M^1$.

According to the invention, "cycloalkylcarbonyl" represents straight-chain or branched cycloalkylcarbonyl preferably having 3 to 10 carbon atoms in the cycloalkyl moiety, more preferably cycloalkylcarbonyl having 3, 5 or 7 carbon atoms in the cycloalkyl moiety, for example cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. The cycloalkylcarbonyl groups according to the invention may optionally be substituted by one or more identical or different radicals $M^1$.

According to the invention, "alkoxycarbonyl"—on its own or as part of a chemical group—represents straight-chain or branched alkoxycarbonyl preferably having 1 to 6 carbon atoms, more preferably having 1, 2, 3 or 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl. The alkoxycarbonyl groups according to the invention may optionally be substituted by one or more identical or different radicals $M^1$.

According to the invention, "halogen" represents fluorine (F), chlorine (Cl), bromine (Br) or iodine (I).

The expressions "haloalkyl", "haloalkenyl", "haloalkynyl", "haloalkylcarbonyl", "haloalkoxy", "haloalkoxycarbonyl", "haloalkylsulphanyl", "haloalkylsulphinyl" or "haloalkylsulphonyl" as used herein refer to a chemical alkyl, alkenyl, alkynyl, alkylcarbonyl, alkoxy, alkoxycarbonyl, alkylsulphanyl, alkylsulphinyl or alkylsulphonyl group (in each case preferably having one to 6 carbon atoms or more preferably having one, two, three or four carbon atoms) substituted by at least one halogen. The halogen groups may be mono- or polysubstituted up to the maximum possible number of substituents (perhalogenated) by halogen. In the case of polysubstitution by halogen, the halogen atoms may be identical or different, and may all be bonded to one carbon atom or may be bonded to a plurality of carbon atoms. Here, halogen represents in particular fluorine, chlorine, bromine or iodine, preferably fluorine or chlorine and particularly preferably fluorine. In a preferred embodiment, perhalogenated groups are maximally substituted by only one type of halogen, e.g. perfluorinated methyl (trifluoromethyl; $CF_3$) or perfluorinated ethyl (pentafluoroethyl; $C_2F_5$). Some examples of "haloalkyl", "haloalkenyl", "haloalkynyl", "haloalkylcarbonyl", "haloalkoxy", "haloalkoxycarbonyl", "haloalkylsulphanyl", "haloalkylsulphinyl" or "haloalkylsulphonyl" are trichloromethyl ($CCl_3$), trifluoromethyl ($CF_3$), chlorodifluoromethyl ($CClF_2$), dichlorofluoromethyl ($CCl_2F$), 2,2-difluoroethyl ($F_2HCCH_2$), 2,2,2-trifluoroethyl ($F_3CCH_2$), pentafluoroethyl ($C_2F_5$), 2,2-difluoroethenyl ($CHCF_2$), 2-chloroethynyl (CHCCl), trifluoromethoxy —$OCF_3$, difluoromethoxy —$OCHF_2$, 1,1, 2,2-tetrafluoroethylthio, 2-chloro-1,1,2-trifluoroethylsulphinyl, trichloromethylsulphonyl, etc. The halo groups according to the invention can, if stated, optionally be substituted by one or more identical or different radicals $M^1$, provided at least one hydrogen atom at a carbon atom of the halo group is replaced by a halogen. An example of an $M^1$-substituted haloalkyl is 2-cyano-2,2-difluoroethyl (C(CN)F$_2$CH$_2$).

An amino group (—NH$_2$) may optionally be substituted by one or more identical or different radicals $M^1$.

Substituted amino such as mono- or disubstituted amino means a radical from the group of the substituted amino radicals which are N-substituted, for example, by one or two identical or different radicals from the group consisting of alkyl, hydroxy, amino, alkoxy, acyl and aryl; preferably N-mono- and N,N-dialkylamino, (for example methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di(methoxymethyl)amino or N,N-di(methoxyethyl) amino), N-mono- and N,N-diarylamino, such as optionally substituted anilines, acylamino, N,N-diacylamino, N-alkyl-N-arylamino, N-alkyl-N-acylamino and also saturated N-heterocycles; preference is given here to alkyl radicals having 1 to 4 carbon atoms; here, aryl is preferably phenyl or optionally substituted phenyl; for acyl, the definition given further above applies here, preferably (C$_1$-C$_4$)-alkyl-C(=O)—.

Substituted amino also includes quaternary ammonium compounds (salts) with four organic substituents on the nitrogen atom.

According to the invention, "hydroxyalkyl" represents a straight-chain or branched alcohol preferably having 1 to 6 carbon atoms, more preferably 1, 2, 3 or 4 carbon atoms, for example methanol, ethanol, n-propanol, isopropanol, n-butanol, isobutanol, s-butanol and t-butanol. The hydroxyalkyl groups according to the invention may be substituted by one or more identical or different radicals $M^1$.

According to the invention, "alkylaminocarbonyl" represents straight-chain or branched alkylaminocarbonyl having preferably 1 to 6 carbon atoms, more preferably 1, 2, 3 or 4 carbon atoms in the alkyl moiety, for example methylaminocarbonyl (—CONHCH$_3$), ethylaminocarbonyl, n-propylaminocarbonyl, isopropylaminocarbonyl, s-butylaminocarbonyl and t-butylaminocarbonyl. The alkylaminocarbonyl groups according to the invention may optionally be substituted by one or more identical or different radicals $M^1$.

According to the invention, "N,N-dialkylaminocarbonyl" (—C(=O)N(alkyl)$_2$) represents straight-chain or branched N,N-dialkylaminocarbonyl having preferably 1 to 6 carbon atoms per alkyl, more preferably 1, 2, 3 or 4 carbon atoms per alkyl, for example N,N-dimethylaminocarbonyl (—C(=O)N(CH$_3$)$_2$), N,N-diethylaminocarbonyl, N,N-di(n-propylamino)carbonyl, N,N-di(isopropylamino)carbonyl and N,N-di(s-butylamino)carbonyl. The N,N-dialkylaminocarbonyl groups according to the invention may optionally be substituted by one or more identical or different radicals $M^1$.

"Carbocycle", unless defined differently elsewhere, is in particular cycloalkyl, cycloalkenyl or aryl. A carbocycle is in particular a mono-, bi- or tricyclic C$_6$- to C$_{14}$-aryl. A carbocycle may optionally be substituted by one or more identical or different radicals $M^1$.

According to the invention, "aryl" represents a mono-, bi- or polycyclic aromatic system having preferably 6 to 14, in particular 6 to 10 ring carbon atoms such as, for example, phenyl, naphthyl, anthryl, phenanthrenyl, preferably phenyl.

In addition, aryl also represents polycyclic systems such as tetrahydronaphthyl, indenyl, indanyl, fluorenyl, biphenyl, where the bonding site is on the aromatic system. The aryl groups according to the invention may optionally be substituted by one or more identical or different radicals $M^1$.

According to the invention, "arylalkyl" represents an aryl-substituted alkyl radical having preferably 6 to 14, in particular 6 to 10 ring carbon atoms in the aryl moiety and 1 to 6, in particular 1 to 4 carbon atoms in the alkyl moiety. Arylalkyl may be substituted by one or more identical or different radicals in the alkyl and/or aryl moiety. Examples of such arylalkyls include benzyl and 1-phenylethyl. The arylalkyl groups according to the invention may optionally be substituted by one or more identical or different radicals $M^1$.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted by a substituent Z, where the point of attachment is located at a ring atom. Unless defined otherwise, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group of N, O and S, although no two oxygen atoms should be directly adjacent to one another. The heterocyclic rings usually contain not more than 4 nitrogen atoms and/or not more than 2 oxygen atoms and/or not more than 2 sulphur atoms. If the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo[3.2.1]octanyl or 1-azabicyclo[2.2.1]heptyl. In the case of optionally substituted heterocyclyl, the invention also embraces spirocyclic systems, for example 1-oxa-5-azaspiro[2.3]hexyl. The groups "heterocycle", "heterocyclic ring" or "heterocyclic ring system" according to the invention may optionally be substituted by one or more identical or different radicals $M^1$.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Of particular significance are heteroaryls, i.e. heteroaromatic systems. According to the invention, the expression "heteroaryl" represents heteroaromatic compounds, i.e. fully unsaturated aromatic heterocyclic compounds covered by the above definition of heterocycles, preferably 5- to 7-membered rings having 1 to 3, preferably 1 or 2, identical or different heteroatoms from the abovementioned group. Heteroaryls according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. Furthermore, the heteroaryl groups according to the invention may optionally be substituted by one or more identical or different radicals $M^1$.

For the purpose of the present invention, "substituted" group or group "substituted by at least one radical $M^1$" such as an optionally substituted alkyl, alkenyl, alkynyl, cycloalkyl, aryl, phenyl, benzyl, heterocyclyl, heteroaryl or amino radical, etc., is generally a group containing at least one hydrocarbon-containing or nitrogen-hydrogen-containing fraction where the hydrogen is replaced by a different atom or an atom group $M^1$. In other words, such a group is a substituted group derived from the unsubstituted parent structure, where the parent structure is substituted by one or more substituent(s) $M^1$, preferably 1, 2 or 3 radicals $M^1$, and the substituent(s) $M^1$ is/are each independently of one another selected from the group consisting of halogen, hydroxy, nitro, formyl, carboxy, cyano, amino, isocyano, azido, $(C_1-C_4)$-alkyl, $(C_1-C_4)$-haloalkyl, $(C_2-C_4)$-alkenyl, $(C_2-C_4)$-alkynyl, $(C_3-C_6)$-cycloalkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkoxy-$(C_1-C_6)$-alkyl, N—$(C_1-C_4)$-alkoxyimino-$(C_1-C_3)$-alkyl, $(C_1-C_4)$-alkylsulphanyl, $(C_1-C_4)$-haloalkylsulphanyl, $(C_1-C_4)$-alkoxycarbonyl, $(C_1-C_4)$-alkylcarbonyl, carbamoyl, $C_1-C_4$-alkylcarbamoyl, $C_3-C_7$-cycloalkylcarbamoyl, mono- and N,N-di$(C_1-C_4)$-alkylaminocarbonyl, amino, $(C_1-C_6)$-acylamino, mono- and N,N-di$(C_1-C_4)$-alkylamino, tri$(C_1-C_4)$-alkylsilyl, $(C_3-C_6)$-cycloalkyl, $C_6$-aryl, heterocyclyl having 3 to 6 ring atoms, where each of the last-mentioned cyclic groups may also be attached via heteroatoms or a divalent functional $CH_2$ or $C_2H_4$ group, $(C_1-C_4)$-alkylsulphinyl, where both enantiomers of the $(C_1-C_4)$-alkylsulphinyl group are included, $(C_1-C_4)$-alkylsulphonyl, $(C_1-C_4)$-alkylphosphinyl, $(C_1-C_4)$-alkylsulphanyl-$(C_1-C_4)$-alkyl, $(C_1-C_4)$-alkoxy-$(C_1-C_4)$-alkyl, mono- and N,N-di$(C_1-C_4)$-alkylamino-$(C_1-C_4)$-alkyl and hydroxy-$(C_1-C_4)$-alkyl. The radicals $M^1$ mentioned in an exemplary manner can be unsubstituted or optionally (e.g. alkyl or amino), if they contain hydrocarbon-containing or nitrogen-hydrogen-containing fractions, substituted by one or more, preferably 1, 2 or 3 radicals $M^2$, where $M^2$ independently of the others is selected from the group consisting of amino, hydroxy, halogen, nitro, cyano, isocyano, mercapto, isothiocyanato, carboxy and carboxamide. Substituted groups also include substituted groups explicitly mentioned. "Haloalkyl" is embraced, for example, by the expression "substituted alkyl" and represents a preferred embodiment of a substituted alkyl. This applies analogously to all other substituted groups.

If two or more radicals form one or more rings, these may be carbocyclic, heterocyclic, saturated, partially saturated, unsaturated, for example also aromatic and further-substituted.

Optionally substituted phenyl is preferably phenyl which is unsubstituted or mono- or polysubstituted, preferably mono-, di- or trisubstituted by identical or different radicals selected from the group consisting of halogen, cyano, isocyano, nitro; $(C_1-C_4)$-alkyl, $C_2-C_4$-alkenyl, $C_2-C_4$-alkynyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_3-C_6)$-cycloalkyl, $(C_1-C_4)$-haloalkyl, $(C_1-C_4)$-haloalkoxy, $(C_1-C_4)$-alkylsulphanyl, $(C_1-C_4)$-haloalkylsulphanyl, optionally substituted by at least one radical $M^1$, for example o-, m- and p-tolyl, dimethylphenyl radicals, 2-, 3- and 4-chlorophenyl, 2-, 3- and 4-fluorophenyl, 2-, 3- and 4-trifluoromethyl and -trichloromethylphenyl, 2,4-, 3,5-, 2,5- and 2,3-dichlorophenyl, o-, m- and p-methoxyphenyl.

Optionally substituted cycloalkyl is preferably cycloalkyl, which is unsubstituted or mono- or polysubstituted, preferably up to trisubstituted, by identical or different radicals selected from the group consisting of halogen, haloalkyl, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl and $(C_1-C_4)$-haloalkoxy.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, nitro and oxo, especially mono- or polysubstituted by radicals from the group of halogen, $(C_1-C_4)$-alkyl, $(C_1-C_4)$-alkoxy, $(C_1-C_4)$-haloalkyl and oxo, most preferably substituted by one or two $(C_1-C_4)$-alkyl radicals.

Examples of alkyl-substituted heteroaryls are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Not included are such combinations which contravene the laws of nature and which the person skilled in the art would therefore rule out on the basis of his/her expert knowledge. Ring structures having three or more adjacent oxygen atoms, for example, are excluded.

DETAILED DESCRIPTION

The aryltriazolylpyridines according to the invention are defined by the general formula (I)

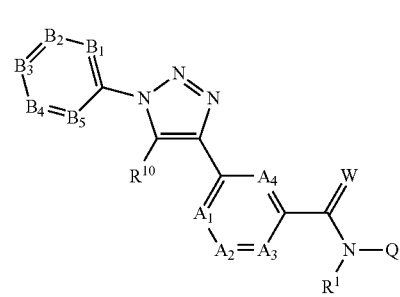

in which
$R^1$ represents hydrogen or an optionally substituted group selected from the group consisting of $C_1-C_6$-alkyl, $C_3-C_6$-alkenyl, $C_3-C_6$-alkynyl, $C_3-C_7$-cycloalkyl, $C_1-C_6$-alkylcarbonyl, $C_1-C_6$-alkoxycarbonyl, aryl-$C_1-C_6$-alkyl, heteroaryl-$C_1-C_6$-alkyl;
the chemical moieties
$A_1$ represents $CR^2$ or nitrogen,
$A_2$ represents nitrogen,
$A_3$ represents $CR^3$ or nitrogen and
$A_4$ represents $CR^4$ or nitrogen,
$B_1$ represents $CR^5$ or N,
$B_2$ represents $CR^6$ or N,
$B_3$ represents $CR^7$ or N,
$B_4$ represents $CR^8$ or N, and
$B_5$ represents $CR^9$ or N,
but not more than two of the chemical moieties $A_1$ to $A_4$ simultaneously represent nitrogen and not more than two of the moieties $B_1$ to $B_5$ simultaneously represent nitrogen;

$R^2$, $R^3$, $R^4$, $R^5$, $R^6$, $R^8$ and $R^9$ independently of one another represent hydrogen, halogen, cyano, nitro, optionally substituted $C_1$-$C_6$-alkyl, $C_3$-$C_7$-cycloalkyl, $C_1$-$C_6$-alkoxy, N—($C_1$-$C_6$-alkoxy)imino-$C_1$-$C_3$-alkyl, $C_1$-$C_6$-alkylsulphanyl, $C_1$-$C_6$-alkylsulphinyl, $C_1$-$C_6$-alkylsulphonyl, N—($C_1$-$C_6$-alkyl)amino or N,N-di($C_1$-$C_6$-alkyl)amino, $C_1$-$C_6$-alkylsulphonylamino, N—($C_1$-$C_6$-alkyl)-$C_1$-$C_6$-alkylsulphonylamino; or $R^2$, $R^3$, $R^4$, $R^5$, $R^6$, $R^8$ and $R^9$ independently of one another represent hydrogen, halogen, cyano, nitro, optionally substituted $C_1$-$C_6$-alkyl, $C_3$-$C_7$-cycloalkyl, $C_1$-$C_6$-alkoxy, N—($C_1$-$C_6$-alkoxy)imino-$C_1$-$C_3$-alkyl, $C_1$-$C_6$-alkylsulphanyl, $C_1$-$C_6$-alkylsulphinyl, $C_1$-$C_6$-alkylsulphonyl, N—($C_1$-$C_6$-alkyl)amino or N,N-di($C_1$-$C_6$-alkyl)amino, $C_1$-$C_6$-alkylsulphonylamino, N—($C_1$-$C_6$-alkyl)-$C_1$-$C_6$-alkylsulphonylamino, phenyl;

$R^7$ represents halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino, preferably halogen, cyano, nitro or $C_1$-$C_6$-haloalkyl; or $R^7$ represents halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino, preferably halogen, cyano, nitro or $C_1$-$C_6$-haloalkyl, phenyl;

$R^{10}$ independently of one another represents hydrogen, halogen, cyano, nitro, amino or optionally halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl;

W represents oxygen or sulphur;

Q represents hydrogen, formyl, hydroxy, amino or one of the optionally substituted moieties $C_1$-$C_6$-alkyl, $C_1$-$C_6$-alkyloxy, $C_3$-$C_6$-alkenyl, $C_3$-$C_6$-alkynyl, $C_3$-$C_7$-cycloalkyl, hetero-$C_1$-$C_6$-cycloalkyl, $C_3$-$C_6$-cycloalkyl-$C_1$-$C_6$-alkyl, aryl-$C_1$-$C_6$-alkyl, heteroaryl-$C_1$-$C_6$-alkyl or represents a moiety N—($C_1$-$C_6$-alkyl)amino, N—($C_1$-$C_6$-alkylcarbonyl)amino, N,N-di($C_1$-$C_6$-alkyl)amino; or Q represents an unsaturated 6-membered carbocycle which is optionally polysubstituted by V or represents an unsaturated 5- or 6-membered heterocyclic ring which is optionally polysubstituted by V, where V represents halogen, cyano, nitro, or one of the optionally substituted moieties $C_1$-$C_6$-alkyl, $C_2$-$C_6$-alkenyl, $C_2$-$C_6$-alkynyl, $C_3$-$C_7$-cycloalkyl, $C_1$-$C_6$-alkoxy, N—($C_1$-$C_6$-alkoxy)imino-$C_1$-$C_6$-alkyl, $C_1$-$C_6$-alkylsulphanyl, $C_1$-$C_6$-alkylsulphinyl, $C_1$-$C_6$-alkylsulphonyl, N,N-di($C_1$-$C_6$-alkyl)amino;

and salts, N-oxides and tautomeric forms of the compounds of the formula (I).

A preferred embodiment relates to compounds of the formula (I) in which $B_1$ represents $CR^5$ and $R^5$ represents halogen, optionally halogen- (preferably F—) substituted $C_1$-$C_6$-alkoxy or optionally halogen- (preferably F—) substituted $C_1$-$C_6$-alkyl, preferably Cl, Br, I, $C_1$-$C_4$-alkyl, F-substituted (preferably perfluorinated) $C_1$-$C_4$-alkyl, or F-substituted (preferably substituted by one, two or three F) $C_1$-$C_4$-alkoxy, more preferably Cl, $C_1$-$C_4$-alkyl, $C_1$-$C_4$-alkoxy substituted by one, two or three F or perfluorinated $C_1$-$C_4$-alkyl and particularly preferably Cl, $CF_3$, $OCHF_2$, $OCF_3$, methyl or ethyl.

A further preferred embodiment relates to compounds of the formula (I) in which $B_2$ represents $CR^6$ and $R^6$ represents hydrogen or $C_1$-$C_6$-alkyl, preferably hydrogen.

A further preferred embodiment relates to compounds of the formula (I) in which $B_4$ represents $CR^8$ and $R^8$ represents hydrogen or $C_1$-$C_6$-alkyl, preferably hydrogen.

A further preferred embodiment relates to compounds of the formula (I) in which $B_3$ represents $CR^7$ and $R^7$ represents halogen, cyano, nitro or $C_1$-$C_6$-haloalkyl, preferably perhalogenated $C_1$-$C_4$-alkyl, particularly preferably perfluorinated $C_1$-$C_4$-alkyl, very particularly preferably —$C_3F_7$, or $R^7$ represents halogen, cyano, nitro, $C_1$-$C_6$-haloalkyl or phenyl, preferably perhalogenated $C_1$-$C_4$-alkyl or phenyl, particularly preferably perfluorinated $C_1$-$C_4$-alkyl or phenyl, very particularly preferably —$C_3F_7$ or phenyl.

A preferred embodiment relates to compounds of the formula (I) in which $B_5$ represents $CR^9$ and $R^9$ represents halogen, $C_1$-$C_6$-alkoxy or $C_1$-$C_6$-alkyl, preferably halogen or $C_1$-$C_4$-alkyl and particularly preferably Cl, Br, I or methyl.

A further preferred embodiment relates to compounds of the formula (I) in which W represents oxygen.

A further preferred embodiment relates to compounds of the formula (I) in which $R^1$ and $R^{10}$ independently of one another represent hydrogen or $C_1$-$C_4$-alkyl, in which $R^{10}$ preferably represents hydrogen and $R^1$ preferably represents hydrogen or methyl, in which more preferably $R^1$ and $R^{10}$ represents hydrogen.

A further preferred embodiment relates to compounds of the formula (I) in which $A_1$ represents $CR^2$ and $R^2$ represents hydrogen or $C_1$-$C_4$-alkyl, preferably hydrogen.

A further preferred embodiment relates to compounds of the formula (I) in which $A_4$ represents $CR^4$ and $R^4$ represents hydrogen or $C_1$-$C_4$-alkyl, preferably hydrogen.

A further preferred embodiment relates to compounds of the formula (I) in which $A_3$ represents $CR^3$ and $R^3$ represents halogen or an optionally substituted group selected from the group consisting of $C_1$-$C_6$-alkyl and $C_1$-$C_6$-alkoxy, preferably halogen, $C_1$-$C_4$-alkyl, $C_1$-$C_4$-haloalkyl or $C_1$-$C_4$-alkoxy, particularly preferably Cl, methyl or methoxy.

A further preferred embodiment relates to compounds of the formula (I) in which Q represents hydrogen, hydroxy, formyl or optionally substituted $C_3$-$C_6$-cycloalkyl, preferably $C_3$-$C_6$-cycloalkyl which is optionally substituted independently by nitro, amino, halogen, $C_1$-$C_4$-alkoxy, cyano or hydroxycarbonyl, more preferably cyclopropyl which is optionally substituted independently by F, Cl, Br, I or CN, particularly preferably cyclopropyl, cyclopropyl monosubstituted by fluorine or chlorine, or cyanocyclopropyl (1-cyanocyclopropyl or 2-cyanocyclopropyl), very particularly preferably cyclopropyl or 1-cyanocyclopropyl. A further preferred embodiment relates to compounds of the formula (I) in which Q represents hydrogen, hydroxy, formyl or optionally substituted $C_3$-$C_6$-cycloalkyl or optionally substituted $C_1$-$C_4$-alkyl, preferably $C_3$-$C_6$-cycloalkyl which is optionally substituted independently by nitro, amino, halogen, $C_1$-$C_4$-alkoxy, cyano or hydroxycarbonyl, or $C_1$-$C_4$-alkyl which is optionally substituted by F, more preferably $C_1$-$C_4$-alkyl or cyclopropyl which is substituted independently by F, Cl, Br, I or CN, or $C_1$-$C_4$-alkyl which is substituted by F, particularly preferably cyclopropyl, cyclopropyl monosubstituted by fluorine or chlorine, or cyanocyclopropyl (1-cyanocyclopropyl or 2-cyanocyclopropyl), or in each case optionally F-substituted methyl, ethyl, propyl or butyl, very particularly preferably cyclopropyl or 1-cyanocyclopropyl or methyl or ethyl, or methyl substituted by 1, 2 or 3 F, or ethyl substituted by 1, 2, 3, 4 or 5 F.

A further preferred embodiment relates to compounds of the formula (I) in which

W represents oxygen, $R^{10}$ represents hydrogen and $R^1$ represents hydrogen or methyl, $A_1$ represents $CR^2$ or nitrogen, where $R^2$ represents hydrogen or $C_1$-$C_4$-alkyl, preferably hydrogen, $A_2$ represents nitrogen, $A_3$ represents $CR^3$ or nitrogen, where $R^3$ represents halogen or an optionally substituted group selected from the group consisting of $C_1$-$C_6$-alkyl and $C_1$-$C_6$-alkoxy, preferably halogen, $C_1$-$C_4$-alkyl, $C_1$-$C_4$-haloalkyl or $C_1$-$C_4$-alkoxy, $A_4$ represents $CR^4$ or nitrogen, where $R^4$ represents hydrogen or $C_1$-$C_4$-alkyl, preferably hydrogen, $B_1$ represents $CR^5$ or N, and $R^5$ represents halogen, optionally halogenated $C_1$-$C_6$-alkoxy or $C_1$-$C_6$-alkyl, preferably Cl, or $C_1$-$C_4$-alkyl optionally substituted by F, or $C_1$-$C_4$-alkoxy substituted by one, two or three F, and particularly preferably Cl, $CF_3$, $OCHF_2$, $OCF_3$, methyl or ethyl, $B_2$ represents $CR^6$ or N, where $R^6$ represents hydrogen or $C_1$-$C_6$-alkyl, preferably hydrogen, $B_3$ represents $CR^7$ or N, where $R^7$ represents halogen, cyano, nitro or $C_1$-$C_6$-haloalkyl, preferably perhalogenated $C_1$-$C_4$-alkyl, particularly preferably perfluorinated $C_1$-$C_4$-alkyl, very particularly preferably —$C_3F_7$, or $B_3$ represents $CR^7$ or N, where $R^7$ represents halogen, cyano, nitro, phenyl or $C_1$-$C_6$-haloalkyl, preferably perhalogenated $C_1$-$C_4$-alkyl or phenyl, particularly preferably perfluorinated $C_1$-$C_4$-alkyl or phenyl, very particularly preferably —$C_3F_7$ or phenyl, $B_4$ represents $CR^8$ or N, where $R^8$ represents hydrogen or $C_1$-$C_6$-alkyl, preferably hydrogen, $B_5$ represents $CR^9$ or N, where $R^9$ represents halogen, $C_1$-$C_6$-alkoxy or $C_1$-$C_6$-alkyl, preferably halogen or $C_1$-$C_4$-alkyl and particularly preferably Cl, Br, I or methyl, Q represents hydrogen, hydroxy, formyl or optionally substituted $C_3$-$C_6$-cycloalkyl, preferably $C_3$-$C_6$-cycloalkyl which is optionally substituted independently by nitro, amino, halogen, $C_1$-$C_4$-alkoxy, cyano or hydroxycarbonyl, more preferably cyclopropyl which is optionally substituted independently by F, Cl, Br, I or CN, particularly preferably cyclopropyl, cyclopropyl monosubstituted by fluorine or chlorine or cyanocyclopropyl (1-cyanocyclopropyl or 2-cyanocyclopropyl), very particularly preferably cyclopropyl or 1-cyanocyclopropyl, or Q represents cyclopropyl, cyclopropyl monosubstituted by fluorine or chlorine, or cyanocyclopropyl (1-cyanocyclopropyl or 2-cyanocyclopropyl), or in each case optionally F-substituted methyl, ethyl, propyl or butyl, very particularly preferably cyclopropyl or 1-cyanocyclopropyl or methyl or ethyl, or methyl substituted by one, two or three F or ethyl substituted by one, two, three, four or five F, but not more than two of the chemical moieties $A_1$ to $A_4$ simultaneously represent nitrogen and not more than two of the moieties $B_1$ to $B_5$ simultaneously represent nitrogen.

A further preferred embodiment relates to compounds of the formula (I) in which

W represents oxygen, $R^{10}$ represents hydrogen and $R^1$ represents hydrogen or methyl, $A_1$ represents $CR^2$, where $R^2$ represents hydrogen or $C_1$-$C_4$-alkyl, preferably hydrogen, $A_2$ represents nitrogen, $A_3$ represents $CR^3$, where $R^3$ represents halogen or an optionally substituted group selected from the group consisting of $C_1$-$C_6$-alkyl and $C_1$-$C_6$-alkoxy, preferably halogen, $C_1$-$C_4$-alkyl, $C_1$-$C_4$-haloalkyl or $C_1$-$C_4$-alkoxy, $A_4$ represents $CR^4$, where $R^4$ represents hydrogen or $C_1$-$C_4$-alkyl, preferably hydrogen, $B_1$ represents $CR^5$ or N, and $R^5$ represents halogen, optionally F-substituted $C_1$-$C_6$-alkoxy or $C_1$-$C_6$-alkyl, preferably Cl, or optionally F-substituted $C_1$-$C_4$-alkyl, or F-substituted alkoxy, and particularly preferably Cl, $CF_3$, $OCHF_2$, $OCF_3$, methyl or ethyl, $B_2$ represents $CR^6$ or N, where $R^6$ represents hydrogen or $C_1$-$C_6$-alkyl, preferably hydrogen, $B_3$ represents $CR^7$ or N, where $R^1$ represents halogen, cyano, nitro or $C_1$-$C_6$-haloalkyl, preferably perhalogenated $C_1$-$C_4$-alkyl, particularly preferably perfluorinated $C_1$-$C_4$-alkyl, very particularly preferably —$C_3F_7$, or $B_3$ represents $CR^7$ or N, where $R^7$ represents halogen, cyano, nitro, phenyl or $C_1$-$C_6$-haloalkyl, preferably perhalogenated $C_1$-$C_4$-alkyl or phenyl, particularly preferably perfluorinated $C_1$-$C_4$-alkyl or phenyl, very particularly preferably —$C_3F_7$ or phenyl, $B_4$ represents $CR^8$ or N, where $R^8$ represents hydrogen or $C_1$-$C_6$-alkyl, preferably hydrogen, $B_5$ represents $CR^9$ or N, where $R^9$ represents halogen, $C_1$-$C_6$-alkoxy or $C_1$-$C_6$-alkyl, preferably halogen or $C_1$-$C_4$-alkyl and particularly preferably Cl, Br, I or methyl, Q represents hydrogen, hydroxy, formyl or optionally substituted $C_3$-$C_6$-cycloalkyl, preferably $C_3$-$C_6$-cycloalkyl which is optionally substituted independently by nitro, amino, halogen, $C_1$-$C_4$-alkoxy, cyano or hydroxycarbonyl, more preferably cyclopropyl which is optionally substituted independently by F, Cl, Br, I or CN, particularly preferably cyclopropyl, cyclopropyl monosubstituted by fluorine or chlorine or cyanocyclopropyl (1-cyanocyclopropyl or 2-cyanocyclopropyl), very particularly preferably cyclopropyl or 1-cyanocyclopropyl, or Q represents cyclopropyl, cyclopropyl monosubstituted by fluorine or chlorine, or cyanocyclopropyl (1-cyanocyclopropyl or 2-cyanocyclopropyl), or in each case optionally F-substituted methyl, ethyl, propyl or butyl, very particularly preferably cyclopropyl or 1-cyanocyclopropyl or methyl or ethyl, or methyl substituted by one, two or three F or ethyl substituted by one, two, three, four or five F, but where not more than two of the moieties $B_1$ to $B_5$ simultaneously represent nitrogen.

A further preferred embodiment relates to compounds of the formula (I) in which

W represents oxygen, $R^{10}$ represents hydrogen and $R^1$ represents hydrogen or methyl, $A_1$ represents $CR^2$ or nitrogen, where $R^2$ represents hydrogen or $C_1$-$C_4$-alkyl, preferably hydrogen, $A_2$ represents nitrogen, $A_3$ represents $CR^3$ or nitrogen, where $R^3$ represents halogen or an optionally substituted group selected from the group consisting of $C_1$-$C_6$-alkyl and $C_1$-$C_6$-alkoxy, preferably halogen, $C_1$-$C_4$-alkyl, $C_1$-$C_4$-haloalkyl or $C_1$-$C_4$-alkoxy, $A_4$ represents $CR^4$ or nitrogen, where $R^4$ represents hydrogen or $C_1$-$C_4$-alkyl, preferably hydrogen, $B_1$ represents $CR^5$, and $R^5$ represents halogen, optionally F-substituted $C_1$-$C_6$-alkoxy or $C_1$-$C_6$-alkyl, preferably halogen or optionally F-substituted $C_1$-$C_4$-alkyl or F-substituted $C_1$-$C_4$-alkoxy and particularly preferably Cl, bromine, trifluoromethyl, difluoromethyl, difluoromethoxy, trifluoromethoxy, ethyl or methyl, $B_2$ represents $CR^6$, where $R^6$ represents hydrogen or $C_1$-$C_6$-alkyl, preferably hydrogen, $B_3$ represents $CR^7$, where $R^7$ represents halogen, cyano, nitro or $C_1$-$C_6$-haloalkyl, preferably perhalogenated $C_1$-$C_4$-alkyl, particularly preferably perfluorinated $C_1$-$C_4$-alkyl, very particularly preferably —$C_3F_7$, or $B_3$ represents $CR^7$, where $R^7$ represents halogen, cyano, nitro, phenyl or $C_1$-$C_6$-haloalkyl, preferably perhalogenated $C_1$-$C_4$-alkyl or phenyl, particularly preferably perfluorinated $C_1$-$C_4$-alkyl or phenyl, very particularly preferably —$C_3F_7$ or phenyl, $B_4$ represents $CR^8$, where $R^8$ represents hydrogen or $C_1$-$C_6$-alkyl, preferably hydrogen, $B_5$ represents $CR^9$, where $R^9$ represents halogen, $C_1$-$C_6$-alkoxy or $C_1$-$C_6$-alkyl, preferably halogen or $C_1$-$C_4$-alkyl and particularly preferably Cl, Br, I or methyl, Q represents hydrogen, hydroxy, formyl or optionally substituted $C_3$-$C_6$-cycloalkyl, preferably $C_3$-$C_6$-cycloalkyl which is optionally substituted independently by nitro, amino, halogen, $C_1$-$C_4$-alkoxy, cyano or hydroxycarbonyl, more preferably cyclopropyl which is optionally substituted independently by F, Cl, Br, I or CN, particularly preferably cyclopropyl, cyclopropyl monosubstituted by fluorine or chlorine or cyanocyclopropyl (1-cyanocyclopropyl or 2-cyanocyclopropyl), very particularly preferably cyclopropyl or 1-cyanocyclopropyl, or Q represents cyclopropyl, cyclopropyl monosubstituted by fluorine or chlorine, or cyanocyclopropyl (1-cyanocyclopropyl or 2-cyanocyclopropyl), or in each case optionally F-substituted methyl, ethyl, propyl or butyl, very particularly preferably cyclopropyl or 1-cyanocyclopropyl or methyl or ethyl, or methyl substituted by one, two or three F or ethyl substituted by one, two, three, four or five F, but where not more than two of the chemical moieties $A_1$ to $A_4$ simultaneously represent nitrogen.

A further preferred embodiment relates to compounds of the formula (I) in which

W represents oxygen, $R^{10}$ represents hydrogen and $R^1$ represents hydrogen or methyl, $A_1$ represents $CR^2$, where $R^2$ represents hydrogen or $C_1$-$C_4$-alkyl, preferably hydrogen, $A_2$ represents nitrogen, $A_3$ represents $CR^3$, where $R^3$ represents halogen or an optionally substituted group selected from the group consisting of $C_1$-$C_6$-alkyl and $C_1$-$C_6$-alkoxy, preferably halogen, $C_1$-$C_4$-alkyl, $C_1$-$C_4$-haloalkyl or $C_1$-$C_4$-alkoxy, $A_4$ represents $CR^4$, where $R^4$ represents hydrogen or $C_1$-$C_4$-alkyl, preferably hydrogen, $B_1$ represents $CR^5$, and $R^5$ represents halogen, optionally F-substituted $C_1$-$C_6$-alkoxy or $C_1$-$C_6$-alkyl, preferably halogen or optionally F-substituted $C_1$-$C_4$-alkyl or F-substituted $C_1$-$C_4$-alkoxy and particularly preferably Cl, bromine, trifluoromethyl, difluoromethyl, difluoromethoxy, trifluoromethoxy, ethyl or methyl, $B_2$ represents $CR^6$, where $R^6$ represents hydrogen or $C_1$-$C_6$-alkyl, preferably hydrogen, $B_3$ represents $CR^7$, where $R^7$ represents halogen, cyano, nitro or $C_1$-$C_6$-haloalkyl, preferably perhalogenated $C_1$-$C_4$-alkyl, particularly preferably perfluorinated $C_1$-$C_4$-alkyl, very particularly preferably —$C_3F_7$, or $B_3$ represents $CR^7$, where $R^7$ represents halogen, cyano, nitro, phenyl or $C_1$-$C_6$-haloalkyl, preferably perhalogenated $C_1$-$C_4$-alkyl or phenyl, particularly preferably perfluorinated $C_1$-$C_4$-alkyl or phenyl, very particularly preferably —$C_3F_7$ or phenyl, $B_4$ represents $CR^8$, where $R^8$ represents hydrogen or $C_1$-$C_6$-alkyl, preferably hydrogen, $B_5$ represents $CR^9$, where $R^9$ represents halogen, $C_1$-$C_6$-alkoxy or $C_1$-$C_6$-alkyl, preferably halogen or $C_1$-$C_4$-alkyl and particularly preferably Cl, Br, I or methyl, Q represents hydrogen, hydroxy, formyl or optionally substituted $C_3$-$C_6$-cycloalkyl, preferably $C_3$-$C_6$-cycloalkyl which is optionally substituted independently by nitro, amino, halogen, $C_1$-$C_4$-alkoxy, cyano or hydroxycarbonyl, more preferably cyclopropyl which is optionally substituted independently by F, Cl, Br, I or CN, particularly preferably cyclopropyl, cyclopropyl monosubstituted by fluorine or chlorine or cyanocyclopropyl (1-cyanocyclopropyl or 2-cyanocyclopropyl), very particularly preferably cyclopropyl or 1-cyanocyclopropyl, or Q represents cyclopropyl, cyclopropyl monosubstituted by fluorine or chlorine, or cyanocyclopropyl (1-cyanocyclopropyl or 2-cyanocyclopropyl), or in each case optionally F-substituted methyl, ethyl, propyl or butyl, very particularly preferably cyclopropyl or 1-cyanocyclopropyl or methyl or ethyl, or methyl substituted by one, two or three F or ethyl substituted by one, two, three, four or five F.

A further preferred embodiment relates to compounds of the formula (I) in which

W represents oxygen, $R^{10}$ represents hydrogen and $R^1$ represents hydrogen or methyl, $A_1$ represents $CR^2$, where $R^2$ represents hydrogen, $A_2$ represents nitrogen, $A_3$ represents $CR^3$, where $R^3$ represents F, Cl, Br, I, $C_1$-$C_4$-alkyl, $C_1$-$C_4$-haloalkyl (preferably perhalogenated $C_1$-$C_4$-alkyl, very particularly preferably perfluorinated $C_1$-$C_4$-alkyl ($CF_3$, $C_2F_5$, $C_3F_7$, $C_4F_9$), or $C_1$-$C_4$-alkoxy, $A_4$ represents $CR^4$, where $R^4$ represents hydrogen, $B_1$ represents $CR^5$, and $R^5$ represents halogen, optionally F-substituted $C_1$-$C_6$-alkoxy or $C_1$-$C_6$-alkyl, preferably halogen or optionally F-substituted $C_1$-$C_4$-alkyl or F-substituted $C_1$-$C_4$-alkoxy and particularly preferably F, Cl, Br, methyl or ethyl, very particularly preferably Cl, bromine, trifluoromethyl, difluoromethyl, difluoromethoxy, trifluoromethoxy, ethyl or methyl, $B_2$ represents $CR^6$, where $R^6$ represents hydrogen, $B_3$ represents $CR^7$, where $R^7$ represents perfluorinated $C_1$-$C_4$-alkyl, very particularly preferably $C_3F_7$, or $B_3$ represents $CR^7$, where $R^7$ represents perhalogenated $C_1$-$C_4$-alkyl or phenyl, particularly preferably perfluorinated $C_1$-$C_4$-alkyl or phenyl, very particularly preferably —$C_3F_7$ or phenyl, $B_4$ represents $CR^8$, where $R^8$ represents hydrogen, $B_5$ represents $CR^9$, where $R^9$ represents halogen, $C_1$-$C_6$-alkoxy or $C_1$-$C_6$-alkyl, preferably halogen or $C_1$-$C_4$-alkyl and particularly preferably Cl, Br, I or methyl, Q represents $C_3$-$C_6$-cycloalkyl which is optionally substituted independently by nitro, amino, halogen, $C_1$-$C_4$-alkoxy, cyano or hydroxycarbonyl, more preferably cyclopropyl which is optionally substituted independently by F, Cl, Br, I or CN, particularly preferably cyclopropyl, cyclopropyl monosubstituted by fluorine or chlorine or cyanocyclopropyl (1-cyanocyclopropyl or 2-cyanocyclopropyl), very particularly preferably cyclopropyl or 1-cyanocyclopropyl, or Q represents cyclopropyl, cyclopropyl monosubstituted by fluorine or chlorine, or cyanocyclopropyl (1-cyanocyclopropyl or 2-cyanocyclopropyl), or in each case optionally F-substituted methyl, ethyl, propyl or butyl, very particularly preferably cyclopropyl or 1-cyanocyclopropyl or methyl or ethyl, or methyl substituted by one, two or three F or ethyl substituted by one, two, three, four or five F.

Embodiments furthermore preferred relate to compounds of the formula (I)

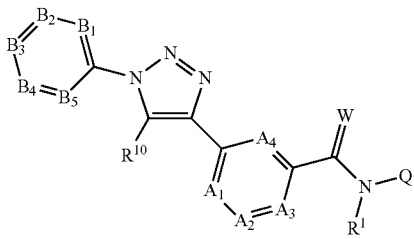

in which $R^1$ represents hydrogen, methyl, ethyl, n-propyl, isopropyl, n-butyl, isobutyl, s-butyl, t-butyl, methoxymethyl, ethoxymethyl, propoxymethyl, 2-propyn-1-yl, 2-propen-1-yl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl, preferably hydrogen or methyl;

the chemical moieties $A_1$ represents $CR^2$ or N,
$A_2$ represents N,
$A_3$ represents $CR^3$ or N, and
$B_4$ represents $CR^4$ or N,
$B_1$ represents $CR^5$ or N,
$B_2$ represents $CR^6$ or N,
$B_3$ represents $CR^7$ or N,
$B_4$ represents $CR^8$ or N, and
$B_5$ represents $CR^9$ or N, but not more than two of the chemical moieties $A_1$ to $A_4$ simultaneously represent nitrogen and not more than two of the moieties $B_1$ to $B_5$ simultaneously represent nitrogen;

$R^2$ and $R^4$ independently of one another represent hydrogen, methyl, fluorine or chlorine; and $R^3$ represents hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, N-methylamino, N,N-dimethylamino, N-ethylamino, N,N-diethylamino, methylsulphonylamino, N-methylmethylsulphonylamino;

$R^5$, $R^6$, $R^8$ and $R^9$ independently of one another represent hydrogen, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, trifluoromethylsulphanyl, N,N-dimethylamino, phenyl;

$R^{10}$ independently of one another represents hydrogen, halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl, preferably hydrogen;

W represents oxygen or sulphur, preferably oxygen;

Q represents hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, 2-thienylmethyl, 3-thienylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0-4 substituents V, where V independently of one another represents fluorine, chlorine, bromine, iodine, cyano, nitro, methyl, ethyl, isopropyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

A further embodiment relates to compounds of the formula (I)
in which
$R^1$ represents hydrogen, methyl, ethyl, n-propyl, isopropyl, n-butyl, isobutyl, s-butyl, t-butyl, methoxymethyl, ethoxymethyl, propoxymethyl, 2-propyn-1-yl, 2-propen-1-yl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl;
the chemical moieties
$A_1$ represents CH,
$A_2$ represents nitrogen,
$A_3$ represents $CR^3$, and
$A_4$ represents CH;
$B_1$ represents $CR^5$ or N,
$B_2$ represents CH,
$B_3$ represents $CR^7$,
$B_4$ represents $CR^8$, and
$B_5$ represents $CR^9$ or N;
$R^3$ represents hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, N-methylamino, N,N-dimethylamino, N-ethylamino, N,N-diethylamino, methylsulphonylamino, N-methylmethylsulphonylamino;
$R^5$, $R^6$, $R^8$ and $R^9$ independently of one another represent hydrogen, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, but where $R^6$ and $R^{10}$ do not simultaneously represent hydrogen;
$R^7$ represents difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulphonyl, trifluoromethylsulphinyl or trifluoromethylsulphanyl; or
$R^7$ represents perfluorinated $C_1$-$C_6$-alkyl, or phenyl;
$R^{10}$ independently of one another represents halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl;
W represents oxygen;
Q represents hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2- fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, 2-thienylmethyl, 3-thienylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0-4 substituents V, where V independently of one another represents fluorine, chlorine, bromine, iodine, cyano, nitro, methyl, ethyl, isopropyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino; and $R^5$ represents hydrogen, methyl, ethyl, 2-methylethyl, tert-butyl, fluorine, chlorine, bromine, iodine, nitro, trifluoromethyl, difluoromethoxy, trifluoromethoxy, amino.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable toxicity to warm-blooded species and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are effective against normally sensitive and resistant species and against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa;* from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon*

*solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex;* from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysa-* phis tulipae, Dysmicoccus spp., Empoasca spp., for example Empoasca abrupta, Empoasca fabae, Empoasca maligna, Empoasca solana, Empoasca stevensi, Eriosoma spp., for example Eriosoma americanum, Eriosoma lanigerum, Eriosoma pyricola, Erythroneura spp., Eucalyptolyma spp., Euphyllura spp., Euscelis bilobatus, Ferrisia spp., Geococcus coffeae, Glycaspis spp., Heteropsylla cubana, Heteropsylla spinulosa, Homalodisca coagulata, Hyalopterus arundinis, Hyalopterus pruni, Icerya spp., for example Icerya purchasi, Idiocerus spp., Idioscopus spp., Laodelphax striatellus, Lecanium spp., for example Lecanium corni (=Parthenolecanium corni), Lepidosaphes spp., for example Lepidosaphes ulmi, Lipaphis erysimi, Lycorma delicatula, Macrosiphum spp., for example Macrosiphum euphorbiae, Macrosiphum lilii, Macrosiphum rosae, Macrosteles facifrons, Mahanarva spp., Melanaphis sacchari, Metcalfiella spp., Metcalfa pruinosa, Metopolophium dirhodum, Monellia costalis, Monelliopsis pecans, Myzus spp., for example Myzus ascalonicus, Myzus cerasi, Myzus ligustri, Myzus ornatus, Myzus persicae, Myzus nicotianae, Nasonovia ribisnigri, Nephotettix spp., for example Nephotettix cincticeps, Nephotettix nigropictus, Nilaparvata lugens, Oncometopia spp., Orthezia praelonga, Oxya chinensis, Pachypsylla spp., Parabemisia myricae, Paratrioza spp., for example Paratrioza cockerelli, Parlatoria spp., Pemphigus spp., for example Pemphigus bursarius, Pemphigus populivenae, Peregrinus maidis, Phenacoccus spp., for example Phenacoccus madeirensis, Phloeomyzus passerinii, Phorodon humuli, Phylloxera spp., for example Phylloxera devastatrix, Phylloxera notabilis, Pinnaspis aspidistrae, Planococcus spp., for example Planococcus citri, Prosopidopsylla flava, Protopulvinaria pyriformis, Pseudaulacaspis pentagona, Pseudococcus spp., for example Pseudococcus calceolariae, Pseudococcus comstocki, Pseudococcus longispinus, Pseudococcus maritimus, Pseudococcus viburni, Psyllopsis spp., Psylla spp., for example Psylla buxi, Psylla mali, Psylla pyri, Pteromalus spp., Pyrilla spp., Quadraspidiotus spp., for example Quadraspidiotus juglansregiae, Quadraspidiotus ostreaeformis, Quadraspidiotus perniciosus, Quesada gigas, Rastrococcus spp., Rhopalosiphum spp., for example Rhopalosiphum maidis, Rhopalosiphum oxyacanthae, Rhopalosiphum padi, Rhopalosiphum rufiabdominale, Saissetia spp., for example Saissetia coffeae, Saissetia miranda, Saissetia neglecta, Saissetia oleae, Scaphoideus titanus, Schizaphis graminum, Selenaspidus articulatus, Sitobion avenae, Sogata spp., Sogatella furcifera, Sogatodes spp., Stictocephala festina, Siphoninus phillyreae, Tenalaphara malayensis, Tetragonocephela spp., Tinocallis caryaefoliae, Tomaspis spp., Toxoptera spp., for example Toxoptera aurantii, Toxoptera citricidus, Trialeurodes vaporariorum, Trioza spp., for example Trioza diospyri, Typhlocyba spp., Unaspis spp., Viteus vitifolii, Zygina spp.;

from the suborder of the Heteroptera, for example Anasa tristis, Antestiopsis spp., Boisea spp., Blissus spp., Calocoris spp., Campylomma livida, Cavelerius spp., Cimex spp., for example Cimex adjunctus, Cimex hemipterus, Cimex lectularius, Cimex pilosellus, Collaria spp., Creontiades dilutus, Dasynus piperis, Dichelops furcatus, Diconocoris hewetti, Dysdercus spp., Euschistus spp., for example Euschistus heros, Euschistus servus, Euschistus tristigmus, Euschistus variolarius, Eurygaster spp., Halyomorpha halys, Heliopeltis spp., Horcias nobilellus, Leptocorisa spp., Leptocorisa varicornis, Leptoglossus occidentalis, Leptoglossus phyllopus, Lygocoris spp., for example Lygocoris pabulinus, Lygus spp., for example Lygus elisus, Lygus hesperus, Lygus lineolaris, Macropes excavatus, Monalonion atratum, Nezara spp., for example Nezara viridula, Oebalus spp., Piesma quadrata, Piezodorus spp., for example Piezodorus guildinii, Psallus spp., Pseudacysta persea, Rhodnius spp., Sahlbergella singularis, Scaptocoris castanea, Scotinophora spp., Stephanitis nashi, Tibraca spp., Triatoma spp.;

from the order of the Hymenoptera, for example Acromyrmex spp., Athalia spp., for example Athalia rosae, Atta spp., Diprion spp., for example Diprion similis, Hoplocampa spp., for example Hoplocampa cookei, Hoplocampa testudinea, Lasius spp., Linepithema humile, Monomorium pharaonis, Sirex spp., Solenopsis invicta, Tapinoma spp., Urocerus spp., Vespa spp., for example Vespa crabro, Xeris spp.;

from the order of the Isopoda, for example Armadillidium vulgare, Oniscus asellus, Porcellio scaber;

from the order of the Isoptera, for example Coptotermes spp., for example Coptotermes formosanus, Comitermes cumulans, Cryptotermes spp., Incisitermes spp., Microtermes obesi, Odontotermes spp., Reticulitermes spp., for example Reticulitermes flavipes, Reticulitermes hesperus;

from the order of the Lepidoptera, for example Achroia grisella, Acronicta major, Adoxophyes spp., for example Adoxophyes orana, Aedia leucomelas, Agrotis spp., for example Agrotis segetum, Agrotis ipsilon, Alabama spp., for example Alabama argillacea, Amyelois transitella, Anarsia spp., Anticarsia spp., for example Anticarsia gemmatalis, Argyroploce spp., Barathra brassicae, Borbo cinnara, Bucculatrix thurberiella, Bupalus piniarius, Busseola spp., Cacoecia spp., Caloptilia theivora, Capua reticulana, Carpocapsa pomonella, Carposina niponensis, Cheimatobia brumata, Chilo spp., for example Chilo plejadellus, Chilo suppressalis, Choristoneura spp., Clysia ambiguella, Cnaphalocerus spp., Cnaphalocrocis medinalis, Cnephasia spp., Conopomorpha spp., Conotrachelus spp., Copitarsia spp., Cydia spp., for example Cydia nigricana, Cydia pomonella, Dalaca noctuides, Diaphania spp., Diatraea saccharalis, Earias spp., Ecdytolopha aurantium, Elasmopalpus lignosellus, Eldana saccharina, Ephestia spp., for example Ephestia elutella, Ephestia kuehniella, Epinotia spp., Epiphyas postvittana, Etiella spp., Eulia spp., Eupoecilia ambiguella, Euproctis spp., for example Euproctis chrysorrhoea, Euxoa spp., Feltia spp., Galleria mellonella, Gracillaria spp., Grapholitha spp., for example Grapholita molesta, Grapholita prunivora, Hedylepta spp., Helicoverpa spp., for example Helicoverpa armigera, Helicoverpa zea, Heliothis spp., for example Heliothis virescens, Hofmannophila pseudospretella, Homoeosoma spp., Homona spp., Hyponomeuta padella, Kakivoria flavofasciata, Laphygma spp., Leucinodes orbonalis, Leucoptera spp., for example Leucoptera coffeella, Lithocolletis spp., for example Lithocolletis blancardella, Lithophane antennata, Lobesia spp., for example Lobesia botrana, Loxagrotis albicosta, Lymantria spp., for example Lymantria dispar, Lyonetia spp., for example Lyonetia clerkella, Malacosoma neustria, Maruca testulalis, Mamestra brassicae, Melanitis leda, Mocis spp., Monopis obviella, Mythimna separata, Nemapogon cloacellus, Nymphula spp., Oiketicus spp., Oria spp., Orthaga spp., Ostrinia spp., for example Ostrinia nubilalis, Oulema melanopus, Oulema oryzae, Panolis flammea, Parnara spp., Pectinophora spp., for example Pectinophora gossypiella, Perileucoptera spp., Phthorimaea spp., for example Phthorimaea operculella, Phyllocnistis citrella, Phyllonorycter spp., for example *Phyllonorycter blancardella*, *Phyllonorycter crataegella*, *Pieris* spp., for example *Pieris rapae*, *Platynota stultana*, *Plodia interpunctella*, *Plusia* spp., *Plutella xylostella* (=*Plutella maculipennis*), *Prays* spp., *Prodenia* spp., *Protoparce* spp., *Pseudaletia* spp., for example *Pseudaletia unipuncta*, *Pseudoplusia includens*, *Pyrausta nubilalis*, *Rachiplusia nu*, *Schoenobius* spp., for example *Schoenobius bipunctifer*, *Scirpophaga* spp., for example *Scirpophaga innotata*, *Scotia segetum*, *Sesamia* spp., for example *Sesamia inferens*, *Sparganothis* spp., *Spodoptera* spp., for example *Spodoptera eradiana*, *Spodoptera exigua*, *Spodoptera frugiperda*, *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., for example *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., for example *Gryllotalpa gryllotalpa*, *Hieroglyphus* spp., *Locusta* spp., for example *Locusta migratoria*, *Melanoplus* spp., for example *Melanoplus devastator*, *Paratlanticus ussuriensis*, *Schistocerca gregaria*;

from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis*, *Ctenocephalides felis*, *Pulex irritans*, *Tunga penetrans*, *Xenopsylla cheopis*; from the order of the Thysanoptera, for example *Anaphothrips obscurus*, *Baliothrips biformis*, *Drepanothrips reuteri*, *Enneothrips flavens*, *Frankliniella* spp., for example *Frankliniella fusca*, *Frankliniella occidentalis*, *Frankliniella schultzei*, *Frankliniella tritici*, *Frankliniella vaccinii*, *Frankliniella williamsi*, *Heliothrips* spp., *Hercinothrips femoralis*, *Rhipiphorothrips cruentatus*, *Scirtothrips* spp., *Taeniothrips cardamomi*, *Thrips* spp., for example *Thrips palmi*, *Thrips tabaci*;

from the order of the Zygentoma (=Thysanura), for example *Ctenolepisma* spp., *Lepisma saccharina*, *Lepismodes inquilinus*, *Thermobia domestica*;

from the class of the Symphyla, for example *Scutigerella* spp., for example *Scutigerella immaculata*; pests from the phylum of the Mollusca, in particular from the class of the Bivalvia, for example *Dreissena* spp.;

and also from the class of the Gastropoda, for example *Arion* spp., for example *Arion ater rufus*, *Biomphalaria* spp., *Bulinus* spp., *Deroceras* spp., for example *Deroceras laeve*, *Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp, *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paraphelenchus* spp., *Paratrichodorus* spp., for example *Paratrichodorus minor*, *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve the action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Especially suitable are those extenders or carriers which are gaseous at standard temperature and under standard pressure, for example aerosol propellants such as halogenated hydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve the chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. The application is accomplished in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment of the invention, the compounds of the formula (I) are in the form of formulations or the use forms prepared from these formulations in a mixture with further compounds, preferably those as described below.

If one of the compounds mentioned below can occur in various tautomeric forms, these forms are also included even if not explicitly mentioned in each case.

Insecticides/Acaricides/Nematicides

The active compounds identified here by their common name are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomers], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active compounds, for example afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (1-1582, BioNeem, Votivo), and also the following compounds: 3-bromo-N-{2-bromo-4-chloro-6-[(1-cyclopropylethyl) carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl] phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino] ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl] carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbony l}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl] carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro- 5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example: http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid.

(3) Respiration inhibitors (respiratory chain inhibitors) that act on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.7) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-

(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide (4) inhibitors of mitosis and cell division, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity, for example (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copper-oxine, (5.28) propamidine, (5.29) propineb, (5.30) sulphur and sulphur preparations, for example calcium polysulphide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin.

(7) Amino acid and protein biosynthesis inhibitors, for example (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors such as, for example, (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) meptyldinocap.

(15) Further compounds, for example (15.1) benthiazole, (15.2) bethoxazine, (15.3) capsimycin, (15.4) carvone, (15.5) quinomethionate, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H- chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3 S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3- thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All the mixing components mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, in particular *B. cereus* strain CNCM 1-1562 or *Bacillus firmus*, strain 1-1582 (Accession number CNCM 1-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8

(Accession No. DSM-9660), *Lecanicillium* spp., in particular strain HRO LEC 12, *Lecanicillium lecanii*, (formerly known as *Verticillium lecanii*), in particular strain KVO1, *Metarhizium anisopliae*, in particular strain $F_{52}$ (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV),

*Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Bio-keeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), pyrethrum/pyrethrins, *Quassia amara*, *Quercus*, *Quillaja*, *Regalia*, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, *Brassicaceae* extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, peas and other types of vegetable, cotton, tobacco, oilseed rape, and also fruit plants (with the fruits apples, pears, citrus fruits and grapevines). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

The treatment according to the invention of the plants and plant parts with the compounds of the formula (I) is carried out directly or by allowing the compounds to act on their environment, habitat or storage space by the customary treatment methods, for example by dipping, spraying, evaporation, fogging, scattering, painting on, injecting and, in the case of propagation material, in particular the case of seed, furthermore by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore by dry seed treatment, by liquid seed treatment, by slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants, from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It also further comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occurs when one of the compounds of the formula (I) acts systemically is that the treatment of the seed protects not just the seed itself but also the plants resulting therefrom after emergence against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in greenhouses, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya bean, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which, for example, has been pre-swollen in water up to a particular stage (pigeon breast stage), which leads to better germination and to more homogeneous emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are produced in a known manner, by mixing compounds of the formula (I) with customary additives, for example customary extenders and solvents or diluents, dyes, wetters, dispersants, emulsifiers, antifoams, preservatives, secondary thickeners, stickers, gibberellins and also water.

Useful dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical compounds. Preference is given to using alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed-dressing formulations usable in accordance with the invention are all foam-inhibiting substances customary for formulation of active agrochemical compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz- und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For treatment of seed with the seed-dressing formulations usable in accordance with the invention, or the use forms prepared therefrom, all mixing units usable customarily for the seed dressing are useful. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the field of animal health, i.e. in the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable toxicity to warm-blooded species are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

In the animal health sector, i.e. in the field of veterinary medicine, the active compounds according to the present invention act against animal parasites, especially ectoparasites or, in a further embodiment, also endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acarids such as ticks, for example hard ticks or soft ticks, or mites such as scab mites, harvest mites, bird mites and the like, and also aquatic ectoparasites such as copepods.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

These parasites include:
From the order of the Anoplurida, for example, *Haematopinus* spp., *Linognathus* spp., *Pediculus* spp., *Phthirus* spp., *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*
From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*
From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus,*

*Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example, *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., Haemophysalis spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicomi, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

From the subclass of the copepods with the order of the Siphonostomatoida in particular the genera *Lepeophtheirus* and *Caligus*; the species *Lepeophtheirus salmonis, Caligus elongatus* and *Caligus clemensi* may be mentioned by way of example and with particular preference.

In general, the active compounds according to the invention can be employed directly when they are used for the treatment of animals. They are preferably employed in the form of pharmaceutical compositions which may comprise pharmaceutically acceptable excipients and/or auxiliaries known in the prior art.

In the sector of animal health and in animal husbandry, the active compounds are employed (administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active compound, such as collars, earmarks, tailmarks, limb bands, halters, marking devices, etc. The active compounds can be formulated as a shampoo or as suitable formulations applicable in aerosols or unpressurized sprays, for example pump sprays and atomizer sprays.

In the case of employment for livestock, poultry, domestic pets, etc., the active compounds according to the invention can be employed as formulations (for example powders, wettable powders ["WP"], emulsions, emulsifiable concentrates ["EC"], free-flowing compositions, homogeneous solutions and suspension concentrates ["SC"]), which contain the active compounds in an amount of 1% to 80% by weight, directly or after dilution (e.g. 100- to 10 000-fold dilution), or they can be used as a chemical bath.

In the case of use in the animal health sector, the active compounds according to the invention can be used in combination with suitable synergists, repellents or other active compounds, for example acaricides, insecticides, anthelmintics, anti-protozoal agents, in order to widen the activity spectrum. Potential mixing components for compounds of the formula (I) according to the invention may, in the case of applications in animal health, be one or more compounds from groups (In-1) to (In-25).

(In-1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; particular preference is given here, for applications against ectoparasites, to bendiocarb, carbaryl, methomyl, promacyl and propoxur; or organophosphates, e.g. acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion; particular preference is given here, for applications against ectoparasites, to azamethiphos, chlorfenvinphos, chlorpyrifos, coumaphos, cythioate, diazinon (dimpylate), dichlorvos (DDVP), dicrotophos, dimethoate, ethion (diethion), famphur (famophos), fenitrothion, fenthion (MPP), heptenophos, malathion, naled, phosmet (PMP, phtalofos) phoxim, propetamphos, temephos, tetrachlorvinphos (CVMP) and triclorfon/metrifonate.

(In-2) GABA-gated chloride channel antagonists, for example organochlorines, e.g. bromocyclene, chlordane and endosulfan (alpha-), heptachlor, lindane and toxaphene; particular preference is given here, for applications against ectoparasites, to endosulphan (alpha-) and lindane; or fiproles (phenylpyrazoles), e.g. acetoprole, ethiprole, fipronil, pyrafluprole, pyriprole, rizazole; particular preference is given here, for applications against ectoparasites, to fipronil and pyriprole; or arylisoxazolines, arylpyrrolines, arylpyrrolidines, for example fluralaner (known from WO2009/2024541, Ex. 11-1; but also compounds from WO2012007426, WO2012042006, WO2012042007, WO2012107533, WO2012120135, WO2012165186, WO2012155676, WO2012017359, WO2012127347, WO2012038851, WO2012120399, WO2012156400, WO2012163959, WO2011161130, WO2011073444, WO2011092287, WO2011075591, WO2011157748, WO 2007/075459, WO 2007/125984, WO 2005/085216, WO 2009/002809), afoxolaner (e.g. in WO2011149749) and structurally related arylpyrrolines (known, for example, from WO2009/072621, WO 2010020522, WO 2009112275, WO 2009097992, WO 2009072621, JP 2008133273, JP 2007091708), or arylpyrrolidines (e.g. in WO2012004326, WO2012035011, WO2012045700, WO 2010090344, WO 2010043315, WO 2008128711, JP 2008110971), and compounds from the group of the so-called metadiamides (known, for example, from WO2012020483, WO2012020484, WO2012077221, WO2012069366, WO2012175474, WO2011095462, WO2011113756, WO2011093415, WO2005073165); particular preference is given here, for applications against ectoparasites, to afoxolaner and fluaralaner.

(In-3) Sodium channel modulators/voltage-gated sodium channel blockers, for example pyrethroids, e.g. acrinathrin, allethrin (d-cis-trans, d-trans), bifenthrin, bioallethrin, bioallethrin S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans isomers], deltamethrin, dimefluthrin, empenthrin [(EZ)-(1R) isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans isomer], prallethrin, profluthrin, pyrethrins (pyrethrum), resmethrin, RU 15525, silafluofen, tefluthrin, tetramethrin [(1R) isomers)], tralomethrin, transfluthrin and ZXI 8901; particular preference is given here, for applications against ectoparasites, to the type I pyrethroids allethrin, bioallethrin, permethrin, phenothrin, resmethrin, tetramethrin and the type II pyrethroids (alphacyanopyrethroids) alpha-cypermethrin, cyfluthrin (beta-), cyhalothrin (lambda-), cypermethrin (alpha-, zeta-), deltamethrin, fenvalerate, flucythrinate, flumethrin, fluvalinate (tau-), and the ester-free pyrethroids etofenprox and silafluofen; or organochlorine compounds, e.g. DDT or methoxychlor. Active compounds from this class are very particularly suitable as mixing components, since they have a longer-lasting contact-repelling action and therefore extend the activity spectrum to include this component.

(In-4) Nicotinergic acetylcholine receptor agonists, for example neonicotinoids, e.g. acetamiprid, clothianidin, dinotefuran, imidacloprid, imidaclothin, nitenpyram, thiacloprid, thiamethoxam; particular preference is given here, for applications against ectoparasites, to chlothianidin, dinotefuran, imidacloprid, nitenpyram and thiacloprid; or nicotine.

(In-5) Allosteric acetylcholine receptor modulators (agonists), for example spinosyns, e.g. spinetoram and spinosad; particular preference is given here, for applications against ectoparasites, to spinosad and spinetoram.

(In-6) Chloride channel activators, for example avermectins/milbemycins, e.g. abamectin, doramectin, emamectin benzoate, eprinomectin, ivermectin, latidectin, lepimectin, milbemycin oxime, milbemectin, moxidectin and selamectin; indole terpenoids, for example nodulisporic acid derivatives, especially nodulisporic acid A; particular preference is given here, for applications against ectoparasites, to doramectin, eprinomectin, ivermectin, milbemycin oxime, moxidectin, selamectin and nodulisporic acid A.

(In-7) Juvenile hormone analogues, for example hydroprene (S—), kinoprene, methoprene (S—); or fenoxycarb; pyriproxyfen; particular preference is given here, for applications against ectoparasites, to methoprene (S—) and pyriproxyfen.

(In-8) Mite growth inhibitors, e.g. clofentezine, diflovidazin, hexythiazox, etoxazole; particular preference is given here, for applications against ectoparasites, to etoxazole.

(In-9) Slo-1 and latrophilin receptor agonists, for example cyclic depsipeptides, e.g. emodepside and its precursor PF1022A (known from EP 382173, compound I); particular preference is given here, for applications against ectoparasites, to emodepside.

(In-10) Oxidative phosphorylation inhibitors, ATP disruptors, for example diafenthiuron.

(In-12) Nicotinergic acetylcholine receptor antagonists, for example bensultap, cartap (hydrochloride), thiocylam, and thiosultap (sodium).

(In-13) Chitin biosynthesis inhibitors, type 0, for example benzoylureas, e.g. bistrifluron, chlorfluazuron, diflubenzuron, flucycloxuron, flufenoxuron, hexaflumuron, lufenuron, novaluron, noviflumuron, teflubenzuron and triflumuron; particular preference is given here, for applications against ectoparasites, to diflubenzuron, fluazuron, lufenuron and triflumuron.

(In-14) Chitin biosynthesis inhibitors, type 1, for example buprofezin.

(In-15) Moulting inhibitors, for example cyromazine and dicyclanil; particular preference is given here, for applications against ectoparasites, to cyromazine and dicyclanil.

(In-16) Ecdysone agonists/disruptors, for example diacylhydrazines, e.g. chromafenozide, halofenozide, methoxyfenozide and tebufenozide.

(In-17) Octopaminergic agonists, for example amitraz, cymiazole, chlordimeform and demiditraz; particular preference is given here, for applications against ectoparasites, to amitraz, cymiazole and demiditraz.

(In-18) Complex-III electron transport inhibitors, for example hydramethylnone; acequinocyl; fluacrypyrim.

(In-19) Complex-I electron transport inhibitors, for example from the group of the METI acaricides, e.g. fenazaquin, fenpyroximate, pyrimidifen, pyridaben, tebufenpyrad, tolfenpyrad; particular preference is given here, for applications against ectoparasites, to fenpyroximate, pyrimidifen and tolfenpyrad;

(In-20) Voltage-gated sodium channel blockers, for example indoxacarb and metaflumizone; particular preference is given here, for applications against ectoparasites, to indoxacarb and metaflumizone.

(In-21) Inhibitors of acetyl-CoA carboxylase, for example tetronic acid derivatives, e.g. spirodiclofen and spiromesifen; or tetramic acid derivatives, e.g. spirotetramat.

(In-22) Complex-II electron transport inhibitors, for example cyenopyrafen.

(In-23) Ryanodine receptor effectors, for example diamides, e.g. flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

(In-24) Further active compounds with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and additionally preparations based on *Bacillus firmus* (1-1582, BioNeem, Votivo) and the following known active compounds: 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134), [(6-trifluoromethylpyridin-3-yl)methyl](methyl)oxido-$\lambda^4$-sulphanylidenecyanamide (known from WO 2007/095229), sulfoxaflor (likewise known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazol-5-amine (known from WO 2006/043635), [(3 S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H, 11H-benzo[f]pyrano[4,3-b]chromen-4-yl] methyl cyclopropanecarboxylate (known from WO 2006/129714), 2-cyano-3-(difluoromethoxy)-N-ethylbenzenesulphonamide (known from WO 2005/035486), N-[1-(2,3-dimethylphenyl)-2-(3,5-dimethylphenyl) ethyl]-4,5-dihydro-2-thiazolamine (known from WO 2008/104503); penigequinolone A (known from EP 2248422 (compound I) and WO 2009/060015 (compound No. 11).

(In-25) Suitable synergists in the case of use together with ectoparasiticides here include MGK264 (N-octylbicycloheptenecarboxamide), piperonyl butoxide (PBO) and verbutin; particular preference is given here to piperonyl butoxide and MGK264.

In addition to these groups, it is also possible to use short-term repellents in mixtures or a combined application. Examples are DEET (N,N-diethyl-3-methylbenzamide), icaridin (1-piperidinecarboxylic acid), (1S,2OS)-2-methylpiperidinyl-3-cyclohexene-1-carboxamide (SS220), indalone (butyl 3,4-dihydro-2, 2-dimethyl-4-oxo-2H-pyran-6-carboxylate), dihydronepetalactones, nootkatone, IR3535 (3-[N-butyl-N-acetyl]-aminopropionic acid ethyl ester), 2-ethylhexane-1,3-diol, (1R,2R,5R)-2-(2-hydroxypropan-2-yl)-5-methyl-cyclohexan-1-ol, dimethyl benzene-1,2-dicarboxylate, dodecanoic acid, undecan-2-one, N,N-diethyl-2-phenylacetamide and essential oils or other plant ingredients with known repellent action, for example borneol, callicarpenal, 1,8-cineol (eucalyptol), carvacrol, b-citronellol, a-copaene, coumarin (or its synthetic derivatives known from US20120329832). Icaridin, indalone and IR3535 (3-[N-butyl-N-acetyl]-aminopropionic acid ethyl ester) are particularly preferred for use against ectoparasites.

From the aforementioned groups (In-1) to (In-25), preference is given to the following groups as mixing components: (In-2), (In-3), (In-4), (In-5), (In-6), (In-17), (In-25).

Particularly preferred examples of insecticidally or acaricidally active compounds, synergists or repellents as mixing components for the compounds of the formula (I) according to the invention are afoxolaner, allethrin, amitraz, bioallethrin, chlothianidin, cyfluthrin (beta-), cyhalothrin (lambda-), cymiazole, cypermethrin (alpha-, zeta-), cyphenothrin, deltamethrin, demiditraz, dinotefuran, doramectin, eprinomectin, etofenprox, fenvalerate, fipronil, fluazuron, flucythrinate, flumethrin, fluralaner, fluvalinate (tau-), icaridin, imidacloprid, ivermectin, MGK264, milbemycin oxime, moxidectin, nitenpyram, permethrin, phenothrin, piperonyl butoxide, pyriprole, resmethrin, selamectin, silafluofen, spinetoram, spinosad, tetramethrin, thiacloprid.

Examples of endoparasiticidally active compounds as mixing or combination partners are, for example, (without these or the enumerations that follow being intended to be limiting):

Anthelmintically active compounds include, for example, the following substances active against nematodes, trematodes and/or cestodes:

from the class of the macrocyclic lactones, for example: abamectin, emamectin, ivermectin, milbemectin, latidectin, lepimectin, selamectin, doramectin, eprinomectin, moxidectin, milbemycin, nemadectin;

from the class of the benzimidazoles and probenzimidazoles, for example: albendazole, albendazole sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the depsipeptides, preferably cyclic depsipetides, in particular 24-membered cyclic depsipetides, for example: emodepside, PF1022A (known from EP 382173, compound I);

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: derquantel, paraherquamide;

from the class of the salicylanilides, for example: bromoxanide, brotianide, clioxanide, closantel, niclosamide, oxyclozanide, rafoxanide, tribromsalane;

from the class of the substituted phenols, for example: bithionol, disophenol, hexachlorophene, niclofolan, meniclopholan, nitroxynil;

from the class of the organophosphates, for example: coumaphos, haloxon, crufomate, dichlorvos, naphthalofos, trichlorfon;

from the class of the piperazinones/quinolines, for example: praziquantel, epsiprantel;

from the class of the piperazines, for example: piperazines, hydroxyzine;

from the class of the tetracyclines, for example: chlortetracycline, doxycycline, oxytetracycline, rolitetracycline, tetracycline;

from the class of the various other classes, for example: amoscanate, bephenium, bunamidine, clonazepam, clorsulon, diamfenetide, dichlorophen, diethylcarbamazine, emetine, Hetolin, hycanthone, lucanthone, miracil, mirasan, niridazole, nitroxynil, nitroscanate, oltipraz, omphalotin, resorantel, oxamniquine.

Examples of active compounds against protozoa as mixing or combination partners are, for example:

from the class of the triazines, for example: toltrazuril, diclazuril, ponazuril, letrazuril;

from the class of the polyether ionophores, for example: salinomycin, maduramicin, narasin, monensin;

from the class of the macrocyclic lactones, for example: erythromycin, milbemycin;

from the class of the quinolones, for example: enrofloxacin, pradofloxacin;

from the class of the quinines, for example: chloroquin;

from the class of the pyrimidines, for example: pyrimethamine;

from the class of the sulphonamides, for example: sulfaquinoxaline, trimethoprim, sulfaclozine;

from the class of the thiamines, for example: amprolium;

from the class of the lincosamines, for example: clindamycin;

from the class of the carbanilides, for example: imidocarb;

from the class of the nitrofurans, for example: nifurtimox;

from the class of the quinazoline alkaloids, for example: halofuginone;

from the class of the various other classes, for example: oxamniquine, paromomycin; from the class of the vaccines or antigens of microorganisms, for example: *Babesia canis canis, Babesia canis rossi, Babesia canis vogeli, Dictyocaulus viviparus, Eimeria acervulina, Eimeria brunetti, Eimeria maxima, Eimeria mitis, Eimeria necatrix, Eimeria praecox, Eimeria tenella, Leishmania infantum;*

Parasitic protozoa include:

Mastigophora (Flagellata), for example Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, for example Trichomonadidae, for example, *Giardia lamblia, G. canis;*

Sarcomastigophora (Rhizopoda) such as Entamoebidae, for example, *Entamoeba histolytica*, Hartmanellidae, for example, *Acanthamoeba* sp., *Harmanella* sp.;

Apicomplexa (*Sporozoa*) such as Eimeridae, for example, *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium spec., Isospora belli, I. canis, I. felis, I. ohioensis, I. rivolta, I. spec., I. suis, Cystisospora spec., Cryptosporidium spec.*, in particular *C. parvum*; such as Toxoplasmadidae, for example *Toxoplasma gondii, Hammondia heydornii, Neospora caninum, Besnoitia besnoitii;* such as Sarcocystidae, for example *Sarcocystis bovicanis, S. bovihominis, S. ovicanis, S. ovifelis, S. neurona, S. spec., S. suihominis*, such as Leucozoidae, for example *Leucozytozoon simondi*, such as Plasmodiidae, for example *Plasmodium berghei, P. falciparum, P. malariae, P. ovale, P. vivax, P. spec.*, such as Piroplasmea, for example *Babesia argentina, B. bovis, B. canis, B. spec., Theileria parva, Theileria spec.*, such as Adeleina, for example *Hepatozoon canis, H. spec.*

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatig-* era spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hyporaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp.;

from the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

From the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, especially an arthropodicide such as an insecticide or an acaricide. A further aspect relates to the use of a compound of the formula (I) as an antiectoparasitic agent, especially an arthropodicide such as an insecticide or an acaricide, for example in animal husbandry, in animal breeding, in buildings for livestock or in the hygiene sector.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:
1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simulidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Intermediates

One aspect of the present invention relates to intermediates of the formula (II)

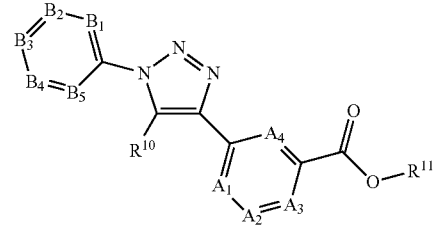

in which $A_1$, $A_2$, $A_3$, $A_4$, $B_1$, $B_2$, $B_3$, $B_4$, $B_5$, and $R^{10}$ have the meanings mentioned herein and $R^{11}$ represents hydrogen, methyl or ethyl.

A further aspect of the present invention relates to intermediates of the formula (III)

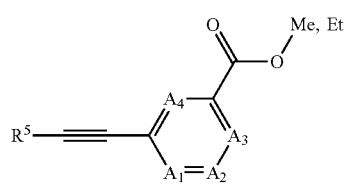

in which $A_1$, $A_2$, $A_3$, $A_4$, and $R^5$ have the meanings mentioned herein.

Preparation Processes

Compounds according to the invention of the general structure (I) can be prepared using the corresponding carboxylic esters (III) via intermediates (IIa (formula II, $R^{11}$=methyl, ethyl)) by the process shown in Reaction Scheme 1.

Reaction Scheme 1

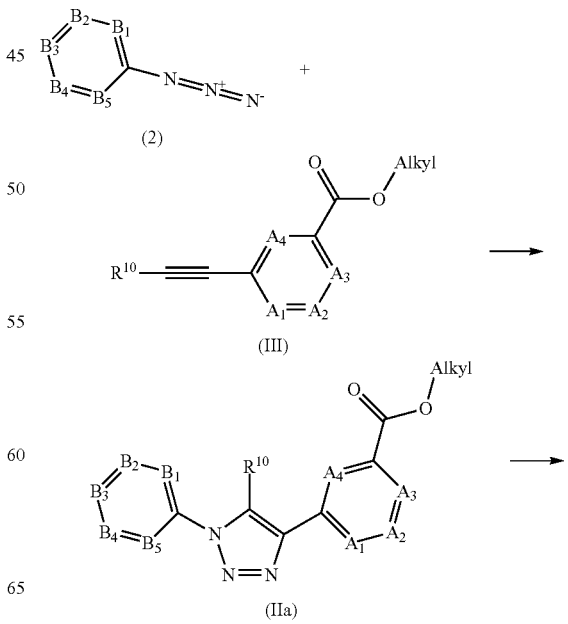

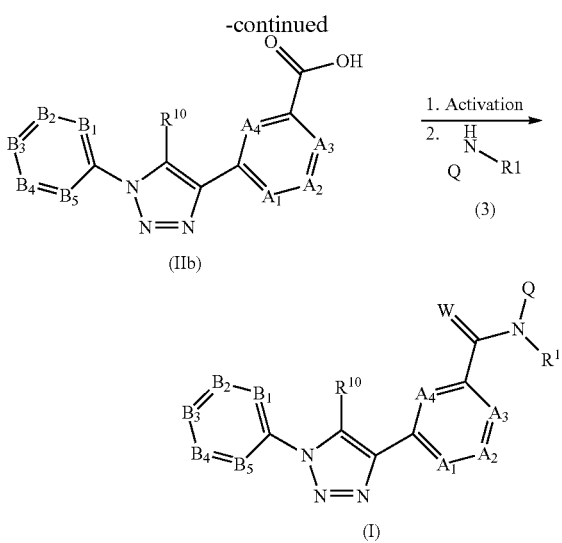

The radicals $A_1$ to $A_4$, $B_1$ to $B_5$, alkyl, Q, W, $R^1$ and $R^{10}$ are each as defined above.

Compounds according to the invention of the general structure (I) can be prepared using the corresponding carboxylic esters (III) via intermediates (IIa (formula II, $R^{11}$=methyl, ethyl)) from which the compounds (I) can be obtained successively by processes known to the person skilled in the art. Compounds of the structure (IIa) can be prepared by processes known from the literature from the respective halocarboxylic esters and acetylenes (e.g. WO2012/175474 A1, pp. 117-118).

Ring Closure with Ester
Step 1: Ester Ring Closure

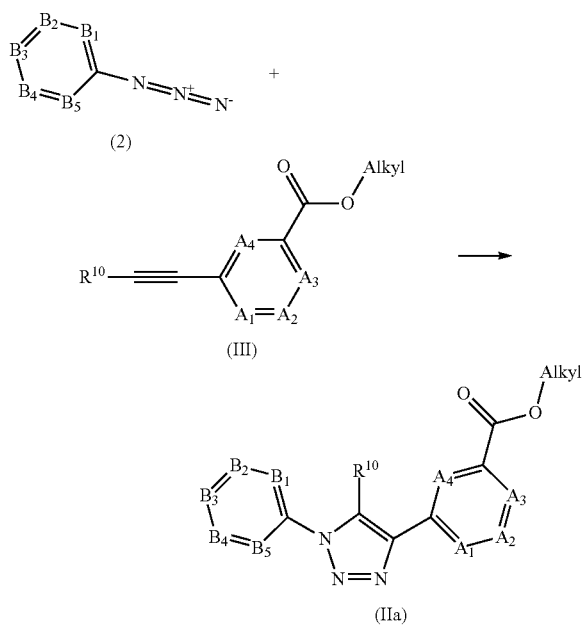

Compounds according to the invention of the general structure (IIa) are prepared by reacting the azides of the structure (2) with acetylenes of the structure (III).

The radicals $A^1$-$A^4$, $B^1$-$B^5$, $R^{10}$ and alkyl have the meanings described above.

The compounds of the structures (2) are known (e.g. WO2012175474) or can be prepared by methods known from the literature. The unknown compounds of the structure (III) can be prepared by the processes described for analogous compounds (e.g. WO2012/175474 A1, pp. 117-118). Examples of compounds of the structure (2) include: methyl 5-ethynyl-2-chloronicotinate, ethyl 5-ethynyl-2-chloronicotinate, methyl 5-ethynyl-2-methylnicotinate, ethyl 5-ethynyl-2-methylnicotinate. Examples of compounds of the structure (III) include: 2-azido-1,3-dichloro-5-[1,2,2,2-tetrafluoro-1-(trifluoromethyl)ethyl]benzene, 2-azido-1,3-dimethyl-5-[1,2,2,2-tetrafluoro-1-(trifluoromethyl)ethyl]benzene, 2-azido-1-ethyl-3-methyl-5-[1,2,2,2-tetrafluoro-1-(trifluoromethyl)ethyl]benzene, 2-azido-1-chloro-5-[1,2,2,2-tetrafluoro-1-(trifluoromethyl)ethyl]-3-(trifluoromethyl)benzene, 2-azido-1-methyl-5-[1,2,2,2-tetrafluoro-1-(trifluoromethyl)ethyl]-3-(trifluoromethyl)benzene, 2-azido-1-chloro-5-[1,2,2,2-tetrafluoro-1-(trifluoromethyl)ethyl]-3-(trifluoromethoxy)benzene, 2-azido-1-methyl-5-[1,2,2,2-tetrafluoro-1-(trifluoromethyl)ethyl]-3-(trifluoromethoxy)benzene. The reaction is conducted under the conditions described in the literature (e.g. WO2010008831, p. 52.; WO2012175474, p. 118).

Steps 2,3: Hydrolysis, amidation

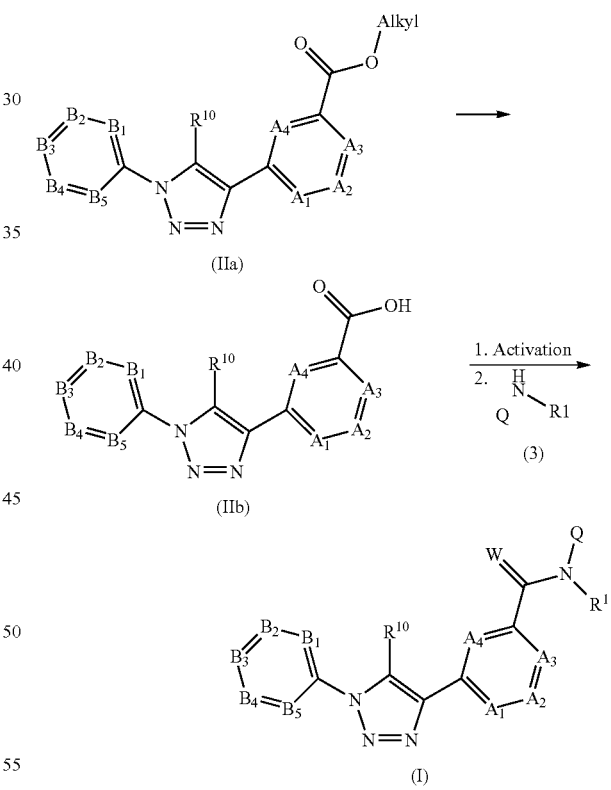

Compounds according to the invention of the general structure (I) can be prepared analogously to peptide coupling methods known from the literature from starting materials (IIb) and (3) [WO2010-051926; WO2010-133312]. Compounds of the general structure (IIb) can be prepared analogously to processes known from the literature by ester hydrolysis from compounds of the general structure (IIa) [WO2010-051926; WO2010-133312]. The radicals $A^1$-$A^4$, $B^1$-$B^5$, alkyl, Q, $R^1$ and $R^{10}$ have the meanings described above.

Ring Closure with Amide

Alternatively, compounds according to the invention of the general structure (I) can be prepared by the processes described in WO2012107434-A1 from phenyl azides of the structure (2) and acetylene compounds of the structures (3) in a [2+3] cycloaddition. Compounds of the structure (2) are known from WO2012107434-A1 or can be prepared by processes known from the literature. Compounds of the structure (3) can be prepared analogously to the processes, known from the literature, used for preparing the compounds of the structure (III) from the respective halocarboxamides and acetylenes.

Reaction Scheme 2

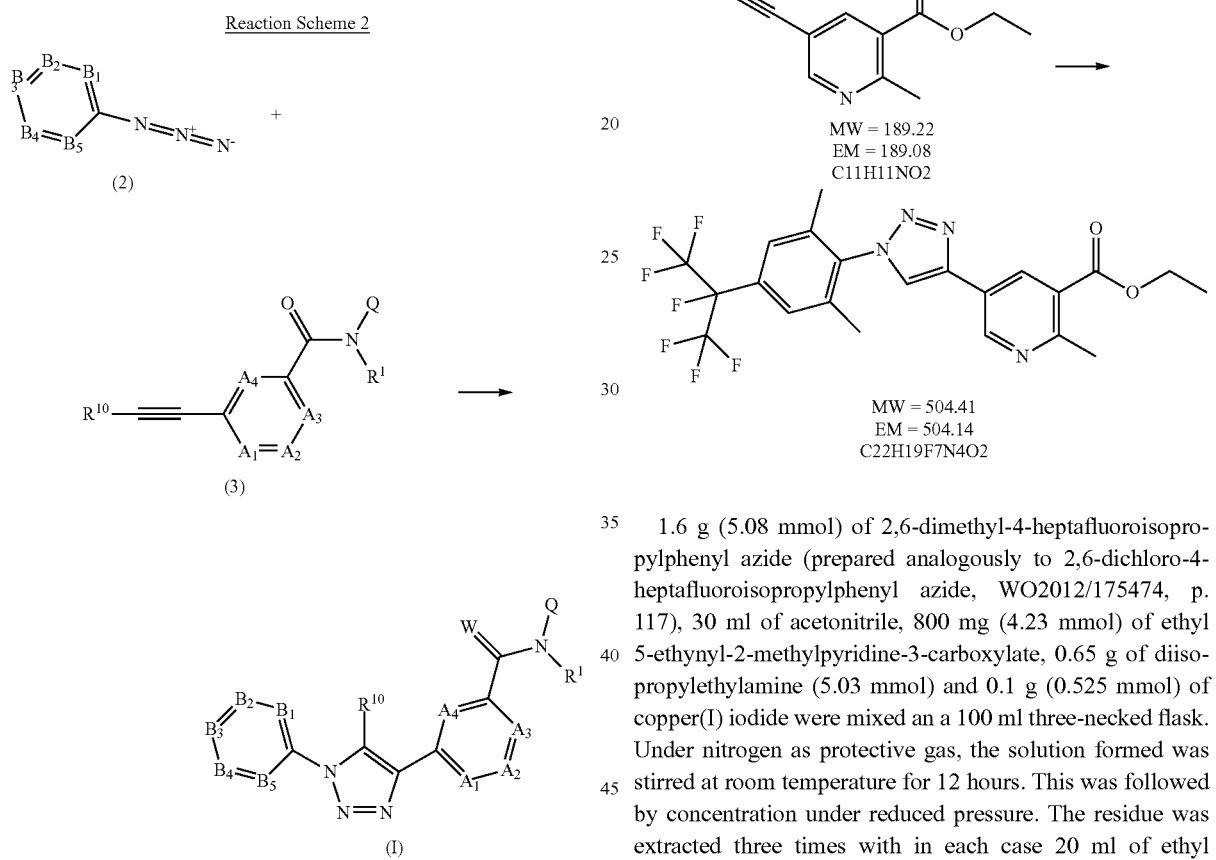

EXPERIMENTAL PART

Example 1

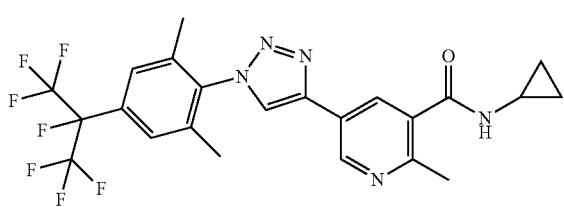 [SMILES: Cc1cc(C(F)(C(F)(F)F)C(F)(F)F)cc(C)c1-n1cc(-c2cnc(C)c(C(=O)NC3CC3)c2)nn1]

Step 1

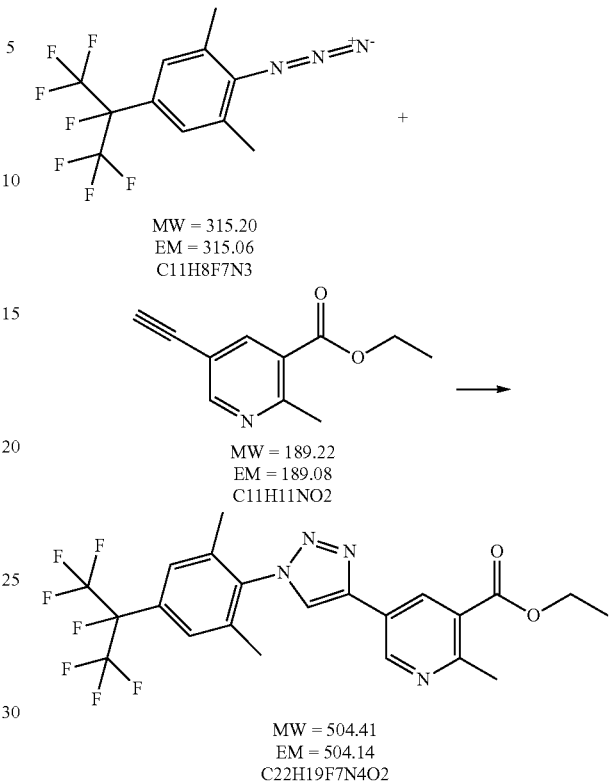

1.6 g (5.08 mmol) of 2,6-dimethyl-4-heptafluoroisopropylphenyl azide (prepared analogously to 2,6-dichloro-4-heptafluoroisopropylphenyl azide, WO2012/175474, p. 117), 30 ml of acetonitrile, 800 mg (4.23 mmol) of ethyl 5-ethynyl-2-methylpyridine-3-carboxylate, 0.65 g of diisopropylethylamine (5.03 mmol) and 0.1 g (0.525 mmol) of copper(I) iodide were mixed an a 100 ml three-necked flask. Under nitrogen as protective gas, the solution formed was stirred at room temperature for 12 hours. This was followed by concentration under reduced pressure. The residue was extracted three times with in each case 20 ml of ethyl acetate. The combined organic phases were then washed once with 20 ml of saturated aqueous sodium chloride solution, dried with anhydrous sodium sulphate and concentrated under reduced pressure. The residue of ethyl 5-[1-[2,6-dimethyl-4-[1,2,2,2-tetrafluoro-1-(trifluoromethyl)ethyl]phenyl]triazol-4-yl]-2-methylpyridine-3-carboxylate was used for the next step.

The following compounds were prepared analogously:

methyl 2-chloro-5-[1-[2,6-dimethyl-4-[1,2,2,2-tetrafluoro-1-(trifluoromethyl)ethyl]phenyl]triazol-4-yl]pyridine-3-carboxylate ethyl 5-[1-[2,6-dichloro-4-[1,2,2,2-tetrafluoro-1-(trifluoromethyl)ethyl]phenyl]triazol-4-yl]-2-methylpyridine-3-carboxylate methyl 2-chloro-5-[1-[2,6-dichloro-4-[1,2,2,2-tetrafluoro-1-(trifluoromethyl)ethyl]phenyl]triazol-4-yl]pyridine-3-carboxylate Step 2

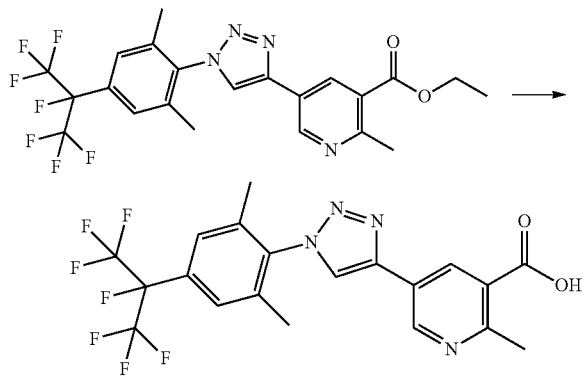

Ethyl 5-[1-[2,6-dimethyl-4-[1,2,2,2-tetrafluoro-1-(trifluoromethyl)ethyl]phenyl]triazol-4-yl]-2-methylpyridine-3-carboxylate (1.11 g, 2.2 mmol), tetrahydrofuran (15 ml), sodium hydroxide (300 mg, 7.5 mmol) and 5 ml of water were combined in a 50 ml flask. The resulting solution was stirred at room temperature for 12 hours. This was followed by concentration under reduced pressure. The residue was taken up in some water and the pH of the solution was adjusted to a value of 3-4 by addition of 3 molar aqueous hydrochloric acid. The precipitate was filtered off and dried. This gave 849 mg of 5-[1-[2,6-dimethyl-4-[1,2,2,2-tetrafluoro-1-(trifluoromethyl)ethyl]phenyl]triazol-4-yl]-2-methylpyridine-3-carboxylic acid.

The following compounds were prepared analogously:
2-chloro-5-[1-[2,6-dimethyl-4-[1,2,2,2-tetrafluoro-1-(trifluoromethyl)ethyl]phenyl]triazol-4-yl]pyridine-3-carboxylic acid and as by-product:
5-[1-[2,6-dimethyl-4-[1,2,2,2-tetrafluoro-1-(trifluoromethyl)ethyl]phenyl]triazol-4-yl]-2-methoxypyridine-3-carboxylic acid
5-[1-[2,6-dichloro-4-[1,2,2,2-tetrafluoro-1-(trifluoromethyl)ethyl]phenyl]triazol-4-yl]-2-methylpyridine-3-carboxylic acid
2-chloro-5-[1-[2,6-dichloro-4-[1,2,2,2-tetrafluoro-1-(trifluoromethyl)ethyl]phenyl]triazol-4-yl]pyridine-3-carboxylic acid and as by-product:
5-[1-[2,6-dichloro-4-[1,2,2,2-tetrafluoro-1-(trifluoromethyl)ethyl]phenyl]triazol-4-yl]-2-methoxypyridine-3-carboxylic acid Step 3

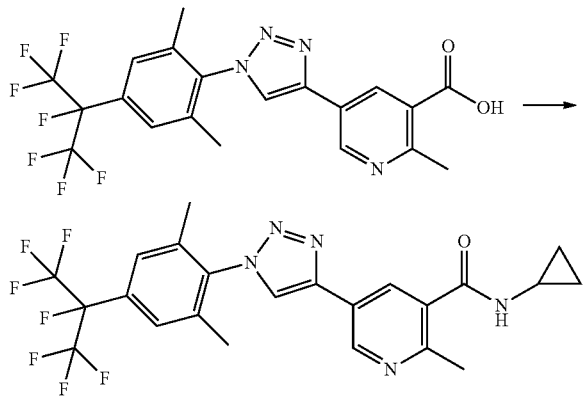

5-[1-[2,6-Dimethyl-4-[1,2,2,2-tetrafluoro-1-(trifluoromethyl)ethyl]phenyl]triazol-4-yl]-2-methylpyridine-3-carboxylic acid (481 mg, 1.01 mmol), dioxane (20 ml), cyclopropylamine (120 mg, 2.1 mmol), diisopropylethylamine (390 mg, 3 mmol) and 2,4,6-tripropyl-1,3,5,2,4,6-trioxatriphosphorinane 2,4,6-trioxide (1.0 ml of a 50% by weight strength solution in ethyl acetate, 1.68 mmol) were combined in a 50 ml three-necked flask. The resulting solution was stirred in an oil bath at 50° C. for 12 hours. This was followed by concentration under reduced pressure. The residue was extracted three times with in each case 20 ml of ethyl acetate and the combined organic phases were then washed once with saturated aqueous sodium chloride solution, dried with anhydrous sodium sulphate and concentrated under reduced pressure. The crude product was purified by preparative HPLC. This gave 113.9 mg of N-cyclopropyl-5-[1-[2,6-dimethyl-4-[1,2,2,2-tetrafluoro-1-(trifluoromethyl)ethyl]phenyl]triazol-4-yl]-2-methylpyridine-3-carboxamide.

HPLC-MS$^a$): log P=3.33, mass (m/z)=516 [M+H]+.

1H NMR (Bruker AV400, 400 MHz, d6-DMSO, ppm): δ 9.074 (s, 1H), 9.030-9.044 (d, 1H), 8.606-8.617 (d, 1H), 8.148-8.154 (d, 1H), 7.698 (s, 2H), 2.847-2.884 (m, 1H), 2.55 (s, 3H), 2.112 (s, 6H), 0.702-0.749 (m, 2H), 0.540-0.578 (m, 2H)

Synthesis of the Starting Materials

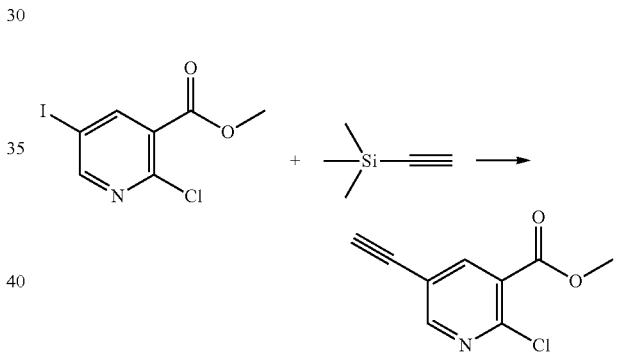

Methyl 2-chloro-5-iodopyridine-3-carboxylate (20 g, 67.23 mmol), triethylamine (200 ml), ethynyltrimethylsilane (8.0 g, 81.45 mmol), copper(I) iodide (3.0 g, 15.71 mmol), triphenylphosphine (4.3 g, 16.39 mmol) and bis(triphenylphosphine)palladium(II) dichloride (3.04 g, 4.33 mmol) were added to a 250 ml flask which had been vented and filled with nitrogen. The resulting solution was heated in an oil bath at 50° C. for 12 hours. Methanol (40 ml) and potassium carbonate (4.0 g, 28.9 mmol) were then added with stirring. The resulting solution was then stirred at room temperature for 2 hours. Undissolved solids were then filtered off. The filtrate was extracted three times with 50 ml of ethyl acetate each time, and the combined organic phases were washed with saturated aqueous sodium chloride solution. The organic phase was then dried with anhydrous sodium sulphate and concentrated under reduced pressure. The residue was chromatographed on a column using silica gel and petroleum ether/ethyl acetate 10:1 (v/v) as mobile phase. This gave 7.5 g of methyl 2-chloro-5-ethynylpyridine-3-carboxylate.

$^1$H NMR (Bruker AV-III, 300 MHz, CDCl$_3$, 25° C.): 8.70-8.71 (1H, d), 8.33-8.34 (1H, d), 4.68 (1H, s), 3.89 (3H, s).

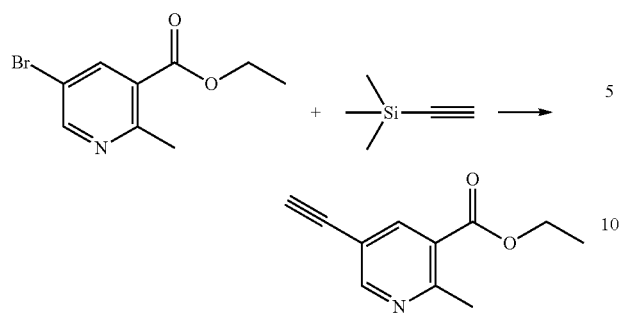

Ethyl 5-bromo-2-methylpyridine-3-carboxylate (20 g, 81.94 mmol), triethylamine (150 ml), ethynyltrimethylsilane (10.2 g, 103.85 mmol), copper(I) iodide (3.3 g, 17.32 mmol), triphenylphosphine (4.3 g, 16.39 mmol) and bis(triphenylphosphine)palladium(II) dichloride (3.1 g, 4.42 mmol) were added to a 250 ml flask which had been vented and filled with nitrogen. The resulting solution was heated in an oil bath at 50° C. for 12 hours. Methanol (100 ml) and potassium carbonate (4.0 g, 28.9 mmol) were then added with stirring. The resulting solution was then stirred at room temperature for 2 hours. Undissolved solids were then filtered off. The filtrate was extracted three times with 50 ml of ethyl acetate each time, and the combined organic phases were washed with saturated aqueous sodium chloride solution. The organic phase was then dried with anhydrous sodium sulphate and concentrated under reduced pressure. The residue was chromatographed on a column using silica gel and petroleum ether/ethyl acetate 10:1 (v/v) as mobile phase. This gave 3.5 g of ethyl 5-ethynyl-2-methylpyridine-3-carboxylate.

$^1$H NMR (Bruker AV-III, 300 MHz, CDCl$_3$, 25° C.): 8.70-8.71 (1H, d), 8.33-8.34 (1H, d), 4.68 (1H, s), 3.89 (3H, s).

Preparation of the starting material 4-heptafluoroisopropyl-2-methyl-6-trifluoromethylaniline Process 1

4-Heptafluoroisopropyl-2-methyl-6-trifluoromethylaniline can be prepared from 2-methyl-6-trifluoromethylaniline by the process indicated in the reaction scheme by reaction with heptafluoroisopropyl iodide in the presence of hydrogen peroxide. 2-Methyl-6-trifluoromethylaniline is known from the literature (John P. Chupp, Terry M. Balthazor, Michael J. Miller, and Mark J. Pozzo J. Org. Chem. 49 (1984), 4711-4716 or Thomas E. Nickson J. Org. Chem. 51 (1986) 3903-3904), and heptafluoroisopropyl iodide is commercially available.

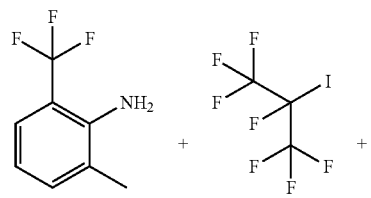

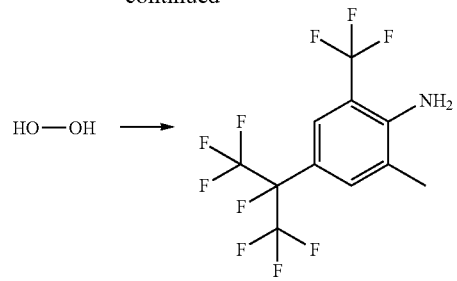

17.48 g (100 mmol) of 2-methyl-6-trifluoromethylaniline in 498 ml of dimethyl sulphoxide were initially charged in a three-necked flask, and 44.3 g (21.095 ml, 150 mmol) of 2-iodoheptafluoropropane, 29.9 ml (29.9 mmol) of 1 molar iron(II) sulphate solution in water and 5.43 ml (104 mmol) of 96% strength sulphuric acid were then added. The mixture was then degassed with argon, and using a syringe pump, 20.4 ml of 30% strength aqueous hydrogen peroxide solution were then added dropwise over a period of 15 minutes. The temperature increased to 54° C. Towards the end of the dropwise addition, the mixture was briefly heated to 60° C. The mixture was stirred without heating for another 20 minutes, during which time the temperature fell to 36° C. For work-up, the mixture was poured into saturated aqueous sodium bicarbonate solution and the product was extracted with ethyl acetate. The combined extracts were washed first with water and then with saturated aqueous sodium chloride solution, dried with sodium sulphate and concentrated on a rotary evaporator under reduced pressure. For purification, the residue was chromatographed in two protions on a column containing 120 g of silica gel and using a gradient from pure cyclohexane to cyclohexane/ethyl acetate 95:5 (v/v). This gave 18.9 g of 4-heptafluoroisopropyl-2-methyl-6-trifluoromethylaniline.

Analogously, 2-chloro-4-heptafluoroisopropyl-6-trifluoromethylaniline was also obtained from 2-chloro-6-trifluoromethylaniline and 2-iodoheptafluoropropane:

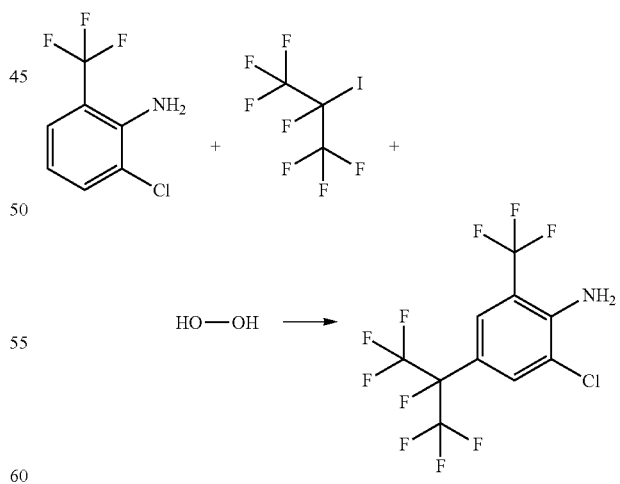

30 g (0.153 mol) of 2-chloro-6-trifluoromethylaniline (commercially available) were initially charged in 765 ml of dimethyl sulphoxide (DMSO) in a three-necked flask, and 68.1 g (0.23 mol) of 2-iodoheptafluoropropane, 46 ml of a 1 molar aqueous iron(II) sulphate solution and 15.4 g of 98% strength sulphuric acid were then added. The mixture was degassed with argon, and using a syringe pump, 34.8 g of 30% strength aqueous hydrogen peroxide solution were then added dropwise over a period of 30 minutes. During the addition, the temperature increased to 70° C. The mixture was stirred for another 20 minutes, during which time the temperature fell to 30° C. The reaction mixture was then poured into saturated aqueous sodium bicarbonate solution and extracted with ethyl acetate. The combined extracts were washed first with water, then with saturated aqueous bisulphite solution and saturated aqueous sodium chloride solution, dried with sodium sulphate and concentrated under reduced pressure on a rotary evaporator. For purification, the residue was chromatographed on a cartridge containing 330 g of silica gel and using a gradient from pure cyclohexane to 90:10 (v/v) cyclohexane/ethyl acetate. This gave 46.1 g of 2-chloro-4-heptafluoroisopropyl-6-trifluoromethylaniline.

Preparation of the starting material 4-heptafluoroisopropyl-2-methyl-6-trifluoromethylaniline Process 2

Furthermore, 4-heptafluoroisopropyl-2-methyl-6-trifluoromethylaniline can be prepared from 4-heptafluoroisopropyl-2-methylaniline, which is known from the literature (e.g. US2004/92762), by the process indicated in the scheme below by reacting sodium trifluoromethylsulphinate in the presence of oxidizing agents and transition metal catalysts.

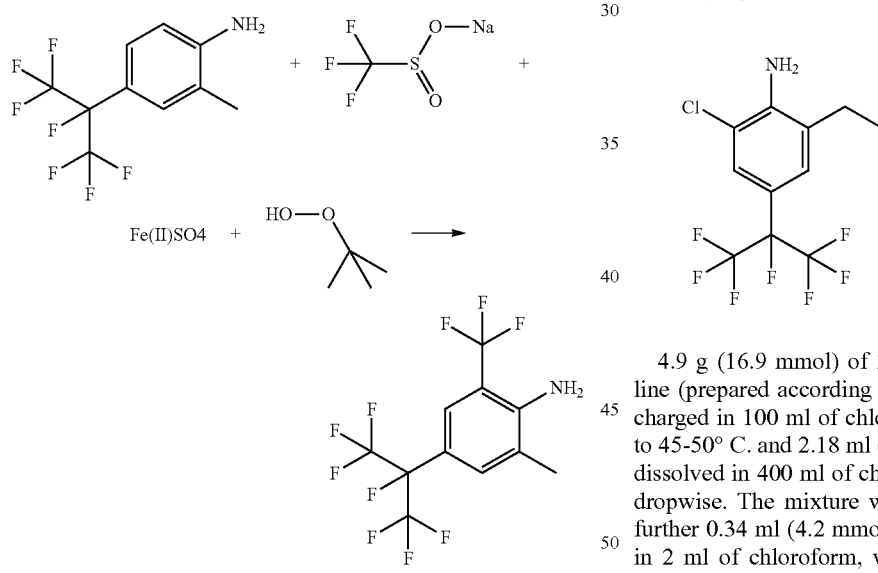

In a 1000 ml three-necked flask, 25 g (91 mmol) of 4-heptafluoroisopropyl-2-methylaniline were added to a mixture of 363.4 ml of water and 181.7 ml of acetonitrile. 27.3 ml (27.3 mmol) of aqueous 1 molar iron(II) sulphate solution and 31.19 g (200 mmol) of sodium trifluoromethylsulphinate were then added. The mixture was vented with argon and 35.1 g (273 mmol) of a 70% strength aqueous tert-butyl hydroperoxide solution were then metered in without cooling over a period of 4.5 hours using a syringe pump. The temperature increased to 34° C. After the addition had ended, the mixture was stirred for another 1 hour. For work-up, the mixture was poured into 425 ml of saturated aqueous sodium bisulphite solution and stirred for 15 minutes. 425 ml of saturated sodium bicarbonate solution were then added and the mixture was extracted three times with ethyl acetate. The combined organic phases were washed first with water and then with saturated aqueous sodium chloride solution, dried with sodium sulphate and concentrated on a rotary evaporator under reduced pressure. The crude product was chromatographed in two portions on a cartridge containing 120 g of silica gel and using a gradient with cyclohexane/ethyl acetate from 95:5 to 85:15 (v/v). This gave 19.5 g of 4-heptafluoroisopropyl-2-methyl-6-trifluoromethylaniline.

HPLC-MS$^a$): log P=4.67

GC/MS: mass (m/z)=343, retention time: 2.98 min, Kovacs index: 1089

(Agilent 6890 GC, HP5979 MSD, 10 m DB-1, iD=0.18 mm, FILM=0.4 µm, Inj.:250° C., const. flow: 1.6 mm/min He, Det.: MSD:280° C., FID: 320° C., oven:50° C. (1 min)–40° C./min–320° C. (3.25 min))

$^1$H-NMR (AV400, 400 MHz, d$_3$-acetonitrile): δ (ppm)=7.50 (s, 1 H), 7.48 (s, 1H), 5.03 (s, 2H, broad), 2.23 (s, 3 H).

Preparation of the starting material 2-chloro-6-ethyl-4-heptafluoroisopropylaniline The starting material 2-chloro-6-ethyl-4-heptafluoroisopropylaniline has hitherto not been described in the literature. It can be prepared from 2-ethyl-4-heptafluoroisopropylaniline, which is known from the literature (e.g. US2002/198399), by known chlorinating processes.

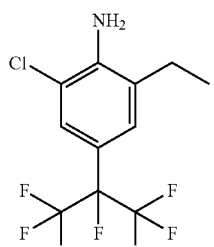

4.9 g (16.9 mmol) of 2-ethyl-4-heptafluoroisopropylaniline (prepared according to US2002/198399) were initially charged in 100 ml of chloroform, the solution was warmed to 45-50° C. and 2.18 ml (26.7 mmol) of sulphuryl chloride, dissolved in 400 ml of chloroform, were then slowly added dropwise. The mixture was stirred at 50° C. overnight, a further 0.34 ml (4.2 mmol) of sulphuryl chloride, dissolved in 2 ml of chloroform, was then added dropwise and the mixture was stirred at 50° C. for a further 3 hours. Thereafter, the mixture was cooled and the solvent was drawn off on a rotary evaporator under reduced pressure. The residue was taken up in dichloromethane, washed first with sodium bisulphite and then with dilute aqueous sodium hydroxide solution and dried with sodium sulphate, and the solvent was distilled off under reduced pressure on a rotary evaporator. For purification, the residue was chromatographed on a cartridge containing 120 g of silica gel and using a gradient from pure cyclohexane to 90:10 (v/v) cyclohexane/ethyl acetate. This gave 4.25 g of 2-chloro-6-ethyl-4-heptafluoroisopropylaniline.

HPLC-MS$^a$): log P=4.67, mass (m/z)=324 [M+H]+.

$^1$H-NMR (AV400, 400 MHz, d$_3$-acetonitrile): δ (ppm)=7.84 (s, 1 H), 7.82 (s, 1H), 7.53-7.56 (s, 2H, broad), 2.37 (q, J=7.6 Hz, 2 H), 1.06 (t, J=7.6 Hz, 3 H).

Preparation of the starting material 2-bromo-6-methyl-4-heptafluoroisopropylaniline The starting material 2-bromo-6-ethyl-4-heptafluoroisopropylaniline has hitherto not been described in the literature. It can be prepared from 2-methyl-4-heptafluoroisopropylaniline, which is known from the literature (e.g. US2002/92762), by known brominating processes (e.g. EP2319830, p. 327).

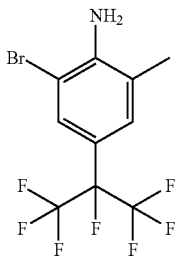

3.4 g (12.356 mmol) of 2-methyl-4-heptafluoroisopropylaniline were dissolved in 27 ml of dimethylformamide, 2.44 g (13.6 mmol) of N-bromosuccinimide were then added and the mixture was stirred at 60° C. for 1 hour. The mixture was cooled, water was added and the mixture was extracted three times with in each case 15 ml of n-hexane. The combined organic phases were washed with water, dried with sodium sulphate and concentrated on a rotary evaporator under reduced pressure. Chromatography on a 120 g cartridge containing silica gel and using a gradient from pure cyclohexane to cyclohexane/ethyl acetate 90:10 (v/v) gave 2.44 g of 2-bromo-6-ethyl-4-heptafluoroisopropylaniline.

HPLC-MS$^a$): log P=4.38, mass (m/z)=354 [M+H]+.

$^1$H-NMR (AV400, 400 MHz, d$_3$-acetonitrile): δ (ppm)=7.51 (s, 1 H), 7.23 (s, 1H), 4.86 (s, 2H, broad), 2.23 (s, 3 H).

The compounds listed in Table 1 were prepared using the preparation processes described above.

TABLE 1

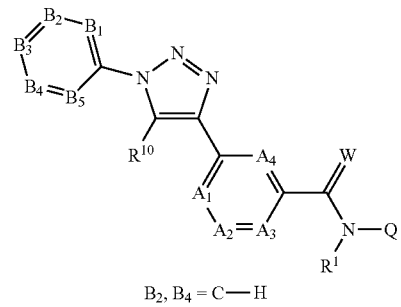

$B_2, B_4 = C-H$

| Ex. No. | $B_1$ | $B_3$ | $B_5$ | $R^1$ | $R^{10}$ | $A_1$ | $A_2$ | $A_3$ | $A_4$ | W | Q | logP$^{a)}$ | mass [m/z] $^{a)1)}$ |
|---|---|---|---|---|---|---|---|---|---|---|---|---|---|
| 1 | C—CH$_3$ | C-i-C$_3$F$_7$ | C—CH$_3$ | H | H | C—H | N | C—CH$_3$ | C—H | O | cyclopropyl | 3.3 | 516 |
| 2 | C—CH$_3$ | C-i-C$_3$F$_7$ | C—CH$_3$ | H | H | C—H | N | C—CH$_3$ | C—H | O | cyclopropyl | 3.8 | 536 |
| 3 | C—Cl | C-i-C$_3$F$_7$ | C—Cl | H | H | C—H | N | C—Cl | C—H | O | cyclopropyl | 3.9 | 576 |
| 4 | C—Cl | C-i-C$_3$F$_7$ | C—Cl | H | H | C—H | N | C—OCH$_3$ | C—H | O | 1-(cyano)cyclopropyl | 4.3 | 597 |
| 5 | C—Cl | C-i-C$_3$F$_7$ | C—Cl | H | H | C—H | N | C—CH$_3$ | C—H | O | cyclopropyl | 3.4 | 556 |
| 6 | C—Cl | C-i-C$_3$F$_7$ | C—Cl | H | H | C—H | N | C—CH$_3$ | C—H | O | 1-(cyano)cyclopropyl | 3.5 | 581 |
| 7 | C—CH$_3$ | C-i-C$_3$F$_7$ | C—CH$_3$ | H | H | C—H | N | C—OCH$_3$ | C—H | O | 1-(cyano)cyclopropyl | 4.2 | 557 |
| 8 | C—CH$_3$ | C-i-C$_3$F$_7$ | C—CH$_3$ | H | H | C—H | N | C—Cl | C—H | O | 1-(cyano)cyclopropyl | 3.8 | 561 |
| 9 | C—Cl | C-i-C$_3$F$_7$ | C—Cl | H | H | C—H | N | C—Cl | C—H | O | 1-(cyano)cyclopropyl | 3.8 | 601 |
| 10 | C—Cl | C-i-C$_3$F$_7$ | C—Cl | H | H | C—H | N | C—OCH$_3$ | C—H | O | cyclopropyl | 4.4 | 572 |
| 11 | C—CH$_3$ | C-i-C$_3$F$_7$ | C—CH$_3$ | H | H | C—H | N | C—OCH$_3$ | C—H | O | cyclopropyl | 4.3 | 532 |
| 12 | C—CH$_3$ | C-i-C$_3$F$_7$ | C—CH$_3$ | H | H | C—H | N | C—CH$_3$ | C—H | O | 1-(cyano)cyclopropyl | 3.4 | 541 |
| 13 | C—CF$_3$ | C-i-C$_3$F$_7$ | C—CH$_3$ | H | H | C—H | N | C—Cl | C—H | O | cyclopropyl | 3.9 | 590 |
| 14 | C—CF$_3$ | C-i-C$_3$F$_7$ | C—CH$_3$ | H | H | C—H | N | C—Cl | C—H | O | 1-(cyano)cyclopropyl | 3.9 | 615 |
| 15 | C—CF$_3$ | C-i-C$_3$F$_7$ | C—CH$_3$ | CH$_3$ | H | C—H | N | C—Cl | C—H | O | cyclopropyl | 4.3 | 604 |
| 16 | C—CF$_3$ | C-i-C$_3$F$_7$ | C—Cl | H | H | C—H | N | C—Cl | C—H | O | cyclopropyl | 4.0 | 610 |
| 17 | C—CF$_3$ | C-i-C$_3$F$_7$ | C—Cl | H | H | C—H | N | C—Cl | C—H | O | 1-(cyano)cyclopropyl | 3.9 | 635 |
| 18 | C—CH$_3$ | C-i-C$_3$F$_7$ | C—I | H | H | C—H | N | C—Cl | C—H | O | isopropyl | 4.2 | 602 |
| 19 | C—C$_2$H$_5$ | C-i-C$_3$F$_7$ | C—CH$_3$ | CH$_3$ | H | C—H | N | C—Cl | C—H | O | cyclopropyl | 4.6 | 564 |
| 20 | C—C$_2$H$_5$ | C-i-C$_3$F$_7$ | C—CH$_3$ | H | H | C—H | N | C—Cl | C—H | O | cyclopropyl | 4.1 | 550 |
| 21 | C—CH$_3$ | C-i-C$_3$F$_7$ | C—Br | CH$_3$ | H | C—H | N | C—Cl | C—H | O | cyclopropyl | 4.4 | 614 |
| 22 | C—CH$_3$ | C-i-C$_3$F$_7$ | C—Br | H | H | C—H | N | C—Cl | C—H | O | cyclopropyl | 3.9 | 600 |
| 23 | C—C$_2$H$_5$ | C-i-C$_3$F$_7$ | C—CH$_3$ | H | H | C—H | N | C—Cl | C—H | O | CH$_2$CF$_3$ | 4.5 | 592 |
| 24 | C—C$_2$H$_5$ | C-i-C$_3$F$_7$ | C—CH$_3$ | H | H | C—H | N | C—Cl | C—H | O | isopropyl | 4.4 | 552 |
| 25 | C—C$_2$H$_5$ | C-i-C$_3$F$_7$ | C—CH$_3$ | H | H | C—H | N | C—Cl | C—H | O | C$_2$H$_5$ | 4.1 | 538 |
| 26 | C—CH$_3$ | C-i-C$_3$F$_7$ | C—Br | H | H | C—H | N | C—Cl | C—H | O | CH$_2$CF$_3$ | 4.3 | 642 |
| 27 | C—CH$_3$ | C-i-C$_3$F$_7$ | C—Br | H | H | C—H | N | C—Cl | C—H | O | C$_2$H$_5$ | 3.9 | 588 |
| 28 | C—Cl | C—Ph | C—Cl | H | H | C—H | N | C—Cl | C—H | O | CH$_2$CF$_3$ | 3.9 | 526 |
| 29 | C—Cl | C—Ph | C—Cl | H | H | C—H | N | C—Cl | C—H | O | isopropyl | 3.8 | 486 |
| 30 | C—Cl | C—Ph | C—Cl | H | H | C—H | N | C—Cl | C—H | O | C$_2$H$_5$ | 3.5 | 472 |
| 31 | C—Cl | C—Ph | C—Cl | CH$_3$ | H | C—H | N | C—Cl | C—H | O | cyclopropyl | 4.0 | 498 |
| 32 | C—Cl | C—Ph | C—Cl | H | H | C—H | N | C—Cl | C—H | O | cyclopropyl | 3.5 | 484 |
| 33 | C—OCF$_3$ | C-i-C$_3$F$_7$ | C—Cl | H | H | C—H | N | C—Cl | C—H | O | cyclopropyl | 4.1 | 626 |
| 34 | C—OCF$_3$ | C-i-C$_3$F$_7$ | C—Cl | H | H | C—H | N | C—Cl | C—H | O | 1-(cyano)cyclopropyl | 4.0 | 651 |

TABLE 1-continued

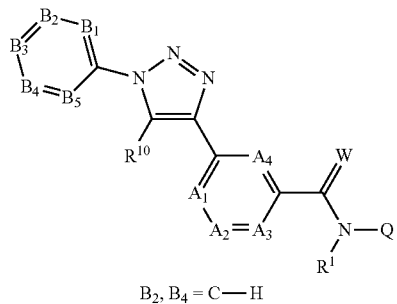

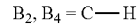

| Ex. No. | B₁ | B₃ | B₅ | R¹ | R¹⁰ | A₁ | A₂ | A₃ | A₄ | W | Q | logP$^{a)}$ | mass [m/z] $^{a)1)}$ |
|---|---|---|---|---|---|---|---|---|---|---|---|---|---|
| 35 | C—OCF₃ | C-i-C₃F₇ | C—Cl | CH₃ | H | C—H | N | C—Cl | C—H | O | cyclopropyl | 4.6 | 640 |
| 36 | C—OCHF₂ | C-i-C₃F₇ | C—Cl | H | H | C—H | N | C—Cl | C—H | O | cyclopropyl | 3.7 | 608 |
| 37 | C—OCHF₂ | C-i-C₃F₇ | C—Cl | CH₃ | H | C—H | N | C—Cl | C—H | O | cyclopropyl | 4.2 | 622 |
| 38 | C—OCHF₂ | C-i-C₃F₇ | C—Cl | H | H | C—H | N | C—Cl | C—H | O | 1-(cyano)cyclopropyl | 3.7 | 633 |

$^1$The stated mass is the peak of the isotope pattern of the [M + H]⁺ ion of the highest intensity; if the [M − H]⁻ ion was detected, the stated mass is identified with 2.
$^2$The stated mass is the peak of the isotope pattern of the [M + H]⁻ ion of the highest intensity.
$^{a)}$Note regarding the determination of the logP values and mass detection: The determination of the given logP values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase
A: acetonitrile (0.1% formic acid); mobile phase
B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is effected by means of an Agilend MSD system.

NMR Data of Selected Examples
NMR Peak List Method

The 1H NMR data of selected examples are stated in the form of 1H NMR peak lists. For each signal peak, first the δ value in ppm and then the signal intensity in round brackets are listed. The δ value—signal intensity—number pairs for different signal peaks are listed with separation from one another by semicolons.

The peak list for one example therefore takes the form of: $\delta_1$ (intensity$_1$); $\delta_2$ (intensity$_2$); . . . , $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of the 1H NMR spectra we use tetramethylsilane and/or the chemical shift of the solvent, particularly in the case of spectra measured in DMSO. Therefore, the tetramethylsilane peak may, but need not, occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject matter of the invention, and/or peaks of impurities.

In the reporting of compound signals in the delta range of solvents and/or water, our lists of 1H NMR peaks show the usual solvent peaks, for example peaks of DMSO in DMSO-D₆ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

Example 1

$^1$H-NMR (400.0 MHz, d₆-DMSO): δ=9.074 (4.6); 9.044 (2.0); 9.039 (2.1); 8.617 (1.0); 8.606 (1.0); 8.154 (2.0); 8.148 (2.0); 7.698 (3.7); 4.448 (0.4); 3.904 (4.4); 3.388 (9.7); 3.31 (0.7); 3.364 (0.8); 3.333 (42.6); 3.168 (0.4); 2.884 (0.4); 2.815 (0.7); 2.865 (0.7); 2.856 (0.4); 2.847 (0.3); 2.616 (0.4); 2.671 (0.5); 2.661 (0.4); 2.550 (8.9); 2.525 (1.5); 2.520 (2.4); 2.51 1 (31.1); 2.507 (63.6); 2.502 (84.9); 2.498 (64.1); 2.493 (32.7); 2.334 (0.4); 2.329 (0.5); 2.325 (0.4); 2.1 12 (16.0); 0.813 (0.4); 0.749 (0.5); 0.73 (1.2); 0.731 (1.8); 0.719 (1.6); 0.714 (1.4); 0.702 (0.6); 0.578 (0.6); 0.568 (1.7); 0.562 (1.5); 0.558 (1.5); 0.552 (1.4); 0.540 (0.4); 0.000 (0.4)

Example 2

1H-NMR (400.0 MHz, d₆-DMSO): δ=9.128 (4.1); 9.018 (2.2); 9.012 (2.2); 8.769 (1.2); 8.758 (1.2); 8.329 (2.2); 8.323 (2.2); 7.704 (4.0); 4.451 (0.4); 3.904 (2.7); 3.395 (1.0); 3.388 (0.9); 3.381 (1.1); 3.335 (151 0.7); 2.813 (0.5); 2.864 (0.7); 2.854 (0.7); 2.845 (0.5); 2.836 (0.4); 2.616 (0.5); 2.612 (0.6); 2.668 (0.5); 2.507 (75.3); 2.502 (98.1); 2.498 (76.8); 2.329 (0.6); 2.325 (0.5); 2.1 14 (16.0); 0.765 (0.4); 0.752 (1.3); 0.748 (1.8); 0.735 (1.7); 0.730 (1.4); 0.718 (0.6); 0.576 (0.6); 0.565 (1.7); 0.559 (1.7); 0.550 (1.5); 0.537 (0.4)

Example 3

¹H-NMR (400.0 MHz, d₆-DMSO): δ=9.272 (1 1.9); 9.040 (6.2); 9.034 (6.1); 8.769 (3.4); 8.758 (3.4); 8.364 (6.4); 8.358 (6.1); 8.219 (16.0); 3.904 (5.2); 3.395 (1.1); 3.340 (389.8); 3.174 (1.1); 3.162 (1.1); 2.892 (0.4); 2.882 (1.0); 2.873 (1.5); 2.864 (2.1); 2.854 (2.1); 2.846 (1.5); 2.838 (1.0); 2.827 (0.4); 2.672 (1.2); 2.507 (155.4); 2.503 (191 0.9); 2.499 (144.9); 2.334 (0.9); 2.330 (1.2); 0.766 (1.3); 0.752 (4.1); 0.748 (5.2); 0.735 (5.0); 0.730 (4.2); 0.718 (1.6); 0.580 (1.7); 0.569 (5.2); 0.563 (5.2); 0.554 (4.5); 0.542 (1.3); 0.000 (0.5)

Example 4

¹H-NMR (400.0 MHz, d₆-DMSO): δ=9.175 (7.0); 9.158 (3.3); 8.889 (3.4); 8.883 (3.5); 8.548 (3.7); 8.542 (3.6); 8.211 (7.9); 4.465 (0.4); 4.452 (1.2); 4.438 (0.4); 4.024 (16.0); 3.904 (5.1); 3.395 (3.0); 3.388 (2.1); 3.382 (3.1); 3.336 (204.7); 2.616 (0.5); 2.672 (0.7); 2.661 (0.5); 2.542 (0.4); 2.525 (2.2); 2.512 (46.2); 2.507 (89.7); 2.503 (116.1); 2.498 (86.1); 2.494 (43.6); 2.334 (0.5); 2.330 (0.7); 2.325 (0.5); 1.611 (1.2); 1.597 (2.9); 1.590 (3.1); 1.577 (1.4); 1.336 (1.5); 1.323 (3.0); 1.316 (3.2); 1.301 (1.2); 1.235 (0.3); 0.000 (0.4)

Example 5

¹H-NMR (400.0 MHz, d₆-DMSO): δ=9.213 (9.3); 9.056 (3.7); 9.051 (3.9); 8.630 (1.9); 8.619 (2.0); 8.214 (9.9); 8.165 (3.7); 8.160 (3.8); 4.465 (0.5); 4.451 (1.3); 4.437 (0.5); 3.904 (4.0); 3.395 (3.0); 3.388 (2.0); 3.382 (3.0); 3.336 (129.7); 3.175 (0.6); 3.162 (0.6); 2.894 (0.6); 2.885 (0.8); 2.876 (1.3); 2.866 (1.3); 2.857 (0.8); 2.848 (0.6); 2.616 (0.4); 2.672 (0.6); 2.661 (0.4); 2.562 (16.0); 2.539 (0.4); 2.525 (1.8); 2.520 (2.6); 2.512 (34.1); 2.507 (69.7); 2.503 (92.9); 2.498 (70.4); 2.494 (36.1); 2.334 (0.4); 2.329 (0.6); 2.325 (0.4); 0.750 (0.8); 0.737 (2.2); 0.732 (3.2); 0.720 (2.9); 0.714 (2.5); 0.703 (1.1); 0.582 (1.1); 0.571 (3.1); 0.565 (2.8); 0.561 (2.7); 0.55 (2.6); 0.53 (0.8); 0.000 (0.5)

Example 6

¹H-NMR (400.0 MHz, d₆-DMSO): δ=9.514 (4.3); 9.230 (8.3); 9.098 (3.7); 9.093 (3.8); 8.272 (3.7); 8.26 (3.7); 8.215 (10.4); 4.50 (0.4); 4.463 (2.6); 4.449 (7.4); 4.436 (2.8); 3.904 (8.7); 3.482 (0.5); 3.469 (0.5); 3.418 (0.4); 3.407 (0.8); 3.394 (16.8); 3.381 (11.7); 3.381 (16.8); 3.310 (1.7); 3.364 (1.3); 3.332 (178.3); 3.174 (0.9); 3.161 (0.9); 2.616 (0.9); 2.611 (1.3); 2.661 (1.0); 2.583 (16.0); 2.541 (0.9); 2.507 (150.8); 2.502 (198.9); 2.498 (153.5); 2.457 (0.5); 2.333 (0.9); 2.329 (1.2); 2.325 (1.0); 1.615 (1.5); 1.600 (3.7); 1.593 (4.0); 1.580 (1.7); 1.346 (1.8); 1.333 (3.9); 1.326 (4.1); 1.312 (1.5); 1.299 (0.4); 0.891 (0.6); 0.813 (1.2); 0.855 (0.6); 0.000 (0.8)

Example 7

1H-NMR (400.0 MHz, d₆-DMSO): δ=9.149 (2.2); 9.029 (4.3); 8.815 (2.1); 8.869 (2.2); 8.555 (2.3); 8.549 (2.2); 7.694 (3.8); 4.018 (10.3); 3.904 (3.3); 3.344 (258.7); 2.676 (0.4); 2.672 (0.6); 2.668 (0.5); 2.543 (0.6); 2.512 (3.0); 2.508 (1.3); 2.503 (92.5); 2.499 (69.3); 2.334 (0.4); 2.330 (0.6); 2.326 (0.4); 2.117 (16.0); 1.612 (0.8); 1.597 (2.0); 1.590 (2.1); 1.517 (0.9); 1.331 (1.0); 1.318 (2.0); 1.31 1 (2.1); 1.297 (0.8)

Example 8

¹H-NMR (400.0 MHz, d₆-DMSO): δ=9.677 (2.3); 9.143 (4.8); 9.058 (2.4); 9.052 (2.5); 8.441 (2.5); 8.435 (2.4); 7.704 (3.7); 4.467 (1.6); 4.453 (4.5); 4.440 (1.7); 3.904 (6.2); 3.469 (0.4); 3.419 (0.3); 3.407 (0.7); 3.395 (11.2); 3.388 (7.4); 3.382 (10.9); 3.370 (1.8); 3.340 (224.0); 3.175 (0.4); 3.162 (0.4); 2.676 (0.5); 2.672 (0.6); 2.667 (0.5); 2.542 (0.5); 2.525 (2.0); 2.512 (38.5); 2.507 (74.7); 2.503 (96.4); 2.498 (70.7); 2.494 (34.8); 2.334 (0.4); 2.330 (0.6); 2.325 (0.4); 2.115 (16.0); 1.643 (0.8); 1.629 (1.9); 1.622 (2.0); 1.609 (0.9); 1.332 (1.0); 1.318 (2.1); 1.312 (2.1); 1.297 (0.9); 0.892 (0.4); 0.873 (0.7); 0.855 (0.4)

Example 9

¹H-NMR (400.0 MHz, d₆-DMSO): δ=9.668 (6.9); 9.282 (14.5); 9.081 (7.1); 9.075 (7.2); 8.483 (1.3); 8.477 (7.2); 8.219 (16.0); 4.553 (0.4); 4.467 (3.7); 4.453 (10.5); 4.439 (3.9); 3.904 (1 1.9); 3.483 (0.6); 3.469 (0.7); 3.456 (0.4); 3.418 (0.6); 3.408 (1.2); 3.395 (25.8); 3.388 (17.1); 3.382 (25.4); 3.371 (2.9); 3.340 (363.8); 3.175 (1.2); 3.162 (1.1); 2.676 (0.9); 2.672 (1.3); 2.668 (0.9); 2.542 (0.8); 2.525 (3.4); 2.512 (14.6); 2.507 (149.3); 2.503 (196.5); 2.498 (145.7); 2.494 (72.9); 2.334 (0.9); 2.330 (1.2); 2.325 (0.9); 1.640 (2.3); 1.625 (5.6); 1.618 (6.0); 1.605 (2.6); 1.470 (0.3); 1.340 (2.8); 1.321 (5.6); 1.320 (6.3); 1.306 (2.3); 1.235 (0.4); 0.892 (0.7); 0.873 (1.5); 0.855 (0.8); 0.000 (0.7)

Example 10

¹H-NMR (400.0 MHz, d₆-DMSO): δ=9.157 (6.7); 8.836 (3.4); 8.830 (3.4); 8.461 (3.6); 8.45 (3.5); 8.326 (1.4); 8.315 (1.4); 8.209 (1.9); 4.003 (16.0); 3.904 (4.7); 3.338 (198.2); 3.175 (0.8); 3.162 (0.8); 2.891 (0.5); 2.881 (0.7); 2.873 (1.1); 2.863 (1.1); 2.854 (0.7); 2.844 (0.5); 2.616 (0.5); 2.612 (0.7); 2.681 (0.5); 2.542 (0.7); 2.512 (46.6); 2.507 (89.6); 2.503 (1 16.1); 2.498 (81.2); 2.334 (0.5); 2.330 (0.7); 2.325 (0.5); 0.755 (0.7); 0.742 (1.8); 0.737 (2.6); 0.725 (2.4); 0.719 (2.0); 0.707 (0.9); 0.602 (0.9); 0.592 (2.6); 0.585 (2.3); 0.582 (2.2); 0.56 (2.1); 0.564 (0.6); 0.000 (0.3)

Example 11

¹H-NMR (400.0 MHz, d₆-DMSO): δ=9.012 (4.7); 8.822 (2.4); 8.816 (2.5); 8.471 (2.5); 8.465 (2.4); 8.315 (0.9); 8.304 (1.0); 7.692 (3.8); 3.998 (11.2); 3.904 (2.7); 3.332 (55.2); 3.1 75 (0.8); 3.162 (0.8); 2.891 (0.3); 2.881 (0.5); 2.872 (0.7); 2.862 (0.7); 2.854 (0.5); 2.844 (0.4); 2.612 (0.3); 2.525 (1.1); 2.512 (20.3); 2.507 (40.0); 2.503 (52.5); 2.498 (39.3); 2.494 (19.9); 2.329 (0.3); 2.1 15 (16.0); 0.754 (0.5); 0.741 (1.2); 0.736 (1.8); 0.724 (1.6); 0.718 (1.1); 0.706 (0.6); 0.600 (0.6); 0.590 (1.8); 0.583 (1.5); 0.579 (1.5); 0.574 (1.4); 0.561 (0.4)

Example 12

¹H-NMR (400.0 MHz, d₆-DMSO): δ=9.509 (2.3); 9.094 (4.4); 9.085 (2.0); 9.080 (2.0); 8.255 (1.9); 8.250 (1.9); 7.700 (3.8); 4.463 (1.1); 4.450 (3.3); 4.436 (1.2); 3.904 (4.3); 3.395 (6.9); 3.388 (5.0); 3.381 (6.7); 3.370 (0.8); 3.364 (0.6); 3.332 (105.1); 3.174 (0.4); 3.161 (0.4); 2.675 (0.5); 2.61 (0.6); 2.667 (0.5); 2.570 (8.5); 2.542 (0.5); 2.524 (1.9); 2.507 (77.0); 2.502 (98.2); 2.498 (72.1); 2.333 (0.4); 2.329 (0.6); 2.325 (0.4); 2.114 (16.0); 1.617 (0.8); 1.603

(2.0); 1.596 (2.1); 1.583 (0.9); 1.341 (1.0); 1.328 (2.0); 1.321 (2.1); 1.306 (0.8); 0.813 (0.5); 0.000 (0.4)

Example 13

$^1$H-NMR (400.0 MHz, CD3CN): δ=9.017 (0.4); 9.011 (0.4); 8.988 (11.8); 8.982 (11.7); 8.484 (16.0); 8.334 (13.5); 8.328 (13.1); 8.077 (8.4); 8.022 (8.6); 7.080 (3.0); 5.447 (0.4); 4.086 (1.6); 4.068 (4.8); 4.050 (4.8); 4.032 (1.6); 2.895 (0.7); 2.885 (2.1); 2.816 (3.1); 2.861 (4.6); 2.857 (4.7); 2.849 (3.1); 2.839 (2.2); 2.830 (0.8); 2.461 (0.4); 2.462 (0.5); 2.457 (0.4); 2.147 (122.9); 2.124 (51.3); 2.107 (1.5); 2.101 (1.0); 2.095 (0.6); 2.086 (1.0); 1 971 (21.5); 1.964 (5.6); 1.958 (14.4); 1.952 (68.9); 1.948 (124.1); 1.940 (164.6); 1.933 (115.1); 1.921 (59.4); 1.780 (0.4); 1.774 (0.8); 1.768 (1.0); 1.762 (0.7); 1.756 (0.4); 1.431 (10.8); 1.210 (3.6); 1.221 (5.6); 1.204 (11.0); 1.186 (5.5); 0.881 (0.5); 0.813 (2.5); 0.800 (7.9); 0.795 (10.1); 0.782 (10.6); 0.777 (7.8); 0.765 (3.4); 0.743 (0.5); 0.725 (0.5); 0.674 (0.4); 0.664 (0.4); 0.634 (3.3); 0.623 (9.0); 0.617 (9.7); 0.613 (8.7); 0.608 (8.2); 0.595 (2.4); 0.553 (0.4); 0.550 (0.4); 0.540 (0.4); 0.146 (0.7); 0.008 (6.8); 0.000 (162.6);-.008 (8.8); −0.150 (0.8)

Example 14

$^1$H-NMR (400.0 MHz, CD3CN): δ=9.033 (11.1); 9.021 (11.0); 8.497 (16.0); 8.404 (12.1); 8.398 (11.6); 8.079 (8.2); 8.024 (8.4); 7.737 (4.8); 5.447 (0.7); 4.086 (2.3); 4.068 (6.9); 4.051 (7.0); 4.033 (2.4); 2.355 (0.4); 2.330 (0.5); 2.281 (0.9); 2.218 (0.7); 2.150 (197.9); 2.126 (56.0); 2.107 (3.1); 2.101 (2.2); 2.095 (1.6); 2.081 (3.5); 1.972 (30.8); 1.964 (6.3); 1.958 (16.3); 1.952 (75.5); 1.946 (134.9); 1.940 (178.1); 1.934 (124.2); 1.928 (64.1); 1.808 (0.3); 1.781 (0.5); 1.774 (0.9); 1.768 (1.1); 1.762 (0.8); 1.756 (0.5); 1.651 (0.3); 1.613 (4.7); 1.598 (12.6); 1.592 (12.5); 1.578 (6.3); 1.538 (0.8); 1.431 (1.4); 1.432 (0.9); 1.392 (6.4); 1.318 (12.6); 1.371 (12.8); 1.357 (4.7); 1.319 (0.4); 1.285 (0.4); 1.211 (1.2); 1.222 (8.1); 1.204 (15.8); 1.186 (7.9); 1.152 (3.1); 1.140 (9.4); 1.132 (9.5); 1.121 (4.1); 1.081 (0.6); 0.980 (0.5); 0.940 (4.1); 0.929 (9.3); 0.922 (9.3); 0.909 (3.0); 0.146 (0.6); 0.000 (140.9); −0.149 (0.7)

Example 15

$^1$H-NMR (400.0 MHz, CD3CN): δ=8.979 (3.2); 8.974 (3.0); 8.473 (5.0); 8.290 (3.0); 8285 (2.8); 8.229 (0.4); 8.077 (3.3); 8.023 (3.3); 406 0.6); 4.050 (0.6); 3.077 (16.0); 2.821 (2.7); 2.809 (0.4); 2.797 (0.8); 2.791 (0.9); 2.782 (1.4); 2.771 (0.9); 2.764 (0.7); 2.754 (0.4); 2.464 (0.4); 2.410 (0.3); 2.149 (221.2); 2.128 (15.8); 2.107 (1.1); 2.101 (0.7); 2.095 (0.5); 2.086 (0.4); 2.026 (0.4); 1.972 (3.6); 1.952 (60.1); 1.946 (102.5); 1.940 (121.2); 1.934 (90.5); 1.928 (46.9); 1.780 (0.3); 1.774 (0.6); 1.768 (0.7); 1.762 (0.5); 1.437 (0.5); 1.349 (1.2); 1.271 (0.6); 1.222 (0.7); 1.204 (1.3); 1.186 (0.7); 0.857 (0.5); 0.843 (0.5); 0.801 (0.7); 0.591 (2.5); 0.549 (2.6); 0.533 (2.3); 0.000 (72.0); −0.150 (0.3)

Example 16

$^1$H-NMR (400.0 MHz, CD3CN): δ=8.997 (1.5); 8.991 (1.5); 8.530 (2.0); 8.345 (1.8); 8.339 (1.6); 8.290 (1.1); 8.128 (1.1); 7.052 (0.4); 2.876 (0.4); 2.867 (0.6); 2.857 (0.6); 2.849 (0.4); 2.134 (65.1); 2.1 13 (0.9); 2.106 (1.0); 2.100 (0.6); 2.094 (0.4); 1.963 (4.7); 1.957 (12.0); 1.951 (58 2); 1.945 (106.4); 1.939 (141.7); 1.933 (97.6); 1.927 (50.0); 1.774 (0.6); 1.767 (0.8); 1.761 (0.6); 1.437 (16.0); 1.270 (0.9); 0.813 (0.3); 0.800 (1.0); 0.795 (1.3); 0.783(1.3); 0.777 (1.0); 0.765 (0.4); 0.635 (0.4); 0.625 (1.1); 0.617 (1.2); 0.609 (1.0); 0.596 (0.4); 0.146 (2.0); 0.031 (0.5); 0.030 (0.5); 0.028 (0.5); 0.027 (0.5); 0.024 (0.5); 0.008 (20.4); 0.000 (427.2); −0.009 (18.9); −0.150 (1.9)

Example 17

$^1$H-NMR (400.0 MHz, CD3CN): δ=9.042 (10.1); 9.036 (10.3); 8.557 (0.5); 8.544 (14.2); 8.413 (11.2); 8.407 (11.1); 8.290 (6.9); 8.129 (6.9); 7.703 (3.2); 5.446 (1.0); 4.086 (1.2); 4.068 (3.6); 4.050 (3.7); 4.032 (1.2); 2.132 (59.0); 2.1 13 (1.1); 2.107 (1.2); 2.100 (0.9); 2.094 (0.5); 2.086 (0.4); 1.971 (16.8); 1.964 (5.5); 1.957 (13.0); 1.952 (72.1); 1.945 (131.8); 1.939 (179.1); 1.933 (124.6); 1.927 (64.4); 1.780 (0.4); 1.774 (0.7); 1.768 (1.0); 1.762 (0.7); 1.755 (0.4); 1.612 (4.2); 1.598 (10.4); 1.591 (10.5); 1.577 (5.6); 1.537 (0.7); 1.437 (16.0); 1.391 (5.9); 1.377 (10.5); 1.310 (11.0); 1.356 (4.3); 1.319 (0.3); 1.285 (0.5); 1.270 (2.7); 1.221 (4.6); 1.204 (8.9); 1.186 (4.5); 0.881 (0.4); 0.146 (2.3); 0.008 (19.5); 0.000 (548.9); −0.009 (23.0); −0.031 (0.4); −0.150 (2.4)

Example 18

$^1$H-NMR (400.0 MHz, d$_6$-DMSO): δ=9.228 (6.8); 9.029 (3.5); 9.023 (3.6); 8.598 (1.9); 8.579 (1.9); 8.317 (3.7); 8.311 (3.7); 8.056 (3.2); 7.950 (3.0); 4.088 (0.7); 4.071 (1.1); 4.053 (1.2); 4.037 (0.7); 3.902 (4.0); 3.317 (133.5); 2.670 (1.2); 2.505 (143.3); 2.501 (190.5); 2.328 (1.2); 2.196 (13.6); 1.250 (0.3); 1.236 (0.5); 1.189 (16.0); 1.173 (16.0); 0.000 (1.6)

Example 19

$^1$H-NMR (400.0 MHz, d$_6$-DMSO): δ=9.146 (1.2); 9.131 (7.2); 9.021 (0.7); 9.015 (0.8); 9.009 (3.7); 9.003 (3.8); 8.446 (3.8); 8.440 (3.8); 8.348 (0.6); 8.342 (0.6); 7.706 (3.0); 7.668 (3.0); 3.902 (7.5); 3.317 (134.1); 3.031 (16.0); 2.819 (0.3); 2.810 (0.7); 2.802 (0.8); 2.793 (1.3); 2.782 (3.5); 2.766 (0.4); 2.675 (0.8); 2.670 (1.1); 2.666 (0.9); 2.506 (127.3); 2.501 (172.2); 2.497 (135.2); 2.414 (0.9); 2.396 (2.8); 2.377 (2.8); 2.358 (1.0); 2.332 (0.8); 2.328 (1.0); 2.324 (0.8); 2.103 (13.1); 1.249 (0.4); 1.236 (0.5); 1.058 (3.9); 1.048 (1.2); 1.039 (8.5); 1.029 (1.9); 1.020 (3.9); 1.011 (0.9); 0.834 (0.5); 0.824 (0.4); 0.815 (0.5); 0.782 (0.5); 0.610 (0.4); 0.589 (2.1); 0.581 (3.1); 0.571 (1.1); 0.551 (1.4); 0.538 (2.1); 0.522 (2.0); 0.504 (0.4); 0.000 (1.9)

Example 20

$^1$H-NMR (400.0 MHz, d$_6$-DMSO): δ=9.162 (8.4); 9.151 (0.4); 9.023 (4.3); 9.017 (4.4); 8.754 (2.3); 8.743 (2.4); 8.336 (4.4); 8.330 (4.4); 7.708 (3.2); 7.670 (3.2); 3.998 (0.6); 3.902 (6.7); 3.318 (193.4); 2.882 (0.6); 2.873 (1.0); 2.864 (1.4); 2.854 (1.4); 2.845 (1.0); 2.836 (0.7); 2.610 (1.3); 2.666 (1.0); 2.505 (152.0); 2.501 (205.2); 2.497 (165.4); 2.407 (1.2); 2.388 (3.4); 2.369 (3.5); 2.350 (1.3); 2.328 (1.3); 2.324 (1.0); 2.092 (16.0); 1.249 (0.4); 1.235 (0.7); 1.041 (4.8); 1.022 (10.0); 1.003 (4.5); 0.764 (0.8); 0.751 (2.6); 0.747 (3.4); 0.734 (3.3); 0.729 (2.8); 0.717 (1.1); 0.577 (1.1); 0.566 (3.3); 0.559 (3.3); 0.550 (2.9); 0.538 (0.9); 0.000 (1.4)

Example 21

$^1$H-NMR (400.0 MHz, d$_6$-DMSO): δ=9.193 (1.2); 9.182 (6.7); 9.027 (0.7); 9.016 (3.6); 9.011 (3.6); 8.469 (3.5); 8.463

(3.5); 8.363 (0.6); 8.358 (0.6); 8.053 (3.4); 7.947 (3.2); 3.903 (8.4); 3.318 (203.6); 3.038 (16.0); 2.820 (0.4); 2.810 (0.8); 2.802 (0.9); 2.794 (1.5); 2.781 (3.4); 2.766 (0.5); 2.675 (1.1); 2.670 (1.4); 2.506 (162.3); 2.501 (214.1); 2.497 (170.7); 2.332 (0.9); 2.328 (1.3); 2.204 (13.7); 1.250 (0.4); 1.236 (0.7); 0.833 (0.6); 0.825 (0.5); 0.814 (0.5); 0.785 (0.5); 0.610 (0.5); 0.589 (2.4); 0.581 (3.2); 0.549 (1.4); 0.537 (2.3); 0.520 (2.1); 0.503 (0.5); 0.000 (1.3)

Example 22

$^1$H-NMR (400.0 MHz, $d_6$-DMSO): δ=9.208 (7.9); 9.030 (4.1); 9.024 (4.1); 8.759 (2.4); 8.749 (2.5); 8.344 (4.2); 8.338 (4.2); 8.055 (3.6); 7.949 (3.4); 3.902 (2.7); 3.378 (0.5); 3.322 (383.3); 3281 (0.7); 2.882 (0.7); 2.873 (1.0); 2.864 (1.4); 2.855 (1.4); 2.846 (1.0); 2.837 (0.7); 2.670 (1.4); 2.501 (223.7); 2.328 (1.4); 2.192 (16.0); 1.248 (0.4); 1.236 (0.6); 0.765 (0.9); 0.752 (2.7); 0.747 (3.5); 0.735 (3.4); 0.729 (2.9); 0.718 (1.1); 0.578 (1.1); 0.567 (3.5); 0.561 (3.6); 0.552 (3.1); 0.540 (0.9); 0.000 (1.6)

Example 23

$^1$H-NMR (400.0 MHz, $d_6$-DMSO): δ=9.459 (1.2); 9.443 (2.4); 9.428 (1.2); 9.200 (9.1); 9.071 (4.6); 9.065 (4.7); 8.373 (4.7); 8.367 (4.7); 8.313 (0.6); 7.707 (3.1); 7.669 (3.1); 4.200 (0.6); 4.175 (1.9); 4.159 (1.9); 4.151 (2.1); 4.135 (1.9); 4.127 (0.8); 4.1 11 (0.6); 3.316 (112.0); 2.675 (0.6); 2.611 (0.9); 2.666 (0.7); 2.510 (49.8); 2.506 (97.1); 2.501 (130.5); 2.497 (101.5); 2.412 (1.1); 2.394 (3.3); 2.375 (3.4); 2.356 (1.2); 2.333 (0.7); 2.328 (0.9); 2.324 (0.7); 2.097 (16.0); 1.297 (0.5); 1.280 (1.0); 1.247 (5.0); 1.046 (5.0); 1.021 (10.6); 1.008 (4.8); 0.875 (2.1); 0.859 (6.2); 0.841 (2.6); 0.146 (0.8); 0.008 (7.6); 0.000 (161.1); −0.008 (8.4); −0.150 (0.8)

Example 24

$^1$H-NMR (400.0 MHz, $d_6$-DMSO): δ=9.178 (7.1); 9.021 (3.6); 9.015 (3.7); 8.502 (1.5); 8.572 (1.5); 8.311 (4.1); 8.305 (3.7); 7.706 (2.3); 7.667 (2.3); 4.088 (0.6); 4.072 (0.9); 4.053 (1.0); 4.037 (0.6); 3.314 (63.3); 3.291 (0.5); 2.675 (0.6); 2.670 (0.8); 2.686 (0.6); 2.523 (2.6); 2.510 (43.3); 2.506 (87.1); 2.501 (118.3); 2.497 (90.4); 2.492 (46.3); 2.41 1 (0.8); 2.392 (2.5); 2.373 (2.6); 2.355 (0.9); 2.332 (0.6); 2.328 (0.8); 2.324 (0.6); 2.096 (12.2); 1.246 (1.0); 1189 (16.0); 1.1 73 (15.9); 1.045 (3.9); 1.026 (8.5); 1.008 (3.8); 0.815 (0.4); 0.859 (1.3); 0.841 (0.6); 0.146 (0.7); 0.020 (0.5); 0.008 (6.5); 0.000 (152.7); 0.008 (6.9); −0.150 (0.7)

Example 25

$^1$H-NMR (400.0 MHz, $d_6$-DMSO): δ=9.171 (9.7); 9.029 (5.0); 9.023 (5.1); 8.713 (1.1); 8.700 (2.1); 8.686 (1.1); 8.343 (5.2); 8.331 (5.2); 8.313 (1.7); 7.706 (3.1); 7.668 (3.0); 4.033 (0.3); 3.334 (1.3); 3.315 (93.8); 3.302 (3.9); 3.298 (3.6); 3.284 (2.9); 3.266 (0.9); 2.619 (0.3); 2.65 (0.7); 2.60 (0.9); 2.666 (0.7); 2.524 (2.9); 2.510 (51.8); 2.506 (104.0); 2.501 (141.4); 2.497 (110.7); 2.492 (58.7); 2.41 1 (1.1); 2.392 (3.4); 2.313 (3.5); 2.354 (1 2); 2.337 (0.4); 2.333 (0.7); 2.38 (1.0); 2.324 (0.8); 2.096 (16.0); 1.246 (0.7); 1.169 (5.9); 1.151 (12.5); 1.133 (5.7); 1.045 (5.1); 1.026 (11.1); 1.007 (4.9); 0.859 (0.9); 0.841 (0.4); 0.146 (0.8); 0.008 (8.6); 0.000 (181 1); −0.008 (10.0); −0.150 (0.8)

Example 26

$^1$H-NMR (400.0 MHz, $d_6$-DMSO): δ=9.463 (1.1); 9.448 (2.4); 9.432 (1.1); 9.249 (9.0); 9.080 (4.5); 9.074 (4.6); 8.381 (4.7); 8.375 (4.6); 8.313 (0.5); 8.053 (3.3); 7.949 (3.1); 4.200 (0.6); 4.176 (1.9); 4.160 (1.9); 4.152 (2.0); 4.136 (1.9); 4.128 (0.8); 4.112 (0.6); 3.315 (96.3); 2.675 (0.8); 2.670 (1.1); 2.666 (0.8); 2.506 (126.2); 2.501 (168.9); 2.497 (129.8); 2.332 (0.8); 2.328 (1.1); 2.324 (0.8); 2.198 (16.0); 1.279 (0.4); 1.247 (1.9); 0.875 (0.8); 0.859 (2.3); 0.841 (1.0); 0.146 (0.9); 0.008 (9.5); 0.000 (197.7); −0.008 (9.7); −0 150 (1.0)

Example 27

$^1$H-NMR (400.0 MHz, $d_6$-DMSO): δ=9.219 (10.0); 9.035 (4.9); 9.029 (5.0); 8.718 (1.1); 8.704 (2.1); 8.690 (1.0); 8.350 (5.2); 8.344 (5.1); 8.313 (1.1); 8.051 (3.2); 7.948 (3.0); 5.753 (0.4); 3.334 (1.4); 3.315 (99.7); 3.303 (3.7); 3.299 (3.4); 3.285 (2.8); 3.261 (0.9); 2.675 (0.7); 2.670 (1.0); 2.666 (0.7); 2.523 (3.1); 2.510 (52.3); 2.506 (104.9); 2.501 (142.4); 2.497 (109.4); 2.492 (55.8); 2.331 (0.3); 2.333 (0.7); 2.328 (0.9); 2.324 (0.7); 2.196 (16.0); 1.169 (5.8); 1.151 (12.5); 1.133 (5.7); 0.859 (0.4); 0.146 (0.9); 0.008 (8.4); 0.000 (191.4); −0.009 (8.6); −0.150 (0.8)

Example 28

$^1$H-NMR (400.0 MHz, $d_6$-DMSO): δ=9.463 (0.9); 9.448 (2.0); 9.432 (0.9); 9.292 (8.0); 9.108 (4.0); 9.102 (4.1); 8.416 (4.1); 8.410 (4.1); 8.313 (0.5); 8.166 (16.0); 7.908 (2.5); 7.905 (3.4); 7.888 (3.7); 7.885 (3.3); 7.582 (0.9); 7.578 (1.3); 7.573 (0.7); 7.561 (3.8); 7.542 (3.4); 7.536 (1.7); 7.532 (2.4); 7.522 (0.7); 7.515 (1.6); 7.497 (0.5); 4.204 (0.5); 4.180 (1.6); 4.164 (1.6); 4.156 (1.7); 4.140 (1.6); 4.132 (0.7); 4.1 15 (0.5); 3.315 (81.0); 2.675 (0.7); 2.670 (1.0); 2.666 (0.8); 2.510 (56.3); 2.506 (110.3); 2.501 (148.5); 2.497 (114.4); 2.492 (59.3); 2.333 (0.7); 2.328 (1.0); 2.324 (0.7); 0.146 (0.9); 0.008 (9.6); 0.000 (188.1); −0.008 (9.1); −0.150 (0.9)

Example 29

$^1$H-NMR (400.0 MHz, $d_6$-DMSO): δ=9.210 (7.2); 9.056 (3.6); 9.050 (3.7); 8.589 (1.6); 8.519 (1.7); 8.350 (3.7); 8.344 (3.7); 8.313 (0.5); 8.164 (14.5); 7.908 (2.3); 7.904 (3.2); 7.881 (3.5); 7.582 (0.8); 7.577 (1.2); 7.513 (0.7); 7.560 (3.6); 7.542 (3.2); 7.535 (1.6); 7.532 (2.2); 7.521 (0.6); 7.514 (1.5); 7.496 (0.4); 5.753 (1.4); 4.092 (0.6); 4.076 (1.0); 4.057 (1.0); 4.040 (0.7); 3.315 (107.5); 2.615 (0.7); 2.610 (0.9); 2.666 (0.7); 2.510 (51.6); 2.506 (102.0); 2.501 (131.6); 2.497 (105.6); 2.493 (54.2); 2.331 (0.4); 2.332 (0.7); 2.328 (0.9); 2.324 (0.7); 1.218 (0.4); 1.246 (1.9); 1.213 (0.5); 1.195 (16.0); 1.178 (15.7); 0.815 (0.8); 0.859 (2.5); 0.841 (1.0); 0.146 (0.8); 0.008 (8.6); 0.000 (185.3); −0.008 (8.5); −0.027 (0.3); −0.150 (0.9)

Example 30

$^1$H-NMR (400.0 MHz, $d_6$-DMSO): δ=9.262 (8.0); 9.064 (4.1); 9.058 (4.5); 8.720 (1.3); 8.706 (2.6); 8.693 (1.3); 8.384 (4.4); 8.318 (4.6); 8.313 (0.4); 8.163 (16.0); 7.904 (4.6); 7.885 (5.3); 7.577 (1.7); 7.560 (4.9); 7.541 (4.5); 7.532 (3.2); 7.521 (1.0); 7.514 (2.1); 7.496 (0.6); 5.753 (0.4); 4.039 (0.5); 4.021 (0.4); 3.338 (1.2); 3.315 (82.7); 3.289 (3.1); 3.211 (1.0); 2.611 (1.0); 2.501 (147.5); 2.328 (1.0); 1.988 (1.6); 1.193 (0.5); 1.174 (6.1); 1.156 (11.4); 1.138 (5.3); 0.146 (0.7); 0.000 (138.7); −0.150 (0.7)

Example 31

$^1$H-NMR (400.0 MHz, $d_6$-DMSO): δ=9.232 (1.1); 9.215 (6.8); 9.056 (0.7); 9.049 (3.6); 9.043 (3.4); 8.500 (3.5);

8.495 (3.4); 8.392 (0.5); 8.386 (0.5); 8.313 (0.3); 8.162 (16.0); 7.908 (2.5); 7.904 (3.4); 7.88 (3.7); 7.885 (3.2); 7.582 (0.9); 7.577 (1.3); 7.572 (0.7); 7.560 (3.8); 7.541 (3.3); 7.535 (1.6); 7.531 (2.3); 7.521 (0.7); 7.514 (1.6); 7.496 (0.4); 3.316 (89.5); 3.042 (14.0); 2.818 (0.6); 2.810 (0.7); 2.801 (1.1); 2.787 (2.7); 2.774 (0.4); 2.675 (0.5); 2.671 (0.7); 2.666 (0.5); 2.51 1 (39.5); 2.506 (77.8); 2.502 (105.0); 2.497 (80.0); 2.493 (40.7); 2.333 (0.5); 2.328 (0.6); 2.324 (0.5); 1.258 (0.5); 1.247 (1.3); 0.875 (0.6); 0.859 (1.8); 0.841 (0.9); 0.828 (0.3); 0.816 (0.3); 0.789 (0.4); 0.614 (0.4); 0.593 (1.8); 0.585 (2.6); 0.576 (0.9); 0.555 (1.2); 0.543 (1.8); 0.526 (1.6); 0.508 (0.4); 0.146 (0.6); 0.008 (6.4); 0.000 (136.3); −0.008 (6.0); −0.150 (0.6)

Example 32

$^1$H-NMR (400.0 MHz, d$_6$-DMSO): δ=9.249 (7.9); 9.058 (3.9); 9.052 (4.1); 8.759 (2.4); 8.748 (2.4); 8.378 (4.1); 8.372 (4.2); 8.313 (0.5); 8.162 (16.0); 7.903 (4.0); 7.885 (4.5); 7.577 (1.5); 7.560 (4.5); 7.541 (4.0); 7.532 (2.7); 7.521 (0.8); 7.514 (1.9); 7.496 (0.5); 4.038 (0.4); 4.021 (0.4); 3.315 (76.7); 2.887 (0.6); 2.877 (0.9); 2.868 (1.4); 2.859 (1.4); 2.850 (1.0); 2.841 (0.7); 2.610 (1.1); 2.501 (165.4); 2.497 (135.3); 2.328 (1.1); 1.988 (1.6); 1.193 (0.4); 0.175 (0.8); 1.158 (0.4); 0.768 (0.8); 0.754 (2.6); 0.750 (3.4); 0.737 (3.3); 0.732 (2.8); 0.720 (1.1); 0.585 (1.1); 0.574 (3.4); 0.568 (3.4); 0.559 (3.0); 0.547 (0.9); 0.146 (0.9); 0.000 (179.1); −0.150 (0.9)

Example 33

1H-NMR (400.0 MHz, CD3CN): □=8.991 (8.4); 8.986 (8.8); 8.536 (16.0); 8.514 (0.5); 8.363 (0.3); 8.340 (9.2); 8.336 (9.3); 8.044 (9.5); 7.974 (0.7); 7.829 (8.4); 7.586 (0.5); 7.084 (3.5); 2.887 (2.5); 2.877 (2.7); 2.867 (3.6); 2.859 (3.7); 2841 (1.8); 2.771 (0.9); 2.462 (2.1); 2.264 (0.5); 2.149 (52.5); 2.113 (2.6); 2.107 (2.7); 2.101 (2.1); 2.077 (0.3); 2.057 (0.4); 2.032 (0.4); 1.949 (175.5); 1.944 (292.5); 1.936 (377.7); 1.938 (371.4); 1.933 (301.4); 1.927 (181.4); 1.766 (2.2); 1.761 (1.8); 1.323 (0.4); 1.269 (7.0); 1.221 (0.5); 1.202 (0.6); 1.186 (0.4); 0.881 (1.1); 0.855 (1.1); 0.813 (2.2); 0.796 (8.8); (4.9); 0.048 (0.7); −0.001 (897.2); −0.002 (880.8); −0.150 (5.0)

Example 34

1H-NMR (400.0 MHz, d6-DMSO): □=9.656 (9.9); 9.589 (0.5); 9.316 (16.0); 9.296 (1.0); 9.280 (0.5); 9.087 (8.5); 9.081 (9.0); 8.947 (0.4); 8.943 (0.4); 8.492 (8.8); 8.486(8.8); 8.337 (7.7); 8.315 (0.4); 8.212 (0.7); 8.059 (6.7); 4.057 (1.2); 4.039 (3.8); 4.021 (3.8); 4.003 (1.3); 3.319 (115.4); 2.676 (0.9); 2.671 (1.2); 2.667 (1.0); 2.507 (145.7); 2.502 (189.4); 2.498 (146.6); 2.334 (0.9); 2.329 (1.2); 2.325 (1.0); 1.989 (15.7); 1.638 (3.3); 1.624 (8.5); 1.617 (9.4); 1.604 (4.0); 1.563 (0.4); 1.398 (0.8); 1.383 (0.4); 1.343 (4.3); 1.329 (8.6); 1.323 (9.1); 1.308 (3.1); 1.270 (0.3); 1.260 (0.4); 1.236 (2.2); 1.193 (4.3); 1.176 (8.4); 1.158 (4.1); 0.854 (0.4); 0.000 (48.0)

Example 35

1H-NMR (400.0 MHz, CD3CN): 8.985 (3.4); 8.979 (3.4); 8.530 (5.8); 8.507 (0.5); 8.301 (3.1); 8.295 (3.0); 8.241 (0.5); 8.235 (0.5); 8.045 (3.2); 7.831 (2.8); 5.447 (3.4); 4.068 (0.7); 4.051 (0.7); 3.078 (16.0); 2.818 (2.6); 2.804 (0.4); 2.794 (0.7); 2.786 (0.8); 2.778 (1.8); 2.767 (0.8); 2.760 (0.7); 2.749 (0.3); 2.162 (82.5); 2.160 (74.0); 1.972 (3.9); 1.964 (2.4); 1.958 (4.6); 1.952 (17.3); 1.946 (30.2); 1.940 (40.1); 1.934 (28.7); 1.928 (28.7); 1.928 (15.3); 1.437 (1.6); 1.270 (1.5); 1.222 (0.9); 1.204 (1.7); 1.186 (0.8); 0.859 (0.5); 0.841 (0.5); 0.831 (0.4); 0.803 (0.6); 0.588 (2.1); 0.545 (2.4); 0.535 (1.7); 0.528 (2.1); 0.146 (0.4); 0.008 (6.9); 0.000 (87.5); −0.150 (0.4)

Example 36

1H-NMR (400.0 MHz, CD3CN): 9.012 (0.3); 8.988 (8.6); 8.982 (8.5); 8.497 (16.0); 8.337 (9.5); 8.331 (9.1); 7.899 (8.3); 7.646 (8.3); 7.086 (2.7); 7.031 (3.9); 6.851 (8.0); 6.671 (4.0); 2.895 (0.6); 2.886 (1.7); 2.877 (2.5); 2.868 (3.5); 2.859 (3.5); 2.850 (2.4); 2.840 (1.6); 2.831 (0.6); 2.464 (1.3); 2.334 (0.4); 2.323 (0.4); 2.264 (0.7); 2.246 (0.9); 2.160 (322.3); 2.154 (396.4); 2.1 19 (0.9); 2.1 13 (1.3); 2.107 (1.6); 2.101 (1.1); 1.964 (11.0); 1.952 (115.8); 1.946 (204.6); 1.940 (271.6); 1.934 (192.2); 1.927 (99.5); 1.781 (0.5); 1.774 (1.0); 1.768 (1.4); 1.762 (0.9); 1.756 (0.5); 1.270 (5.8); 1.252 (0.6); 0.882 (0.7); 0.864 (0.5); 0.813 (1.9); 0.796 (8.0); 0.783 (8.0); 0.778 (6.4); 0.766 (2.4); 0.744 (0.3); 0.665 (0.4); 0.635 (2.7); 0.623 (7.6); 0.617 (8.1); 0.609 (6.7); 0.596 (1.8); 0.549 (0.4); 0.146 (3.2); 0.000 (618.3); −0.150 (3.1)

Example 37

1H-NMR (400.0 MHz, CD3CN): □=8,981 (3,3); 8,975 (3,2); 8,495 (5,3); 8,470 (0,4); 8,298 (2,8); 8,292 (2, 7); 8,236 (0,4); 8,230 (0,4); 7,900 (2.8); 7.647 (2.8); 7.041 (1.4); 6.861 (2.7); 6.681 (1.4); 4.086 (0.6); 4.068 (1.8); 4.051 (1.8); 4.033 (0.6); 3.077 160 2.817 (2.5); 2.804 (0.3); 2.794 (0.6); 2.787 (0.6); 2.778 (1.1); 2.767 (0.7); 2.760 (0.6); 2.466 (1.0); 2.461 (0.5); 2.182 (181.0); 2.1 14 (0.3); 2.107 (0.4); 1.972 (8.0); 1.964 (2.2); 1.958 (5.1); 1.952 (2.86); 1.946 (5.17); 1.940 (6.99); 1.934 (4.78); 1.928 (2.43); 1.768 (0.4); 1.437 (8.7); 1.270 (0.9); 1.222 (2.1); 1.204 (4.1); 1.186 (2.0); 0.858 (0.4); 0.841 (0.4); 0.802 (0.5); 0.587 (1.8); 0.554 (1.2); 0.545 (2.0); 0.536 (1.3); 0.529 (1.8); 0.515 (0.4); 0.146 (0.9); 0.007 (9.0); 0.000 (193.1); −0.009 (7.7); −0.150 (0.9)

Example 38

1H-NMR (400.0 MHz, CD3CN): □=9.033 (3.8); 9.027 (3.9); 8.523 (0.4); 8.510 (8.2); 8.406 (4.0); 8.400 (3.9); 7.900 (3.0); 7.754 (1.0); 7.646 (3.1); 7.586 (0.4); 7.033 (2.1); 6.853 (4.3); 6.673 (2.1); 4.086 (0.9); 4.068 (3.0); 4.050 (3.1); 4.033 (1.0); 2.468 (0.6); 2.464 (0.8); 2.459 (0.6); 2.454 (0.4); 2.373 (0.7); 2.150 (189.8); 2.145 (234.4); 2.1 19 (1.7); 2.1 13 (1.9); 2.107 (2.1); 2.101 (1.5); 2.095 (0.9); 1.972 (14.1); 1.964 (8.2); 1.958 (18.7); 1.952 (110.1); 1.946 (202.1); 1.940 (275.0); 1.933 (190.6); 1.927 (98.2); 1.780 (0.7); 1.774 (1.3); 1.768 (1.7); 1.762 (1.2); 1.756 (0.6); 1.612 (1.7); 1.597 (4.3); 1.591 (4.2); 1.577 (2.3); 1.537 (0.3); 1.437 (16.0); 1.391 (2.4); 1.377 (4.2); 1.370 (4.3); 1.356 (1.7); 1.349 (0.4); 1.271 (1.7); 1.222 (3.7); 1.204 (7.0); 1.186 (3.5); 0.146 (3.4); 0.008 (34.0); 0.000 (712.2); −0.008 (31.3); −0.150 (3.4)

BIOLOGICAL EXAMPLES

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 μl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm$^2$. 100% efficacy means that all the fleas were dead or moribund. 0% efficacy means that no fleas were harmed.

In this test, for example, the following compounds from the preparation examples show an efficacy of 100% at an application rate of 500 g/ha (5 µg/cm$^2$): 1, 2, 5, 6, 8, 9, 12, 13, 15, 17

In this test, for example, the following compounds from the preparation examples show an efficacy of 80% at an application rate of 500 g/ha (5 µg/cm$^2$): 14

*Rhipicephalus sanguineus*—In Vitro Contact Tests with Adult Brown Dog Ticks

For the coating of the test tubes, 9 mg of active compound are first dissolved in 1 ml of acetone p.a. and then diluted to the desired concentration with acetone p.a. 250 µl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm$^2$, given homogeneous distribution, an area-based dose of 5 µg/cm$^2$ is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the floor of the tube and incubated on a hotplate at 45-50° C. for not more than 5 min. Ticks which remain motionless on the floor or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 µg/cm$^2$. An efficacy of 100% means that all the ticks were dead or moribund. 0% efficacy means that none of the ticks had been harmed.

In this test, for example, the following compounds from the preparation examples show an efficacy of 100% at an application rate of 500 g/ha (5 µg/cm$^2$): 1, 2, 3, 5, 8, 13, 14

In this test, for example, the following compounds from the preparation examples show an efficacy of 80% at an application rate of 500 g/ha (5 µg/cm$^2$): 12

In this test, for example, the following compounds from the preparation examples show an efficacy of 100% at an application rate of 20 g/ha (0.2 µg/cm$^2$): 9

*Amblyomma hebaraeum* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

Tick nymphs (*Amblyomma hebraeum*) are placed into perforated plastic beakers and immersed in the desired concentration for one minute. The ticks are transferred on filter paper into a Petri dish and stored in a climate-controlled cabinet.

After 42 days, the kill in % is determined. 100% means that all of the ticks have been killed; 0% means that none of the ticks have been killed.

In this test, for example, the following compounds from the preparation examples show an efficacy of 100% at an application rate of 100 ppm: 2, 3, 5, 8, 9

In this test, for example, the following compounds from the preparation examples show an efficacy of 80% at an application rate of 100 ppm: 1

*Boophilus microplus*—Dip Test
Test animals: cattle ticks (*Boophilus microplus*) Parkhurst strain, SP-resistant
Solvent: dimethyl sulphoxide 10 mg of active compound are dissolved in 0.5 ml of dimethyl sulphoxide. To produce a suitable formulation, the active compound solution is diluted with water to the concentration desired in each case.

This active compound preparation is pipetted into tubes. 8-10 engorged adult female cattle ticks (*Boophilus microplus*) are transferred into a further tube with holes. The tube is immersed into the active compound preparation, and all the ticks are completely wetted. After the liquid has run out, the ticks are transferred on filter discs into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds of the preparation examples show an efficacy of 100% at an application rate of 100 ppm: 1, 2, 3, 5, 6, 8, 9, 13, 14, 15, 16, 17, 19, 20, 21, 22, 25, 27, 33

In this test, for example, the following compounds from the preparation examples show an efficacy of 80% at an application rate of 100 ppm: 12

*Boophilus microplus*—Injection Test
Solvent: dimethyl sulphoxide

To produce a suitable preparation of active compound, 10 mg of active compound are mixed with 0.5 ml of solvent and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds of the preparation examples show an efficacy of 100% at an application rate of 20 µg/animal: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35

*Ctenocephalides felis*—Oral Test
Solvent: dimethyl sulphoxide

To produce a suitable preparation of active compound, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: 1, 2, 3, 4, 5, 6, 7, 8, 9, 10, 11, 12, 13, 14, 15, 16, 17, 18, 19, 20, 21, 22, 23, 24, 25, 26, 27, 28, 30, 31, 32, 33, 34, 35

*Lucilia cuprina* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: 1, 2, 3, 4, 5, 6, 7, 9, 11, 12, 13, 15, 16, 17, 18, 19, 20, 21, 22, 23, 25, 26, 27, 30, 31, 32, 33, 34, 35

In this test, for example, the following compounds from the preparation examples show an efficacy of 95% at an application rate of 100 ppm: 10

In this test, for example, the following compounds from the preparation examples show an efficacy of 90% at an application rate of 100 ppm: 8, 14

*Musca domestica* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: 1, 2, 3, 4, 5, 6, 9, 11, 12, 13, 14, 15, 16, 17, 18, 21, 22, 26, 27, 33, 34, 35

In this test, for example, the following compounds from the preparation examples show an efficacy of 95% at an application rate of 100 ppm: 8

In this test, for example, the following compounds from the preparation examples show an efficacy of 80% at an application rate of 100 ppm: 19, 25

*Myzus Persicae*—Spray Test
Solvent: 78 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that none of the aphids have been killed.

In this test, for example, the following compounds from the preparation examples show efficacy of 90% at an application rate of 100 g/ha: 1, 2, 12, 13, 15, 16, 35

*Phaedon Cochleariae*—Spray Test
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show efficacy of 100% at an application rate of 100 g/ha: 1, 2, 3, 4, 5, 6, 7, 8, 9, 11, 12, 13, 14, 15, 16, 17, 34, 35

*Spodoptera Frugiperda*—Spray Test
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound preparation of the desired concentration and, after drying, populated with caterpillars of the armyworm (Spodopterafrugiperda).

After 7 days, the efficacy in % is determined. 100% means that all the caterpillars have been killed; 0% means that no caterpillars have been killed.

In this test, for example, the following compounds from the preparation examples show efficacy of 100% at an application rate of 100 g/ha: 1, 2, 3, 4, 5, 6, 7, 11, 12, 13, 14, 15, 16, 35

Tetranychus Urticae—Spray Test, OP-Resistant
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (Phaseolus vulgaris) infested with all stages of the greenhouse red spider mite (Tetranychus urticae) are sprayed with an active compound preparation of the desired concentration.

After 6 days, the efficacy in % is determined. 100% means that all the spider mites have been killed; 0% means that none of the spider mites have been killed.

In this test, for example, the following compounds of the preparation examples show an efficacy of 100% at an application rate of 100 g/ha: 1, 5, 6, 8, 9, 12, 13, 14, 15, 16, 17, 34, 35

In this test, for example, the following compounds from the preparation examples show an efficacy of 90% at an application rate of 100 g/ha: 2

In this test, for example, the following compounds of the preparation examples show an efficacy of 90% at an application rate of 20 g/ha: 3, 11

Anopheles Test (ANPHGB Surface Treatment)
Solvent: acetone+2000 ppm rapeseed oil methyl ester (RME)

To produce an appropriate active compound formulation, the active compound is dissolved in the solvent (2 mg/ml). The active compound formulation is pipetted onto a glazed tile and, after it has dried off, adult mosquitoes of the species Anopheles gambiae strain RSPH (homozygot kdr) are placed onto the treated tile. The exposure time is 30 minutes.

24 hours after contact with the treated surface, mortality in % is determined. 100% means that all the mosquitoes have been killed; 0% means that none of the mosquitoes have been killed.

In this test, for example, the following compounds from the preparation examples show efficacy of 90-100% at an application rate of 40 mg/m$^2$: 16

Anopheles Test (ANPHFU Surface Treatment)
Solvent: acetone+2000 ppm rapeseed oil methyl ester (RME)

To produce an appropriate active compound formulation, the active ingredient is dissolved in the solvent (2 mg/ml). The active compound formulation is pipetted onto a glazed tile and, after it has dried off, adult mosquitoes of the species Anopheles funestus strain FUMOZ-R (Hunt et al., Med Vet Entomol. 2005 September; 19(3):271-5) are placed onto the treated tile. The exposure time is 30 minutes.

24 hours after contact with the treated surface, mortality in % is determined. 100% means that all the mosquitoes have been killed; 0% means that none of the mosquitoes have been killed.

In this test, for example, the following compounds from the preparation examples show efficacy of 90-100% at an application rate of 40 mg/m$^2$: 16

Aedes test (AEDSAE surface treatment)
Solvent: acetone+2000 ppm rapeseed oil methyl ester (RME)

To produce an appropriate active ingredient formulation, the active ingredient is dissolved in the solvent (2 mg/ml). The active compound formulation is pipetted onto a glazed tile and, after it has dried off, adult mosquitoes of the species Aedes aegypti strain MONHEIM are placed onto the treated tile. The exposure time is 30 minutes.

24 hours after contact with the treated surface, mortality in % is determined. 100% means that all the mosquitoes have been killed; 0% means that none of the mosquitoes have been killed.

In this test, for example, the following compounds from the preparation examples show efficacy of 90-100% at an application rate of 40 mg/m$^2$: 6, 9, 16

The invention claimed is:
1. Compound of formula (I)

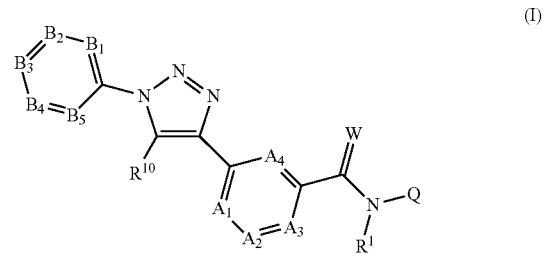

in which
R$^1$ represents hydrogen, unsubstituted or cyano-substituted C$_1$-C$_6$-alkyl, C$_3$-C$_6$-alkenyl, C$_3$-C$_6$-alkynyl, C$_3$-C$_7$-cycloalkyl, C$_1$-C$_6$-alkylcarbonyl, C$_1$-C$_6$-alkoxycarbonyl, or aryl-C$_1$-C$_6$-alkyl;
the chemical moieties
A$_1$ represents CR$^2$,
A$_2$ represents nitrogen,
A$_3$ represents CR$^3$,
A$_4$ represents CR$^4$,
B$_1$ represents CR$^5$,
B$_2$ represents CR$^6$,
B$_3$ represents CR$^7$,
B$_4$ represents CR$^8$, and
B$_5$ represents CR$^9$,
R$^2$, R$^3$, R$^4$, R$^5$, R$^6$, R$^8$ and R$^9$ independently of one another represent hydrogen, halogen, cyano, nitro, in each case optionally halogen-substituted C$_1$-C$_6$-alkyl, C$_3$-C$_7$cycloalkyl, C$_1$-C$_6$-alkoxy, N—(C$_1$-C$_6$-alkoxy)imino-C$_1$-C$_3$-alkyl, C$_1$-C$_6$-alkylsulphanyl, C$_1$-C$_6$-alkylsulphinyl, C$_1$-C$_6$-alkylsulphonyl, N—(C$_1$-C$_6$-alkyl)amino or NN-di(C$_1$-C$_6$-alkyl)amino, C$_1$-C$_6$-alkylsulphonylamino, N—(C$_1$-C$_6$-alkyl)-C$_1$-C$_6$-alkylsulphonylamino, or phenyl;
R$^7$ represents halogen, cyano, nitro, in each case optionally halogen-substituted C$_1$-C$_6$-alkyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulphanyl, C$_1$-C$_6$-alkylsulphinyl, C$_1$-C$_6$-alkylsulphonyl, N—C$_1$-C$_6$-alkylamino, N,N-di-C$_1$-C$_6$-alkylamino or phenyl;
R$^{10}$ independently of one another represents hydrogen, halogen, cyano, nitro, amino or optionally halogen-substituted C$_1$-C$_6$-alkyl, C$_1$-C$_6$-alkyloxy, C$_1$-C$_6$-alkylcarbonyl, C$_1$-C$_6$-alkylsulphanyl, C$_1$-C$_6$-alkylsulphinyl, or C$_1$-C$_6$-alkylsulphonyl;
W represents oxygen or sulphur;

Q represents hydrogen, formyl, hydroxy, amino, or one of the optionally halogen-substituted moieties $C_1$-$C_6$-alkyl, $C_1$-$C_6$-alkyloxy, $C_3$-$C_6$-alkenyl, $C_3$-$C_6$-alkynyl, $C_3$-$C_7$-cycloalkyl, $C_3$-$C_6$-cycloalkyl-$C_1$-$C_6$-alkyl, or aryl—$C_1$-$C_6$-alkyl or represents a moiety N—($C_1$-$C_6$-alkyl)amino, N—($C_1$-$C_6$-alkylcarbonyl)amino, or N,N-di($C_1$-$C_6$-alkyl)amino; or Q represents an unsaturated 6-membered carbocycle which is optionally polysubstituted by V, where V represents halogen, cyano, nitro, or one of the moieties $C_1$-$C_6$-alkyl, $C_2$-$C_6$-alkenyl, $C_2$-$C_6$-alkynyl, $C_3$-$C_7$-cycloalkyl, $C_1$-$C_6$-alkoxy, N—($C_1$-$C_6$-alkoxy)imino-$C_1$-$C_6$-alkyl, $C_1$-$C_6$-alkylsulphanyl, $C_1$-$C_6$-alkylsulphinyl, $C_1$-$C_6$-alkylsulphonyl, or N,N-di($C_1$-$C_6$-alkyl)amino;

and/or a salt, N-oxide and/or a tautomeric form of a compound of the formula (I).

2. Compound of formula (I) and/or a salt, N-oxide and/or a tautomeric form according to claim 1 in which $R^1$ represents hydrogen, methyl, ethyl, n-propyl, isopropyl, n-butyl, isobutyl, s-butyl, t-butyl, methoxymethyl, ethoxymethyl, propoxymethyl, 2-propyn-1-yl, 2-propen-1-yl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, or 4-methoxybenzyl;

the chemical moieties $A_1$ represents $CR^2$,
$A_2$ represents nitrogen,
$A_3$ represents $CR^3$,
$A_4$ represents $CR^4$,
$B_1$ represents $CR^5$,
$B_2$ represents $CR^6$,
$B_3$ represents $CR^7$,
$B_4$ represents $CR^8$, and
$B_5$ represents $CR^9$, $R^2$ and $R^4$ independently of one another represent hydrogen, methyl, fluorine or chlorine; and $R^3$ represents hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, N-methylamino, N,N-dimethylamino, N-ethylamino, N,N-diethylamino, methyl sulphonylamino, or N-methylmethylsulphonylamino;

$R^5$, $R^6$, $R^8$ and $R^9$ independently of one another represent hydrogen, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methyl sulphanyl, trifluoromethylsulphanyl, methylsulphonyl, methyl sulphinyl, trifluoromethylsulphonyl, or trifluoromethylsulphinyl, but where $R^6$ and $R^{10}$ do not simultaneously represent hydrogen, $R^7$ represents perhalogenated $C_1$-$C_6$-alkyl, perhalogenated $C_3$-$C_6$-cycloalkyl, $C_1$-$C_6$-alkoxy, N-alkoxyiminoalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, and also represents fluorine, chlorine, bromine, iodine, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2- trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino, or phenyl;

$R^{10}$ independently of one another represents hydrogen, halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, or trifluoromethylsulphinyl;

W represents oxygen or sulphur;

Q represents hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropyl ethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3 -dichloroprop-2-enyl, 3, 3-dichloro-1,1 -dimethylprop-2-enyl, phenyl, 2-chlorophenyl, 3-chlorophenyl, 4-chlorophenyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, or 2-oxo-2-(2,2,2-trifluoroethylamino)ethyl; or Q represents phenyl or naphthyl substituted by 0 -4 substituents V, where V independently of one another represents fluorine, chlorine, bromine, iodine, cyano, nitro, methyl, ethyl, isopropyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, or N,N-dimethylamino.

3. Compound of formula (I) and/or a salt, N-oxide and/or a tautomeric according to claim 1 in which $R^1$ represents hydrogen, methyl, ethyl, n-propyl, isopropyl, n-butyl, isobutyl, s-butyl, t-butyl, methoxymethyl, ethoxymethyl, propoxymethyl, 2-propyn-1-yl, 2-propen-1-yl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, or 4-methoxybenzyl;

the chemical moieties
$A_1$ represents CH,
$A_2$ represents nitrogen,
$A_3$ represents $CR^3$, and
$A_4$ represents CH;
$B_1$ represents $CR^5$,
$B_2$ represents CH,
$B_3$ represents $CR^7$,
$B_4$ represents $CR^8$, and
$B_5$ represents $CR^9$, $R^3$ represents hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl, N-methylamino, N,N-dimethylamino, N-ethylamino, N,N-diethylamino, methyl sulphonylamino, or N-methylmethylsulphonylamino;

$R^5$, $R^6$, $R^8$ and $R^9$ independently of one another represent hydrogen, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, or trifluoromethylsulphinyl, but where $R^6$ and $R^{10}$ do not simultaneously represent hydrogen;

$R^7$ represents difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulphonyl, trifluoromethylsulphinyl, trifluoromethylsulphanyl, or phenyl;

$R^{10}$ independently of one another represents hydrogen, halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methyl sulphinyl, methylsulphonyl, trifluoromethylsulphonyl, trifluoromethylsulphanyl, or trifluoromethylsulphinyl;

W represents oxygen; and

Q represents hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, or 2-oxo-2-(2,2,2-trifluoroethylamino)ethyl; or Q represents phenyl or naphthyl substituted by 0 - 4 substituents V, where V independently of one another represents fluorine, chlorine, bromine, iodine, cyano, nitro, methyl, ethyl, isopropyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2chl oro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl 1, trifluoromethylsulphonyl, trifluoromethylsulphinyl, trifluoromethylsulphanyl, or N,N-dimethylamino;

$R^5$ represents hydrogen, methyl, ethyl, 2-methylethyl, tert-butyl, fluorine, chlorine, bromine, iodine, nitro, trifluoromethyl, difluoromethoxy, trifluoromethoxy, or amino.

4. Compound of formula (I) and/or a salt, N-oxide and/or a tautomeric according to claim 1 in which W represents oxygen;

$R^{10}$ represents hydrogen and $R^1$ represents hydrogen or methyl;

$B_3$ represents $CR^7$ and $R^7$ represents perhalogenated $C_1$-$C_4$-alkyl; or $B_3$ represents $CR^7$ and $R^7$ represents perhalogenated $C_1$-$C_4$-alkyl or phenyl;

Q represents cyclopropyl optionally substituted independently by F, Cl, Br, I or CN.

5. Compound of formula (I) and/or a salt, N-oxide and/or a tautomeric according to claim 1 in which W represents oxygen;

$R^{10}$ represents hydrogen and $R^1$ represents hydrogen or methyl;

$B_3$ represents $CR^7$ and $R^7$ represents —$C_3F_7$; or $B_3$ represents $CR^7$ and $F^7$ represents —$C_3F_7$ or phenyl; and Q represents cyclopropyl or 1-cyanocyclopropyl.

6. Compound of formula (I) and/or a salt, N-oxide and/or a tautomeric form according to claim 1 in which $B_1$ represents $CR^5$, and $R^5$ represents halogen, $C_1$-$C_6$-alkoxy or $C_1$-$C_6$-alkyl, halogen-substituted $C_1$-$C_6$-alkoxy or halogen-substituted $C_1$-$C_6$-alkyl;

$B_2$ represents $CR^6$, where $R^6$ represents hydrogen or $C_1$-$C_6$-alkyl;

$B_4$ represents $CR^8$, where $R^8$ represents hydrogen or $C_1$-$C_6$-alkyl;

$B_5$ represents $CR^9$, where $R^9$ represents halogen, $C_1$-$C_6$-alkoxy or $C_1$-$C_6$-alkyl.

7. Compound of formula (I) and/or a salt, N-oxide and/or a tautomeric form according to claim 6 in which $B_1$ represents $CR^5$, and $R^5$ represents Cl, Br, I, $C_1$-$C_6$-alkyl, F-substituted $C_1$-$C_4$-alkyl or F-substituted $C_1$-$C_4$-alkoxy, $B_2$ represents $CR^6$, where $R^6$ represents hydrogen, $B_4$ represents $CR^8$, where $R^8$ represents hydrogen, $B_5$ represents $CR^9$, where $R^9$ represents halogen or $C_1$-$C_4$-alkyl.

8. Compound of formula (I) and/or a salt, N-oxide and/or a tautomeric form according to claim 1 in which $A_1$ represents $CR^2$, where $R^2$ represents hydrogen or $C_1$-$C_4$-alkyl;

$A_2$ represents nitrogen;

$A_3$ represents $CR^3$, where $R^3$ represents halogen, $C_1$-$C_4$-alkyl, $C_1$-$C_4$-haloalkyl or $C_1$-$C_4$-alkoxy; and $A_4$ represents $CR^4$, where $R^4$ represents hydrogen or $C_1$-$C_4$-alkyl.

9. Compound of formula (I) and/or a salt, N-oxide and/or a tautomeric form according to claim 8 in which $A_1$ represents $CR^2$, where $R^2$ represents hydrogen;

$A_2$ represents nitrogen;

$A_3$ represents $CR^3$, where $R^3$ represents halogen, $C_1$-$C_4$-alkyl, $C_1$-$C_4$-haloalkyl or $C_1$-$C_4$-alkoxy; and $A_4$ represents $CR^4$, where $R^4$ represents hydrogen.

10. Compound of formula (I) and/or a salt, N-oxide and/or a tautomeric form according to claim 1 in which W represents oxygen, $R^{10}$ represents hydrogen and $R^1$ represents hydrogen or methyl, $A_1$ represents $CR^2$, where $R^2$ represents hydrogen or $C_1$-$C_4$-alkyl, $A_2$ represents nitrogen, $A_3$ represents $CR^3$, where $R^3$ represents halogen, $C_1$-$C_4$-alkyl, $C_1$-$C_4$-haloalkyl or $C_1$-$C_4$-alkoxy, $A_4$ represents $CR^4$, where $R^4$ represents hydrogen or $C_1$-$C_4$-alkyl, $B_1$ represents $CR^5$, and $R^5$ represents Cl, Br, I, $C_1$-$C_4$-alkyl, F-substituted $C_1$-$C_4$-alkyl or F-substituted $C_1$-$C_4$-alkoxy, $B_2$ represents $CR^6$, where $R^6$ represents hydrogen or $C_1$-$C_6$-alkyl, $B_3$ represents $CR^7$, where $R^7$ represents perhalogenated $C_1$-$C_4$-alkyl or phenyl, $B_4$ represents $CR^8$, where $R^8$ represents hydrogen or $C_1$-$C_6$-alkyl, $B_5$ represents $CR^9$, where $R^9$ represents halogen, $C_1$-$C_6$-alkoxy or $C_1$-$C_6$-alkyl, Q represents cyclopropyl or 1-cyanocyclopropyl.

11. Compound of formula (I) and/or a salt, N-oxide and/or a tautomeric form according to claim 1 in which W represents oxygen, $R^{10}$ represents hydrogen and $R^1$ represents hydrogen or methyl, $A_1$ represents $CR^2$, where $R^2$ represents hydrogen, $A_2$ represents nitrogen, $A_3$ represents $CR^3$, where $R^3$ represents perfluorinated $C_1$-$C_4$-alkyl, $C_1$-$C_4$-alkyl, Cl, F, I or $C_1$-$C_4$-alkoxy, $A_4$ represents $CR^4$, where $R^4$ represents hydrogen, $B_1$ represents $CR^5$, where $R^5$ represents F, Cl, Br, $C_1$-$C_4$-alkyl, F-substituted $C_1$-$C_4$-alkyl or F-substituted $C_1$-$C_4$-alkoxy, $B_2$ represents $CR^6$, where $R^6$ represents hydrogen, $B_3$ represents $CR^7$, where $R^7$ represents perfluorinated $C_1$-$C_4$-alkyl or phenyl, $B_4$ represents $CR^8$, where $R^8$ represents hydrogen, $B_5$ represents $CR^9$, where $R^9$ represents F, Cl, Br, I, $C_1$-$C_4$-alkyl, Q represents cyclopropyl, 1-cyanocyclopropyl, $C_1$-$C_4$-alkyl or fluorinated $C_1$-$C_4$-alkyl.

12. Pharmaceutical composition comprising at least one compound and/or a salt, N-oxide and/or a tautomeric form according to claim 1 and at least one carrier.

13. Compound of formula (I) and/or a salt, N-oxide and/or a tautomeric form according to claim 1 in which $R^1$ represents hydrogen;

$A_1$ represents CH;

$A_2$ represents nitrogen, $A_3$ represents C—Cl;

$A_4$ represents CH;

$B_1$ represents C—Cl;

$B_2$ represents CH;

$B_3$ represents C-i-$C_3F_7$;
$B_4$ represents CH;
$B_5$ represents C—Cl;
$R^{10}$ represents hydrogen;
W represents oxygen; and
Q represents 1-(cyano)cyclopropyl.

14. The compound of formula (I) and/or a salt, N-oxide and/or a tautomeric form according to claim 1 in which
$R^7$ represents halogen, cyano, nitro, $C_1$-$C_6$-haloalkyl or phenyl.

15. The compound of formula (I) and/or a salt, N-oxide and/or a tautomeric form according to claim 2 in which
$R^1$ represents hydrogen, methyl, ethyl, n-propyl, isopropyl, n-butyl, isobutyl, s-butyl or t-butyl.

16. The compound of formula (I) and/or a salt, N-oxide and/or a tautomeric form according to claim 6 in which
$B_1$ represents $CR^5$, and $R^5$ represents halogen, $C_1$-$C_6$-alkoxy or $C_1$-$C_6$-alkyl, F-substituted $C_1$-$C_6$-alkoxy or F-substituted $C_1$-$C_6$-alkyl.

17. The compound of formula (I) and/or a salt, N-oxide and/or a tautomeric form according to claim 11 in which
$A_3$ represents $CR^3$, where $R^3$ represents $C_1$-$C_4$-alkyl, Cl or $C_1$-$C_4$-alkoxy,
$B_1$ represents $CR^5$, where $R^5$ represents —$CF_3$, —$C_2F_5$, —$C_3F_7$, —$C_4F_9$, —$CH_3$, —$C_2H_5$, —$C_3H_7$, —$C_4H_9$, Cl, $OCF_3$, $OCF_2H$ or $OCFH_2$,
$B_3$ represents $CR^7$, where $R^7$ represents —$C_3F_7$ or phenyl,
$B_4$ represents $CR^8$, where $R^8$ represents hydrogen,
$B_5$ represents $CR^9$, where $R^9$ represents Cl, Br, I or $C_1$-$C_4$-alkyl,
Q represents methyl, ethyl, propyl, $C_2H_2F_3$, cyclopropyl or 1-cyanocyclopropyl.

18. The compound of formula (I) and/or a salt, N-oxide and/or a tautomeric form according to claim 11 in which
$A_3$ represents $CR^3$, where $R^3$ represents methyl, methoxy or Cl,
$B_1$ represents $CR^5$, where $R^5$ represents Cl, $CF_3$, $OCF_2H$, $OCF_3$, methyl or ethyl,
$B_3$ represents $CR^7$, where $R^7$ represents —$C_3F_7$ or phenyl,
$B_4$ represents $CR^8$, where $R^8$ represents hydrogen,
$B_5$ represents $CR^9$, where $R^9$ represents Cl, I, Br, methyl or ethyl,
Q represents methyl, ethyl, propyl, $C_2H_2F_3$, cyclopropyl or 1-cyanocyclopropyl.

\* \* \* \* \*